US012662558B2

(12) United States Patent
Jimbo et al.

(10) Patent No.: US 12,662,558 B2
(45) Date of Patent: Jun. 23, 2026

(54) POLYMERIZABLE COMPOSITION, POLYMER, ULTRAVIOLET SHIELDING MATERIAL, LAMINATE, COMPOUND, ULTRAVIOLET ABSORBING AGENT, AND METHOD OF PRODUCING COMPOUND

(71) Applicant: FUJIFILM Corporation, Tokyo (JP)

(72) Inventors: Yoshihiro Jimbo, Shizuoka (JP); Daisuke Sasaki, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 612 days.

(21) Appl. No.: 18/152,123

(22) Filed: Jan. 9, 2023

(65) Prior Publication Data

US 2023/0159675 A1 May 25, 2023

Related U.S. Application Data

(63) Continuation of application No. PCT/JP2021/029869, filed on Aug. 16, 2021.

(30) Foreign Application Priority Data

Aug. 21, 2020 (JP) ................................ 2020-140222
Feb. 1, 2021 (JP) ................................ 2021-014078

(51) Int. Cl.

| | |
|---|---|
| ***C08F 220/38*** | (2006.01) |
| ***C07D 249/20*** | (2006.01) |
| ***C07D 409/04*** | (2006.01) |
| ***C08F 20/38*** | (2006.01) |
| ***C08F 220/14*** | (2006.01) |
| *G02B 1/04* | (2006.01) |

(52) U.S. Cl.

CPC ............ *C08F 20/38* (2013.01); *C07D 249/20* (2013.01); *C07D 409/04* (2013.01); *C08F 220/14* (2013.01); *C08F 220/387* (2020.02); *G02B 1/04* (2013.01)

(58) Field of Classification Search

CPC .. C08F 220/30; C08F 220/302; C08F 220/34; C08F 220/36; C08F 220/38; C08F 220/387; C08F 226/06; C08F 228/06

See application file for complete search history.

(56) References Cited

U.S. PATENT DOCUMENTS 10,921,489 B2 2/2021 Kawaguchi et al.
11,078,180 B2 8/2021 Morooka et al.
11,518,916 B2 12/2022 Nakayama et al.
2009/0189120 A1* 7/2009 Takeuchi ............. C07D 409/04 252/299.61
2010/0025642 A1 2/2010 Hanaki et al.
2010/0130638 A1* 5/2010 Hanaki ................... H10F 19/80 252/589
2018/0311936 A1 11/2018 Jimbo et al.
2020/0180285 A1 6/2020 Iwase
2020/0199095 A1 6/2020 Morooka et al.
2022/0137260 A1 5/2022 Jimbo et al.
2022/0324853 A1 10/2022 Furuyama et al.

FOREIGN PATENT DOCUMENTS

CN 102236255 11/2011
CN 107949584 4/2018
CN 109415573 3/2019
CN 111032704 4/2020
JP 2009096973 5/2009
JP 2009096974 5/2009
JP 2009263616 11/2009
JP 2009263617 11/2009
WO 2009123153 10/2009
WO 2009123154 10/2009
WO 2019044863 3/2019
WO 2019131572 7/2019

(Continued)

OTHER PUBLICATIONS

"Office Action of Japan Counterpart Application", issued on Aug. 8, 2023, with English translation thereof, p. 1-p. 12.
"Office Action of China Counterpart Application", issued on Aug. 30, 2023, with English translation thereof, pp. 1-24.
"Office Action of Japan Counterpart Application", issued on Oct. 17, 2023, with English translation thereof, pp. 1-13.
"Search Report of Europe Counterpart Application", issued on Jan. 31, 2024, p. 1-p. 5.
"Office Action of China Counterpart Application", issued on Dec. 1, 2023, with English translation thereof, p. 1-p. 24.

(Continued)

*Primary Examiner* — Marc S Zimmer
(74) *Attorney, Agent, or Firm* — JCIPRNET

(57) ABSTRACT

Provided is a polymerizable composition including a compound represented by Formula (1), and an ultraviolet absorbing agent A having a maximum absorption wavelength on a shorter wavelength side than a maximum absorption wavelength of the compound represented by Formula (1). Provided are a polymer, an ultraviolet shielding material, a laminate, a compound, an ultraviolet absorbing agent, and a method of producing a compound. In Formula (1), $R^1$ to $R^6$ each independently represent a hydrogen atom or a substituent, where at least one of $R^1$ to $R^6$ represents a group that contains a polymerizable group having an ethylenically unsaturated bond.

(1)

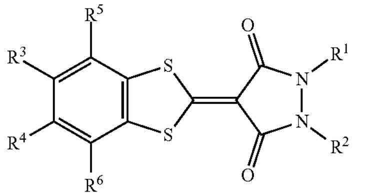

18 Claims, No Drawings

(56) References Cited

FOREIGN PATENT DOCUMENTS

| | | |
|---|---|---|
| WO | 2021029146 | 2/2021 |
| WO | 2021131355 | 7/2021 |

OTHER PUBLICATIONS

Zhongwei Lan et al., "Fundamentals in Organic Chemistry", Ocean Press, with partial English translation thereof, Dec. 2004, pp. 1-4.
"International Search Report (Form PCT/ISA/210) of PCT/JP2021/029869", mailed on Sep. 28, 2021, with English translation thereof, pp. 1-5.
"Written Opinion of the International Searching Authority (Form PCT/ISA/237) of PCT/JP2021/029869", mailed on Sep. 28, 2021, with English translation thereof, pp. 1-6.
"Office Action of China Counterpart Application", issued on Apr. 17, 2024, with English translation thereof, p. 1-p. 25.

* cited by examiner

POLYMERIZABLE COMPOSITION, POLYMER, ULTRAVIOLET SHIELDING MATERIAL, LAMINATE, COMPOUND, ULTRAVIOLET ABSORBING AGENT, AND METHOD OF PRODUCING COMPOUND

CROSS-REFERENCE TO RELATED APPLICATIONS

This application is a Continuation of PCT International Application No. PCT/JP2021/029869 filed on Aug. 16, 2021, which claims priority under 35 U.S.C § 119(a) to Japanese Patent Application No. 2020-140222 filed on Aug. 21, 2020 and Japanese Patent Application No. 2021-014078 filed on Feb. 1, 2021. Each of the above application(s) is hereby expressly incorporated by reference, in its entirety, into the present application.

BACKGROUND OF THE INVENTION

1. Field of the Invention

The present invention relates to a polymerizable composition. More specifically, the present invention relates to a polymerizable compound used for producing a polymer or the like having ultraviolet shielding properties. Further, the present invention also relates to a polymer, an ultraviolet shielding material, a laminate, a compound, an ultraviolet absorbing agent, and a method of producing a compound.

2. Description of the Related Art

An ultraviolet absorbing agent is widely used in applications for preventing deterioration of a resin. Further, in recent years, there has been an increasing demand for a resin for cutting a long wavelength region at around 400 nm.

Further, since it has been pointed out that ultraviolet rays have an effect on the skin (for example, causes of spots, freckles, wrinkles and sagging of the skin, and skin cancer), the ultraviolet absorbing agent is also used in applications such as cosmetics.

Further, attention has been paid to the influence on the retina caused by direct incidence of light having various wavelengths on human eyes, and there is a concern that particularly long-wavelength ultraviolet rays and blue light damage the retina and cause eye diseases. In a case of using a liquid crystal display device, an image display device such as an electroluminescent display, or a device including a display, for example, a small terminal such as a smartphone or a tablet terminal, a screen of a display including a light source is visually observed. In recent years, attention has been paid to the influence of ultraviolet rays on the retina in a case where an image display device, a small terminal, or the like is used for a long period of time.

Therefore, attempts have been made to reduce the influence of ultraviolet rays on the eyes of a user by providing ultraviolet shielding materials in the above-described devices and the like.

An ultraviolet absorbing agent is used for such an ultraviolet shielding material. A benzodithiol compound or the like is known as an example of the ultraviolet absorbing agent (Patent Literature 1 and Patent Literature 2).

CITATION LIST

Patent Literature

[Patent Literature 1] WO2019/131572A
[Patent Literature 2] JP2009-263617A

SUMMARY OF THE INVENTION

An ultraviolet absorbing agent is required to have high transparency to visible light and to be less colored. Further, in recent years, there is a demand for development of an ultraviolet absorbing agent having a high absorption ability with respect to ultraviolet rays having a long wavelength of approximately 400 nm.

In addition, the ultraviolet absorbing performance of an ultraviolet absorbing agent may be degraded with time due to irradiation with light. In particular, an ultraviolet absorbing agent having a maximum absorption wavelength on a longer wavelength side in an ultraviolet region has a tendency that the light resistance is poor and the absorption ability thereof is degraded with time.

Therefore, an object of the present invention is to provide a polymerizable composition capable of producing a polymer with excellent shielding properties against light having an approximately wavelength of 400 nm and excellent light resistance. Further, an object of the present invention is to provide a polymer, an ultraviolet shielding material, a laminate, a compound, an ultraviolet absorbing agent, and a method of producing a compound, with excellent shielding properties against light having an approximately wavelength of 400 nm and excellent light resistance.

The present invention provides the following aspects.

<1> A polymerizable composition comprising: a compound represented by Formula (1); and an ultraviolet absorbing agent A having a maximum absorption wavelength on a shorter wavelength side than a maximum absorption wavelength of the compound represented by Formula (1), (1)

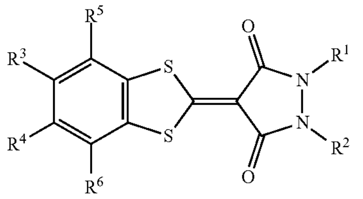

in Formula (1), $R^1$ to $R^6$ each independently represent a hydrogen atom or a substituent, $R^1$ and $R^2$ may be bonded to each other to form a ring, and $R^3$ and $R^4$ may be bonded to each other to form a ring, where at least one of $R^1$ to $R^6$ represents a group that contains a polymerizable group having an ethylenically unsaturated bond.

<2> The polymerizable composition according to <1>, in which the compound represented by Formula (1) is a compound represented by Formula (2), (2)

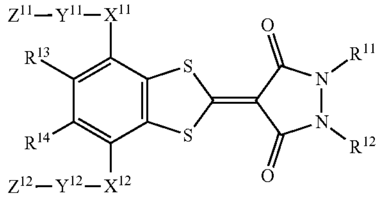

in Formula (2), $R^{11}$ and $R^{12}$ each independently represent a hydrogen atom, an alkyl group, or an aryl group, $R^{13}$ and $R^{14}$ each independently represent a hydrogen atom, a halogen atom, an alkyl group, an aryl group, an alkoxy group, or an aryloxy group, $X^{11}$ and $X^{12}$ each independently represent a single bond, —O—, —OC(═O)—, —OC(═O)O—, or —OC(═O)NRx$^{11}$-, where Rx$^{11}$ represents a hydrogen atom, an alkyl group, or an aryl group, $Y^{11}$ and $Y^{12}$ each independently represent a single bond or a divalent linking group, $Z^{11}$ and $Z^{12}$ each independently represent a hydrogen atom or a polymerizable group having an ethylenically unsaturated bond, $R^{11}$ and $R^{12}$ may be bonded to each other to form a ring, and $R^{13}$ and $R^{14}$ may be bonded to each other to form a ring, where at least one of $Z^{11}$ or $Z^{12}$ represents a polymerizable group having an ethylenically unsaturated bond.

<3> The polymerizable composition according to <1> or <2>, in which the polymerizable group having an ethylenically unsaturated bond is a (meth)acryloyloxy group or a vinylphenyl group.

<4> The polymerizable composition according to any one of <1> to <3>, in which the maximum absorption wavelength of the ultraviolet absorbing agent A is present in a wavelength range of 300 to 380 nm.

<5> The polymerizable composition according to any one of <1> to <4>, in which the ultraviolet absorbing agent A is a compound containing a polymerizable group.

<6> The polymerizable composition according to any one of <1> to <5>, in which the ultraviolet absorbing agent A is at least one selected from a 2-(2-hydroxyphenyl)benzotriazole-based compound, a 2-(2-hydroxyphenyl)-1,3,5-triazine-based compound, or a 2-hydroxybenzophenone-based compound.

<7> The polymerizable composition according to any one of <1> to <6>, further comprising: a polymerizable compound other than the compound represented by Formula (1); and a polymerization initiator.

<8> A polymer which is obtained by polymerizing the polymerizable composition according to any one of <1> to <7>.

<9> An ultraviolet shielding material comprising: the polymer according to <8>.

<10> A laminate comprising: a support; and the ultraviolet shielding material according to <9>.

<11> A compound which is represented by Formula (5), (5)

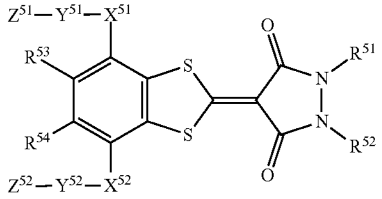

in Formula (5), $R^{51}$ and $R^{52}$ each independently represent a hydrogen atom, an alkyl group, or an aryl group, $R^{53}$ and $R^{54}$ each independently represent a hydrogen atom, a halogen atom, an alkyl group, an aryl group, an alkoxy group, or an aryloxy group, $X^{51}$ and $X^{52}$ each independently represent —O—, —OC(═O)O—, or —OC(═O)NH—, $Y^{51}$ and $Y^{52}$ each independently represent a single bond or a divalent linking group, the divalent linking group is a hydrocarbon group or a group having a structure in which two or more hydrocarbon groups are bonded via a linking group, and the linking group represents —O—, —C(═O)—, —OC(═O)—, —C(═O)O—, —NHC(═O)—, or —C(═O)NH—, and $Z^{51}$ and $Z^{52}$ each independently represent a hydrogen atom or a polymerizable group having an ethylenically unsaturated bond, where at least one of $Z^{51}$ or $Z^{52}$ represents a polymerizable group having an ethylenically unsaturated bond, in a case where $X^{51}$ represents —O—, the polymerizable group having an ethylenically unsaturated bond which is represented by $Z^{51}$ is a vinylphenyl group, and in a case where $X^{52}$ represents —O—, the polymerizable group having an ethylenically unsaturated bond which is represented by $Z^{52}$ is a vinylphenyl group.

<12> The compound according to <11>, in which the polymerizable group having an ethylenically unsaturated bond is a (meth)acryloyloxy group or a vinylphenyl group.

<13> The compound according to <11> or <12>, in which $X^{51}$ and $X^{52}$ each independently represent —O— or —OC(═O)NH—.

<14> The compound according to any one of <11> to <13>, in which $X^{51}$ has the same definition as that for $X^{52}$, $Y^{51}$ has the same definition as that for $Y^{52}$, and $Z^{51}$ has the same definition as that for $Z^{52}$.

<15> An ultraviolet absorbing agent comprising: the compound according to any one of <11> to <14>.

<16> A polymer which has a structure derived from the compound according to any one of <11> to <14>.

<17> A method of producing a compound, comprising: reacting a compound represented by Formula (6) with a compound represented by Formula (7) to produce a compound represented by Formula (5), (6)

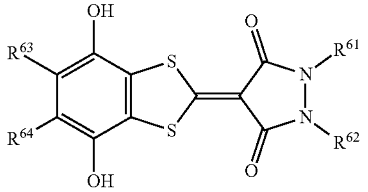

in Formula (6), $R^{61}$ and $R^{62}$ each independently represent a hydrogen atom, an alkyl group, or an aryl group, and $R^{63}$ and $R^{64}$ each independently represent a hydrogen atom, a halogen atom, an alkyl group, an aryl group, an alkoxy group, or an aryloxy group, $$Z^{71}—Y^{71}\text{-}E^{71} \quad (7)$$

in Formula (7), $E^{71}$ represents a group that reacts with a hydroxy group of Formula (6), $Y^{71}$ represents a single bond or a divalent linking group, the divalent linking group is a hydrocarbon group or a group having a structure in which two or more hydrocarbon groups are bonded via a linking group, and the linking group represents —O—, —C(═O)—, —OC(═O)—, —C(═O)O—, —NHC(═O)—, or —C(═O)NH—, and $Z^{71}$ represents a polymerizable group having an ethylenically unsaturated bond,

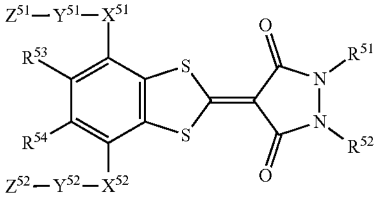
(5)

in Formula (5), $R^{51}$ and $R^{52}$ each independently represent a hydrogen atom, an alkyl group, or an aryl group, $R^{53}$ and $R^{54}$ each independently represent a hydrogen atom, a halogen atom, an alkyl group, an aryl group, an alkoxy group, or an aryloxy group, $X^{51}$ and $X^{52}$ each independently represent —O—, —OC(═O)O—, or —OC(═O)NH—, $Y^{51}$ and $Y^{52}$ each independently represent a single bond or a divalent linking group, the divalent linking group is a hydrocarbon group or a group having a structure in which two or more hydrocarbon groups are bonded via a linking group, and the linking group represents —O—, —C(═O)—, —OC(═O)—, —C(═O)O—, —NHC(═O)—, or —C(═O)NH—, and $Z^{51}$ and $Z^{52}$ each independently represent a hydrogen atom or a polymerizable group having an ethylenically unsaturated bond, where at least one of $Z^{51}$ or $Z^{52}$ represents a polymerizable group having an ethylenically unsaturated bond, in a case where $X^{51}$ represents —O—, the polymerizable group having an ethylenically unsaturated bond which is represented by $Z^{51}$ is a vinylphenyl group, and in a case where $X^{52}$ represents —O—, the polymerizable group having an ethylenically unsaturated bond which is represented by $Z^{52}$ is a vinylphenyl group.

<18> The method of producing a compound according to <17>, in which $E^{71}$ in Formula (7) represents —COCl, —O(C═O)Cl, —NCO, —Cl, —Br, —I, —$OSO_2D^1$, or an oxiranyl group, where $D^1$ represents a methyl group, an ethyl group, a phenyl group, or a 4-methylphenyl group.

According to the present invention, it is possible to provide a polymerizable composition capable of producing a polymer with excellent shielding properties against light having an approximately wavelength of 400 nm and excellent light resistance. Further, according to the present invention, it is possible to provide a polymer, an ultraviolet shielding material, a laminate, a compound, an ultraviolet absorbing agent, and a method of producing a compound, with excellent shielding properties against light having an approximately wavelength of 400 nm and excellent light resistance.

DESCRIPTION OF THE PREFERRED EMBODIMENTS

Hereinafter, the contents of the present invention will be described in detail.

In a case where substitution or unsubstitution is not specified in the notation of a group (atomic group) in the present specification, the group includes both a group which has no substituent and a group which has a substituent. For example, "alkyl group" includes not only an alkyl group having no substituent (unsubstituted alkyl group), but also an alkyl group having a substituent (substituted alkyl group).

In the present specification, a numerical range shown using "to" indicates a range including the numerical values described before and after "to" as the lower limit and the upper limit.

In the present specification, the total solid content denotes the total amount of components excluding solvents from all the components of the resin composition.

In the present specification, "(meth)acrylate" denotes both or any one of acrylate and methacrylate, "(meth)acryl" denotes both or any one of acryl and methacryl, "(meth) allyl" denotes both or any one of allyl and methallyl, and "(meth)acryloyl" denotes both or any one of acryloyl and methacryloyl.

In the present specification, the meaning of the term "step" includes not only an independent step but also a step whose intended purpose is achieved even in a case where the step is not clearly distinguished from other steps.

In the present specification, the weight-average molecular weight (Mw) and the number average molecular weight (Mn) are defined as values in terms of polystyrene, measured by gel permeation chromatography (GPC).

<Polymerizable Composition>

A polymerizable composition according to the embodiment of the present invention contains a compound represented by Formula (1), and an ultraviolet absorbing agent A having a maximum absorption wavelength on a shorter wavelength side than a maximum absorption wavelength of the compound represented by Formula (1).

Since the compound contained in the polymerizable composition according to the embodiment of the present invention and represented by Formula (1) is a compound which has excellent absorption ability with respect to light having a wavelength of approximately 400 nm and is less colored, a polymer which is less colored and has excellent shielding properties against light having a wavelength of approximately 400 nm can be produced by using the polymerizable composition according to the embodiment of the present invention. Further, the compound represented by Formula (1) contains a polymerizable group, and thus decomposition, modification, or the like of the compound represented by Formula (1) caused by irradiation with light can be suppressed due to incorporation into the polymer after polymerization. Therefore, as a result, a change with time in ultraviolet absorption ability derived from the compound represented by Formula (1) can be suppressed. Further, a change with time in ultraviolet absorption ability derived from the ultraviolet absorbing agent A can be suppressed by using a combination of the compound represented by Formula (1) and the ultraviolet absorbing agent A. Although the detailed reason is not clear, it is presumed that the above-described effects can be obtained by rapid deactivation of an excited state due to energy transfer from the ultraviolet absorbing agent A excited by light absorption to the compound represented by Formula (1).

Further, since the polymerizable composition according to the embodiment of the present invention contains the compound represented by Formula (1) and the ultraviolet absorbing agent A having a maximum absorption wavelength on a shorter wavelength side than the maximum absorption wavelength of the compound represented by Formula (1), a polymer capable of shielding ultraviolet rays in a wide wavelength range can also be produced.

Further, in the polymerizable composition according to the embodiment of the present invention, an ultraviolet shielding material such as a polymer in which bleed out or precipitation of an ultraviolet absorbing agent is suppressed can also be produced.

The polymerizable composition according to the embodiment of the present invention is a composition that can be polymerized by applying energy. Examples of a method of applying energy include irradiation with visible light, ultraviolet light, or an electron beam, and heating. Further, from the viewpoint of general-purpose properties and satisfactory polymerization sensitivity, irradiation with ultraviolet rays or heating is preferable.

Hereinafter, the polymerizable composition according to the embodiment of the present invention will be described in detail.

<<Compound Represented by Formula (1) (Compound (1))>>

The polymerizable according to the embodiment of the present invention contains a compound represented by Formula (1) (hereinafter, also referred to as a compound (1)). The compound (1) is preferably used as an ultraviolet absorbing agent.

(1)

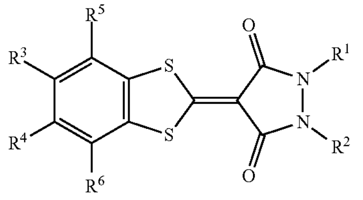

in Formula (1), $R^1$ to $R^6$ each independently represent a hydrogen atom or a substituent, $R^1$ and $R^2$ may be bonded to each other to form a ring, and $R^3$ and $R^4$ may be bonded to each other to form a ring, where at least one of $R^1$ to $R^6$ represents a group that contains a polymerizable group having an ethylenically unsaturated bond.

Examples of the substituent represented by $R^1$ to $R^6$ of Formula (1) include the following substituents and a group (T) including a polymerizable group having an ethylenically unsaturated bond. Examples of the polymerizable group having an ethylenically unsaturated bond include a vinyl group, a (meth)allyl group, a (meth)acryloyl group, a (meth) acryloyloxy group, a (meth)acryloylamino group, and a vinylphenyl group. Among these, a (meth)acryloyloxy group or a vinylphenyl group are preferable.

Examples of the group (T) including a polymerizable group having an ethylenically unsaturated bond include a group represented by Formula (T).

$$*\text{—}X^1\text{—}Y^1\text{—}Z^1 \quad (T)$$

In Formula (T), $X^1$ represents a single bond, —O—, —OC(═O)—, —OC(═O)O—, or —OC(═O)NRx$^1$-, and Rx$^1$ represents a hydrogen atom, an alkyl group, or an aryl group.

$Y^1$ represents a single bond or a divalent linking group.

$Z^1$ represents a polymerizable group having an ethylenically unsaturated bond.

As the alkyl group represented by Rx$^1$, an alkyl group having 1 to 30 carbon atoms is preferable. Specific examples thereof include a methyl group, an ethyl group, an n-propyl group, an isopropyl group, and an n-butyl. As the aryl group represented by Rx$^1$, a substituted or unsubstituted aryl group having 6 to 30 carbon atoms is preferable. Specific examples thereof include a phenyl group, a p-tolyl group, and a naphthyl group. It is preferable that Rx$^1$ represents a hydrogen atom.

$X^1$ represents preferably —O— or —OC(═O)NH— and more preferably —OC(═O)NH— from the viewpoint of synthesis.

Examples of the divalent linking group represented by $Y^1$ include a hydrocarbon group and a group in which two or more hydrocarbon groups are bonded to each other via a single bond or a linking group. Examples of the hydrocarbon group include an aliphatic hydrocarbon group and an aromatic hydrocarbon group, and an aliphatic hydrocarbon group is preferable. The number of carbon atoms of the aliphatic hydrocarbon group is preferably in a range of 1 to 30, more preferably in a range of 1 to 20, and still more preferably in a range of 1 to 15. The aliphatic hydrocarbon group may be linear, branched, or cyclic. Further, the cyclic aliphatic hydrocarbon group may be a monocycle or a fused ring. Further, the cyclic aliphatic hydrocarbon group may have a crosslinked structure. The number of carbon atoms of the aromatic hydrocarbon group is preferably in a range of 6 to 30, more preferably in a range of 6 to 20, and still more preferably in a range of 6 to 10. The hydrocarbon group may have a substituent. Examples of the substituent include the substituent T described below. Examples of the substituent include a hydroxy group.

Examples of the linking group that links two or more of the hydrocarbon groups include —NH—, —S(═O)$_2$—, —O—, —C(═O)—, —OC(═O)—, —C(═O)O—, —NHC(═O)—, and —C(═O)NH—. Among these, —O—, —C(═O)—, —OC(═O)—, —C(═O)O—, —NHC(═O)—, or —C(═O)NH— is preferable.

Examples of the polymerizable group having an ethylenically unsaturated bond represented by $Z^1$ include a vinyl group, an allyl group, a (meth)acryloyl group, a (meth) acryloyloxy group, a (meth)acryloylamino group, and a vinylphenyl group. Among these, a (meth)acryloyloxy group or a vinylphenyl group is preferable.

Specific examples of the group (T) including a polymerizable group having an ethylenically unsaturated bond include the following groups represented by T-1 to T-22. In the following structural formulae, Me represents a methyl group, and * represents a bonding site.

T-1

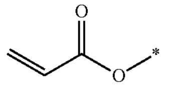

T-2

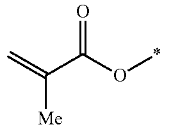

T-3

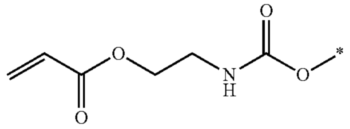

T-4

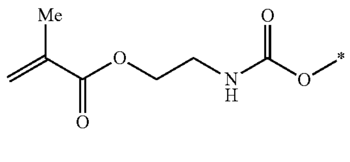

-continued

T-5

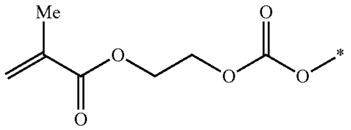

T-6

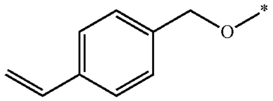

T-7

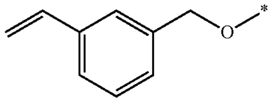

T-8

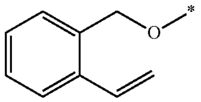

T-9

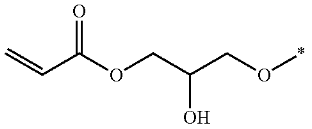

T-10

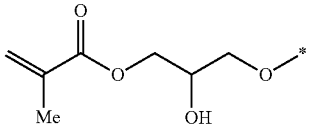

T-11

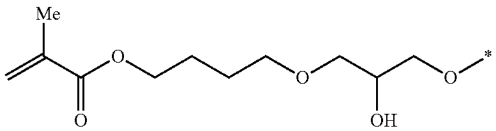

T-12

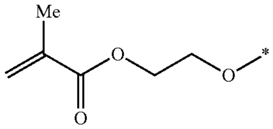

T-13

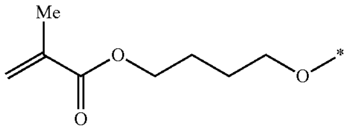

T-14

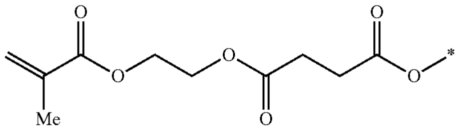

T-15

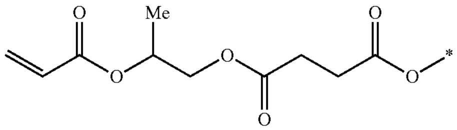

-continued

T-16

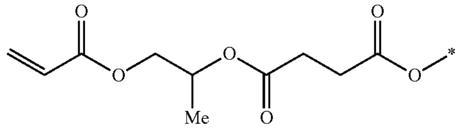

T-17

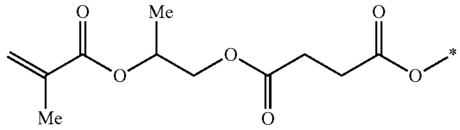

T-18

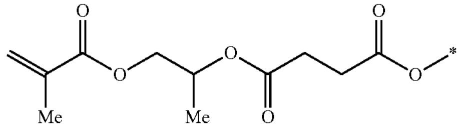

T-19

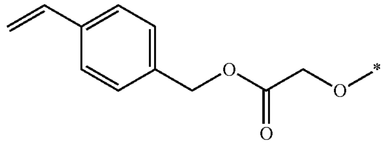

T-20

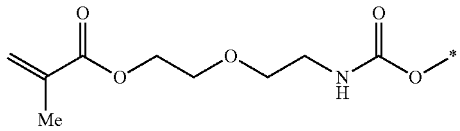

T-21

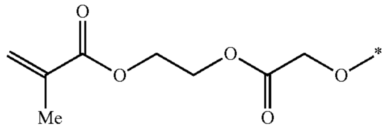

T-22

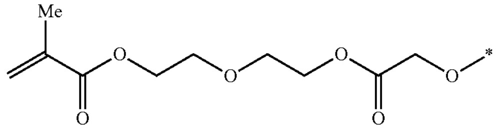

$R^1$ and $R^2$ of Formula (1) each independently represent preferably a hydrogen atom, an alkyl group, or an aryl group, more preferably an alkyl group or an aryl group, and still more preferably an alkyl group from the viewpoint that synthesis is relatively easily performed.

The number of carbon atoms of the alkyl group is preferably in a range of 1 to 30, more preferably in a range of 1 to 20, still more preferably in a range of 1 to 15, particularly preferably in a range of 1 to 10, and most preferably in a range of 1 to 8. The alkyl group may be linear, branched, or cyclic and preferably linear or branched. The alkyl group may have a substituent. Examples of the substituent include the groups described in the section of the substituent T below and the groups represented by Formula (T) described above.

The number of carbon atoms of the aryl group is preferably in a range of 6 to 40, more preferably in a range of 6 to 30, still more preferably in a range of 6 to 20, particularly preferably in a range of 6 to 15, and most preferably in a range of 6 to 12. As the aryl group, a phenyl group or a naphthyl group is preferable, and a phenyl group is more preferable. Further, the aryl group may have a substituent. Examples of the substituent include the groups described in the section of the substituent T below and the groups represented by Formula (T) described above.

$R^1$ and $R^2$ may be bonded to each other to form a ring. It is preferable that the ring formed by $R^1$ and $R^2$ being bonded to each other is a 5- or 6-membered ring. Specific examples of the ring formed by $R^1$ and $R^2$ being bonded to each other include a hexahydropyridazine ring, a tetrahydropyridazine ring, and a tetrahydrophthalazine ring. The ring formed by $R^1$ and $R^2$ being bonded to each other may have a substituent. Examples of the substituent include the groups described in the section of the substituent T below and the groups represented by Formula (T) described above.

$R^3$ and $R^4$ of Formula (1) each independently represent preferably a hydrogen atom, a halogen atom, an alkyl group, an aryl group, an alkoxy group, or an aryloxy group, more preferably a hydrogen atom, a halogen atom, or an alkyl group, and still more preferably a hydrogen atom or an alkyl group.

Examples of the halogen atom represented by $R^3$ and $R^4$ include a fluorine atom, a chlorine atom, a bromine atom, and an iodine atom. Among these, a fluorine atom or a chlorine atom is preferable.

The number of carbon atoms of the alkyl group represented by $R^3$ and $R^4$ is preferably in a range of 1 to 30, more preferably in a range of 1 to 20, still more preferably in a range of 1 to 15, particularly preferably in a range of 1 to 10, and most preferably in a range of 1 to 8. The alkyl group may be linear, branched, or cyclic and preferably linear or branched. The alkyl group may have a substituent. Examples of the substituent include the groups described in the section of the substituent T below and the groups represented by Formula (T) described above.

The number of carbon atoms of the aryl group represented by $R^3$ and $R^4$ is preferably in a range of 6 to 40, more preferably in a range of 6 to 30, still more preferably in a range of 6 to 20, particularly preferably in a range of 6 to 15, and most preferably in a range of 6 to 12. As the aryl group, a phenyl group or a naphthyl group is preferable, and a phenyl group is more preferable. Further, the aryl group may have a substituent. Examples of the substituent include the groups described in the section of the substituent T below and the groups represented by Formula (T) described above.

The number of carbon atoms of the alkoxy group represented by $R^3$ and $R^4$ is preferably in a range of 1 to 30, more preferably in a range of 1 to 20, still more preferably in a range of 1 to 15, particularly preferably in a range of 1 to 10, and most preferably in a range of 1 to 8. The alkoxy group may be linear or branched. The alkoxy group may have a substituent. Examples of the substituent include the groups described in the section of the substituent T below and the groups represented by Formula (T) described above.

The number of carbon atoms of the aryloxy group represented by $R^3$ and $R^4$ is preferably in a range of 6 to 40, more preferably in a range of 6 to 30, still more preferably in a range of 6 to 20, particularly preferably in a range of 6 to 15, and most preferably in a range of 6 to 12. The aryloxy group may have a substituent. Examples of the substituent include the groups described in the section of the substituent T below and the groups represented by Formula (T) described above.

In Formula (1), $R^3$ and $R^4$ may be bonded to each other to form a ring. It is preferable that the ring formed by these groups being bonded to each other is a 5- or 6-membered ring. Specific examples of the ring formed by $R^3$ and $R^4$ being bonded to each other include a cyclohexene ring and a benzene ring. The ring formed by $R^3$ and $R^4$ being bonded to each other may have a substituent. Examples of the substituent include the groups described in the section of the substituent T below and the groups represented by Formula (T) described above.

It is preferable that $R^5$ and $R^6$ of Formula (1) each independently represent a group represented by Formula (Ta).

$$*\!-\!X^{1a}\!-\!Y^{1a}\!-\!Z^{1a} \qquad \text{(Ta)}$$

In Formula (Ta), $X^{1a}$ represents a single bond, —O—, —OC(=O)—, —OC(=O)O—, or —OC(=O)NRx$^1$-, $Rx^1$ represents a hydrogen atom, an alkyl group, or an aryl group, $Y^{1a}$ represents a single bond or a divalent linking group, and $Z^{1a}$ represents a polymerizable group having a hydrogen atom or an ethylenically unsaturated bond.

$X^{1a}$ and $Y^{1a}$ of Formula (Ta) each have the same definition as that for $X^1$ and $Y^1$ of Formula (T). Examples of the polymerizable group having an ethylenically unsaturated bond represented by $Z^{1a}$ of Formula (Ta) include a vinyl group, an allyl group, a (meth)acryloyl group, a (meth)acryloyloxy group, a (meth)acryloylamino group, and a vinylphenyl group. Among these, a (meth)acryloyloxy group or a vinylphenyl group is preferable.

It is preferable that at least one of $R^5$ or $R^6$ of Formula (1) is a polymerizable group having an ethylenically unsaturated bond represented by $Z^{1a}$ of Formula (Ta). That is, it is preferable that at least one of $R^5$ or $R^6$ represents a group represented by Formula (T).

It is preferable that the compound represented by Formula (1) (compound (1)) is a compound represented by Formula (2). According to this aspect, a polymer having more excellent shielding properties against light having a wavelength of approximately 400 nm and more excellent light resistance can be produced.

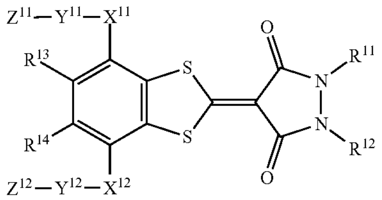

(2)

In Formula (2), $R^{11}$ and $R^{12}$ each independently represent a hydrogen atom, an alkyl group, or an aryl group, $R^{13}$ and $R^{14}$ each independently represent a hydrogen atom, a halogen atom, an alkyl group, an aryl group, an alkoxy group, or an aryloxy group, $X^{11}$ and $X^{12}$ each independently represent a single bond, —O—, —OC(=O)—, —OC(=O)O—, or —OC(=O)NRx$^{11}$-, where $Rx^{11}$ represents a hydrogen atom, an alkyl group, or an aryl group, $Y^{11}$ and $Y^{12}$ each independently represent a single bond or a divalent linking group, $Z^{11}$ and $Z^{12}$ each independently represent a hydrogen atom or a polymerizable group having an ethylenically unsaturated bond, $R^{11}$ and $R^{12}$ may be bonded to each other to form a ring, and $R^{13}$ and $R^{14}$ may be bonded to each other to form a ring, where at least one of $Z^{11}$ or $Z^{12}$ represents a polymerizable group having an ethylenically unsaturated bond.

The alkyl group and the aryl group represented by $R^{11}$ and $R^{12}$ of Formula (2) each have the same definition as that for the alkyl group and the aryl group represented by $R^1$ and $R^2$ of Formula (1). $R^{11}$ and $R^{12}$ of Formula (1) each independently represent preferably an alkyl group or an aryl group and more preferably an alkyl group. $R^{11}$ and $R^{12}$ of Formula (2) may be bonded to each other to form a ring. It is preferable that the ring formed by $R^{11}$ and $R^{12}$ being bonded to each other is a 5- or 6-membered ring. Specific examples of the ring formed by $R^{11}$ and $R^{12}$ being bonded to each other include a hexahydropyridazine ring, a tetrahydropyridazine ring, and a tetrahydrophthalazine ring. The ring formed by $R^{11}$ and $R^{12}$ being bonded to each other may have a substituent. Examples of the substituent include the groups described in the section of the substituent T below and the groups represented by Formula (T) described above.

The halogen atom, the alkyl group, the aryl group, the alkoxy group, and the aryloxy group represented by $R^{13}$ and $R^{14}$ of Formula (2) each have the same definition as that for the halogen atom, the alkyl group, the aryl group, the alkoxy group, and the aryloxy group represented by $R^3$ and $R^4$ of Formula (1). $R^{13}$ and $R^{14}$ of Formula (2) may be bonded to each other to form a ring. It is preferable that the ring formed by these groups being bonded to each other is a 5- or 6-membered ring. Specific examples of the ring formed by $R^{13}$ and $R^{14}$ being bonded to each other include a cyclohexene ring and a benzene ring. The ring formed by $R^{13}$ and $R^{14}$ being bonded to each other may have a substituent. Examples of the substituent include the groups described in the section of the substituent T below and the groups represented by Formula (T) described above.

$X^{11}$ and $X^{12}$ of Formula (2) each have the same definition as that for $X^1$ of Formula (T).

$Y^{11}$ and $Y^{12}$ of Formula (2) each have the same definition as that for $Y^1$ of Formula (T).

Examples of the polymerizable group having an ethylenically unsaturated bond represented by $Z^{11}$ and $Z^{12}$ of Formula (2) include a vinyl group, an allyl group, a (meth)acryloyl group, a (meth)acryloyloxy group, a (meth)acryloylamino group, and a vinylphenyl group. Among these, a (meth)acryloyloxy group or a vinylphenyl group is preferable.

In Formula (2), it is preferable that $X^{11}$ has the same definition as that for $X^{12}$, $Y^{11}$ has the same definition as that for $Y^{12}$, and $Z^{11}$ has the same definition as that for $Z^{12}$.

It is preferable that the compound represented by Formula (1) (compound (1)) is a compound represented by Formula (5). The compound represented by Formula (5) is the compound according to the embodiment of the present invention.

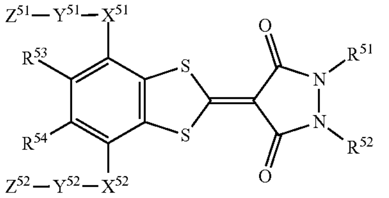

(5)

In Formula (5), $R^{51}$ and $R^{52}$ each independently represent a hydrogen atom, an alkyl group, or an aryl group, $R^{53}$ and $R^{54}$ each independently represent a hydrogen atom, a halogen atom, an alkyl group, an aryl group, an alkoxy group, or an aryloxy group, $X^{51}$ and $X^{52}$ each independently represent —O—, —OC(=O)O—, or —OC(=O)NH—, $Y^{51}$ and $Y^{52}$ each independently represent a single bond or a divalent linking group, the divalent linking group is a hydrocarbon group or a group having a structure in which two or more hydrocarbon groups are bonded via a linking group, and the linking group represents —O—, —C(=O)—, —OC(=O)—, —C(=O)O—, —NHC(=O)—, or —C(=O)NH—, $Z^{51}$ and $Z^{52}$ each independently represent a hydrogen atom or a polymerizable group having an ethylenically unsaturated bond, where at least one of $Z^{51}$ or $Z^{52}$ represents a polymerizable group having an ethylenically unsaturated bond, in a case where $X^{51}$ represents-O—, the polymerizable group having an ethylenically unsaturated bond which is represented by $Z^{51}$ is a vinylphenyl group, and in a case where $X^{52}$ represents —O—, the polymerizable group having an ethylenically unsaturated bond which is represented by $Z^{52}$ is a vinylphenyl group.

The alkyl group and the aryl group represented by $R^{51}$ and $R^{52}$ of Formula (5) each have the same definition as that for the alkyl group and the aryl group represented by $R^1$ and $R^2$ of Formula (1).

The halogen atom, the alkyl group, the aryl group, the alkoxy group, and the aryloxy group represented by $R^{53}$ and $R^{54}$ of Formula (5) each have the same definition as that for the halogen atom, the alkyl group, the aryl group, the alkoxy group, and the aryloxy group represented by $R^3$ and $R^4$ of Formula (1).

$X^{51}$ and $X^{52}$ each independently represent —O—, —OC(=O)O—, or —OC(=O)NH—, preferably —O— or —OC(=O)NH—, and more preferably —OC(=O)NH—.

$Y^{51}$ and $Y^{52}$ each independently represent a single bond or a divalent linking group, the divalent linking group is a hydrocarbon group or a group having a structure in which two or more hydrocarbon groups are bonded via a linking group, and the linking group represents —O—, —C(=O)—, —OC(=O)—, —C(=O)O—, —NHC(=O)—, or —C(=O)NH—.

Examples of the hydrocarbon group as $Y^{51}$ and $Y^{52}$ include an aliphatic hydrocarbon group and an aromatic hydrocarbon group, and an aliphatic hydrocarbon group is preferable. The number of carbon atoms of the aliphatic hydrocarbon group is preferably in a range of 1 to 30, more preferably in a range of 1 to 20, and still more preferably in a range of 1 to 15. The aliphatic hydrocarbon group may be linear, branched, or cyclic. Further, the cyclic aliphatic hydrocarbon group may be a monocycle or a fused ring. Further, the cyclic aliphatic hydrocarbon group may have a crosslinked structure. The number of carbon atoms of the aromatic hydrocarbon group is preferably in a range of 6 to 30, more preferably in a range of 6 to 20, and still more preferably in a range of 6 to 10. The hydrocarbon group may have a substituent. Examples of the substituent include the substituent T described below. Examples of the substituent include a hydroxy group. The linking group that links two or more of the hydrocarbon groups is-O—, —C(=O)—, —OC(=O)—, —C(=O)O—, —NHC(=O)—, or —C(=O)NH—.

Examples of the polymerizable group having an ethylenically unsaturated bond represented by $Z^{51}$ and $Z^{52}$ include a vinyl group, an allyl group, a (meth)acryloyl group, a (meth)acryloyloxy group, a (meth)acryloylamino group, and a vinylphenyl group. Among these, a (meth)acryloyloxy group or a vinylphenyl group is preferable.

In Formula (5), it is preferable that $X^{51}$ has the same definition as that for $X^{52}$, $Y^{51}$ has the same definition as that for $Y^{52}$, and $Z^{51}$ has the same definition as that for $Z^{52}$.

(Substituent T)

Examples of the substituent T include the following groups.

Examples thereof include a halogen atom (such as a fluorine atom, a chlorine atom, a bromine atom, or an iodine atom), an alkyl group [a linear, branched, or cyclic alkyl group, specific examples thereof include a linear or branched alkyl group (preferably a linear or branched alkyl group having 1 to 30 carbon atoms, and examples thereof include a methyl group, an ethyl group, an n-propyl group, an isopropyl group, a t-butyl group, an n-octyl group, an eicosyl group, a 2-chloroethyl group, a 2-cyanoethyl group, and a 2-ethylhexyl group), a cycloalkyl group (preferably a cycloalkyl group having 3 to 30 carbon atoms, and examples thereof include a cyclohexyl group, a cyclopentyl group, and a 4-n-dodecylcyclohexyl group), a bicycloalkyl group (preferably a bicycloalkyl group having 5 to 30 carbon atoms, that is, a monovalent group obtained by removing one hydrogen atom from a bicycloalkane having 5 to 30 carbon atoms, and examples thereof include a bicyclo[1,2,2]heptane-2-yl group and a bicyclo[2,2,2]octane-3-yl group), and those having a tricyclo structure with a plurality of ring structures, and alkyl groups in the substituents described below (for example, an alkyl group in an alkylthio group) are alkyl groups of such a concept], an alkenyl group [linear, branched, or cyclic alkenyl group, specific examples thereof include a linear or branched alkenyl group (preferably a linear or branched alkenyl group having 2 to 30 carbon atoms, and examples thereof include a vinyl group, an allyl group, a prenyl group, a geranyl group, and an oleyl group), a cycloalkenyl group (preferably a cycloalkenyl group having 3 to 30 carbon atoms, that is, a monovalent group obtained by removing one hydrogen atom from a cycloalkene having 3 to 30 carbon atoms, and examples thereof include a 2-cyclopentene-1-yl group and a 2-cyclohexene-1-yl group), and a bicycloalkenyl group (preferably a bicycloalkenyl group having 5 to 30 carbon atoms, that is, a monovalent group obtained by removing one hydrogen atom from a bicycloalkene having one double bond, and examples thereof include a bicyclo[2,2,1]hepto-2-en-1-yl group and a bicyclo[2,2,2]octo-2-en-4-yl group)], an alkynyl group (preferably a linear or branched alkynyl group having 2 to 30 carbon atoms, examples thereof include an ethynyl group and a propargyl group), an aryl group (preferably an aryl group having 6 to 30 carbon atoms, examples thereof include a phenyl group, a p-tolyl group, a naphthyl group, an m-chlorophenyl group, an o-hexadecanoylaminophenyl group), a heterocyclic group (preferably a monovalent group obtained by removing one hydrogen atom from a 5- or 6-membered aromatic or non-aromatic heterocyclic compound and more preferably a 5- or 6-membered aromatic heterocyclic group having 3 to 30 carbon atoms, and examples thereof include a 2-furyl group, a 2-thienyl group, a 2-pyrimidinyl group, and a 2-benzothiazolyl group), a cyano group, a hydroxy group, a nitro group, a carboxyl group, an alkoxy group (preferably a linear or branched alkoxy group having 1 to 30 carbon atoms, and examples thereof include a methoxy group, an ethoxy group, an isopropoxy group, a t-butoxy group, an n-octyloxy group, and a 2-methoxyethoxy group), an aryloxy group (preferably an aryloxy group having 6 to 30 carbon atoms, and examples thereof include a phenoxy group, a 2-methylphenoxy group, a 4-t-butylphenoxy group, a 3-nitrophenoxy group, and a 2-tetradecanoylaminophenoxy group), a heterocyclic oxy group (preferably a heterocyclic oxy group having 2 to 30 carbon atoms, and examples thereof include a 1-phenyltetrazole-5-oxy group and a 2-tetrahydropyranyloxy group), an acyloxy group (preferably a formyloxy group, an alkylcarbonyloxy group having 2 to 30 carbon atoms, or an arylcarbonyloxy group having 6 to 30 carbon atoms, and examples thereof include a formyloxy group, an acetyloxy group, a pivaloyloxy group, a stearoyloxy group, a benzoyloxy group, and a p-methoxyphenylcarbonyloxy group), a carbamoyloxy group (preferably a carbamoyloxy group having 1 to 30 carbon atoms, and examples thereof include a N,N-dimethylcarbamoyloxy group, a N,N-diethylcarbamoyloxy group, a morpholinocarbonyloxy group, a N,N-di-n-octylaminocarbonyloxy group, and a N-n-octylcarbamoyloxy group), an alkoxycarbonyloxy group (preferably an alkoxycarbonyloxy group having 2 to 30 carbon atoms, and examples thereof include a methoxycarbonyloxy group, an ethoxycarbonyloxy group, a t-butoxycarbonyloxy group, and an n-octylcarbonyloxy group), an aryloxycarbonyloxy group (preferably an aryloxycarbonyloxy group having 7 to 30 carbon atoms, and examples thereof include a phenoxycarbonyloxy group, a p-methoxyphenoxycarbonyloxy group, and a p-n-hexadecyloxyphenoxycarbonyloxy group), an amino group (preferably an amino group, an alkylamino group having 1 to 30 carbon atoms, or an anilino group having 6 to 30 carbon atoms, and examples thereof include an amino group, a methylamino group, a dimethylamino group, an anilino group, a N-methyl-anilino group, and a diphenylamino group), an acylamino group (preferably a formylamino group, an alkylcarbonylamino group having 2 to 30 carbon atoms, or an arylcarbonylamino group having 6 to 30 carbon atoms, and examples thereof include a formylamino group, an acetylamino group, a pivaloylamino group, a lauroylamino group, a benzoylamino group, and a 3,4,5-tri-n-octyloxyphenylcarbonylamino group), an aminocarbonylamino group (preferably an aminocarbonylamino group having 1 to 30 carbon atoms, and examples thereof include a carbamoylamino group, a N,N-dimethylaminocarbonylamino group, a N,N-diethylaminocarbonylamino group, and a morpholinocarbonylamino group), an alkoxycarbonylamino group (preferably an alkoxycarbonylamino group having 2 to 30 carbon atoms, and examples thereof include a methoxycarbonylamino group, an ethoxycarbonylamino group, a t-butoxycarbonylamino group, an n-octadecyloxycarbonylamino group, and a N-methylmethoxycarbonylamino group), an aryloxycarbonylamino group (preferably an aryloxycarbonylamino group having 7 to 30 carbon atoms, and examples thereof include a phenoxycarbonylamino group, a p-chlorophenoxycarbonylamino group, and an m-n-octyloxyphenoxycarbonylamino group), a sulfamoylamino group (preferably a sulfamoylamino group having 0 to 30 carbon atoms, and examples thereof include a sulfamoylamino group, a N,N-dimethylaminosulfonylamino group, and a N-n-octylaminosulfonylamino group), an alkyl or aryl sulfonylamino group (preferably an alkyl sulfonylamino group having 1 to 30 carbon atoms or an aryl sulfonylamino group having 6 to 30 carbon atoms, and examples thereof include a methylsulfonylamino group, a butylsulfonylamino group, a phenylsulfonylamino group, a 2,3,5-trichlorophenylsulfonylamino group, and a p-methylphenylsulfonylamino group), a mercapto group, an alkylthio group (preferably an alkylthio group having 1 to 30 carbon atoms, and examples thereof include a methylthio group, an ethylthio group, and an n-hexadecylthio group), an arylthio group (preferably an arylthio group having 6 to 30 carbon atoms, and examples thereof include a phenylthio group, a p-chlorophenylthio group, and an m-methoxyphenylthio group), a heterocyclic thio group (preferably a heterocyclic thio group having 2 to 30 carbon atoms, and examples thereof include a 2-benzothiazolylthio group and a 1-phenyltetrazole-5-ylthio group), a sulfamoyl group (preferably a sulfamoyl group having 0 to 30 carbon atoms, and examples thereof include a N-ethylsulfamoyl group, a N-(3-dodecyloxypropyl) sulfamoyl group, a N,N-dimethylsulfamoyl group, a N-acetylsulfamoyl group, a N-benzoylsulfamoyl group, a N—(N'-phenylcarbamoyl) sulfamoyl group), a sulfo group, an alkyl or aryl sulfinyl group (preferably an alkyl sulfinyl group having 1 to 30 carbon atoms or an aryl sulfinyl group having 6 to 30 carbon atoms, and examples thereof include a methylsulfinyl group, an ethylsulfinyl group, a phenylsulfinyl group, and a p-methylphenylsulfinyl group), an alkyl or aryl sulfonyl group (preferably an alkyl sulfonyl group having 1 to 30 carbon atoms or an aryl sulfonyl group having 6 to 30 carbon atoms, and examples thereof include a methylsulfonyl group, an ethylsulfonyl group, a phenylsulfonyl group, and a p-methylphenylsulfonyl group), an acyl group (preferably a formyl group, an alkylcarbonyl group having 2 to 30 carbon atoms, an arylcarbonyl group having 7 to 30 carbon atoms, or a heterocyclic carbonyl group having 4 to 30 carbon atoms and bonded to a carbonyl group, and examples include an acetyl group, a pivaloyl group, a 2-chloroacetyl group, a stearoyl group, a benzoyl group, a p-n-octyloxyphenylcarbonyl group, a 2-pyridylcarbonyl group, and a 2-furylcarbonyl group), an aryloxycarbonyl group (preferably an aryloxycarbonyl group having 7 to 30 carbon atoms, and examples thereof include a phenoxycarbonyl group, an o-chlorophenoxycarbonyl group, an m-nitrophenoxycarbonyl group, and a p-t-butylphenoxycarbonyl group), an alkoxycarbonyl group (preferably an alkoxycarbonyl group having 2 to 30 carbon atoms, and examples thereof include a methoxycarbonyl group, an ethoxycarbonyl group, a t-butoxycarbonyl group, and an n-octadecyloxycarbonyl group), a carbamoyl group (preferably a carbamoyl group having 1 to 30 carbon atoms, and examples thereof include a carbamoyl group, a N-methylcarbamoyl group, a N,N-dimethylcarbamoyl group, a N,N-di-n-octylcarbamoyl group, and a N-(methylsulfonyl) carbamoyl group), an aryl or heterocyclic azo group (preferably an arylazo group having 6 to 30 carbon atoms or a heterocyclic azo group having 3 to 30 carbon atoms, and examples thereof include a phenylazo group, a p-chlorophenylazo group, and a 5-ethylthio-1,3,4-thiadiazole-2-ylazo group), an imide group (preferably a N-succinimide group or a N-phthalimide group), a phosphino group (preferably a phosphino group having 2 to 30 carbon atoms, and examples thereof include a dimethylphosphino group, a diphenylphosphino group, and a methylphenoxyphosphino group), a phosphinyl group (preferably a phosphinyl group having 2 to 30 carbon atoms, and examples thereof include a phosphinyl group, a dioctyloxyphosphinyl group, and a diethoxyphosphinyl group), a phosphinyloxy group (preferably a phosphinyloxy group having 2 to 30 carbon atoms, and examples thereof include a diphenoxyphosphinyloxy group and a dioctyloxyphosphinyloxy group), and a phosphinylamino group (preferably a phosphinylamino group having 2 to 30 carbon atoms, and thereof include a dimethoxyphosphinylamino group and a examples dimethylaminophosphinylamino group).

Among the groups described above, one or more hydrogen atoms of groups having hydrogen atoms may be substituted with the above-described substituents T. Examples of such substituents include an alkylcarbonylaminosulfonyl group, an arylcarbonylaminosulfonyl group, an alkylsulfonylaminocarbonyl group, and an arylsulfonylaminocarbonyl group. Specific examples include a methylsulfonylaminocarbonyl group, a p-methylphenylsulfonylaminocarbonyl group, an acetylaminosulfonyl group, and a benzoylaminosulfonyl group.

Specific examples of the compound (1) are shown below. In the following formulae, Formulae 1-1 to 24, 1-41 to 1-45, 1-48, 1-49, 1-50, 1-52 to 1-56, 1-59, and 1-60 are specific examples of the compound represented by Formula (5). In the structural formulae shown below, Me represents a methyl group, and tBu represents a tert-butyl group.

1-1

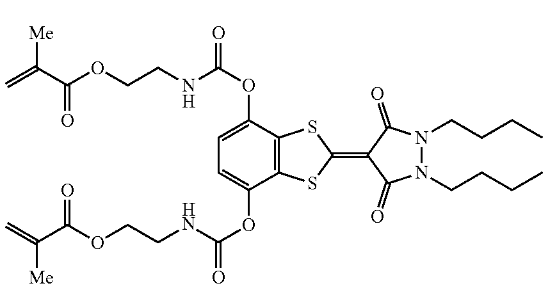

1-2

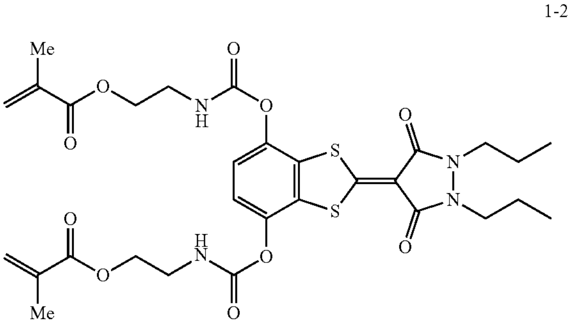

-continued
1-3
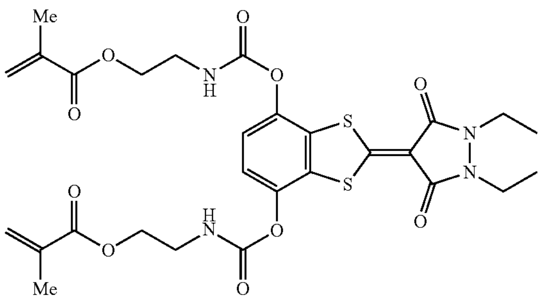
1-4
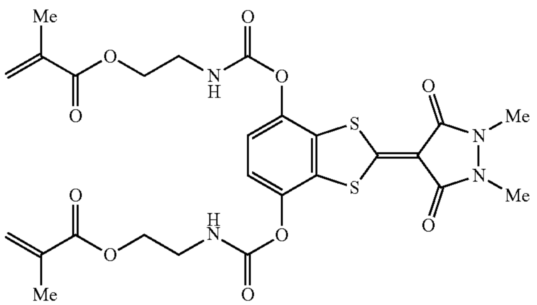
1-5
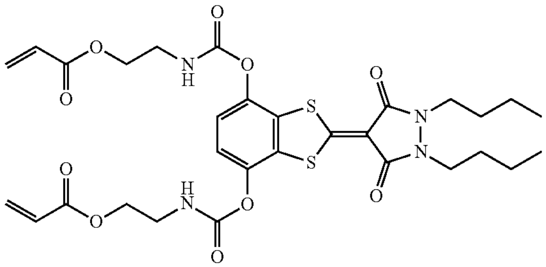
1-6
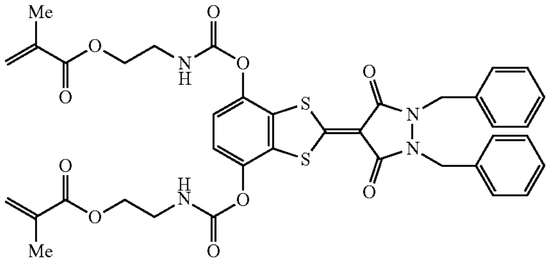
1-7
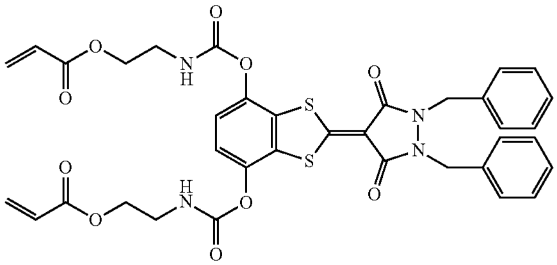
1-8
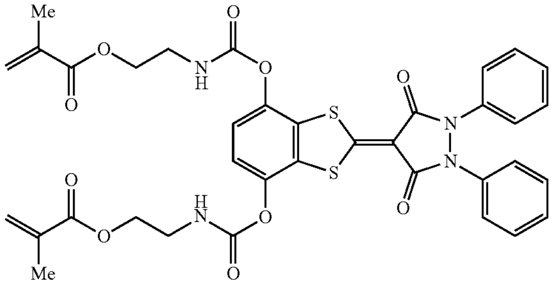
1-9
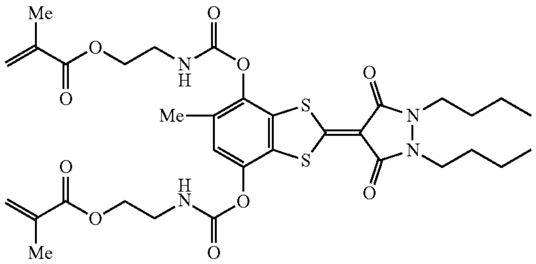
1-10
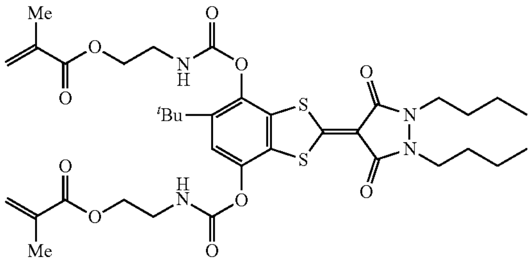
1-11
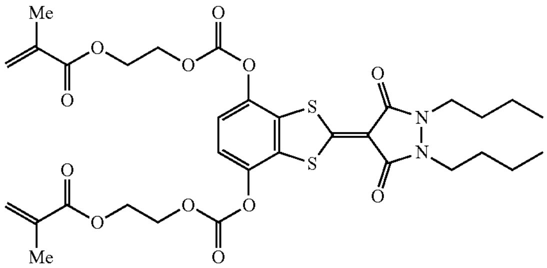
1-12
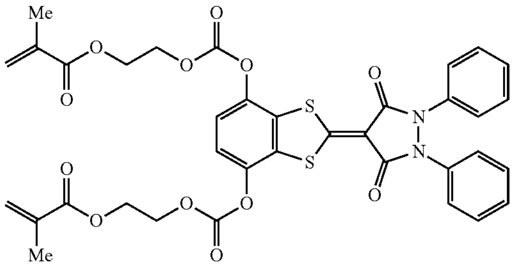

-continued
1-13
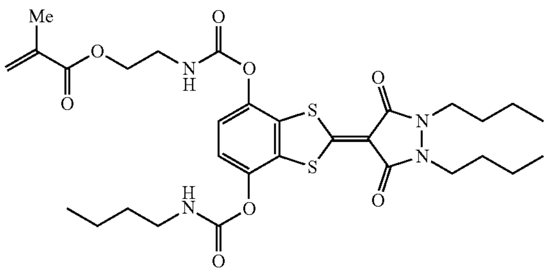
1-14
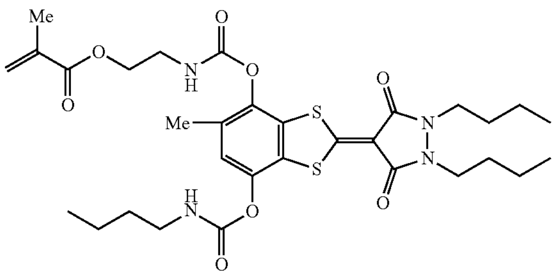
1-15
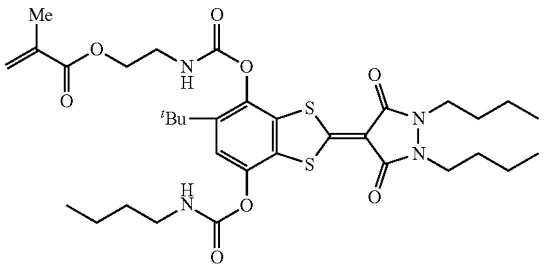
1-16
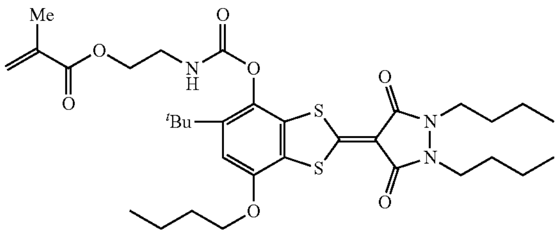
1-17
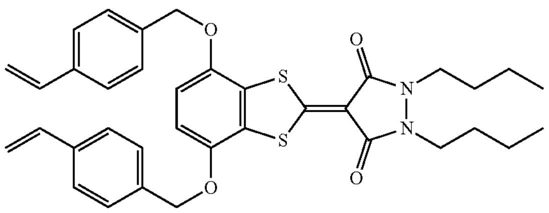
1-18
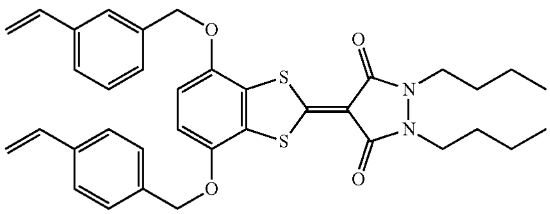
1-19
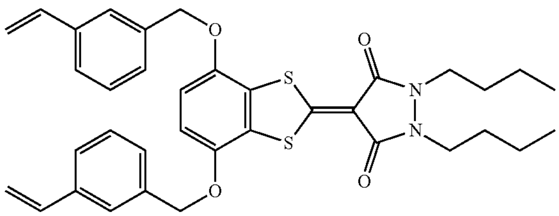
1-20
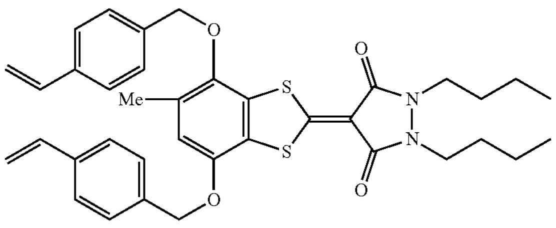
1-21
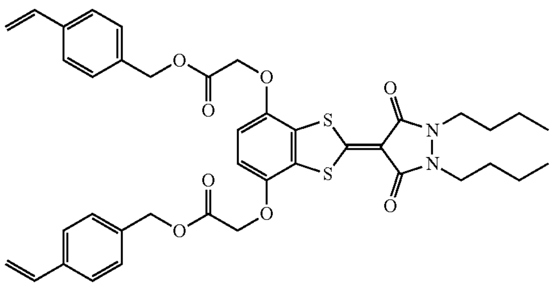
1-22
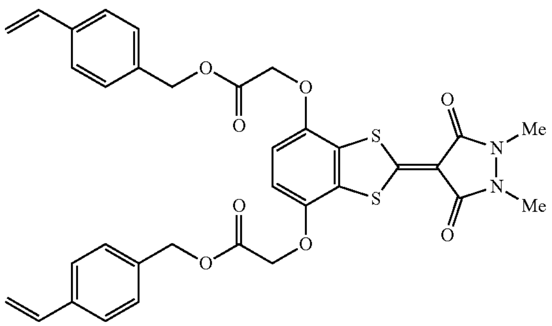

-continued
1-23
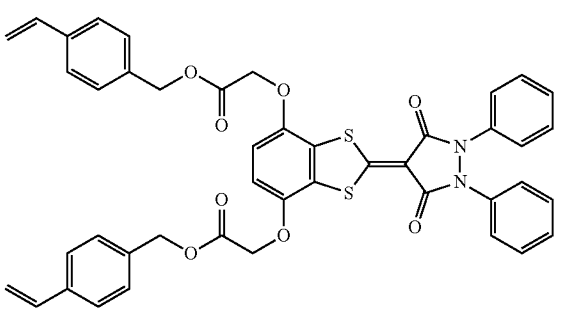
1-24
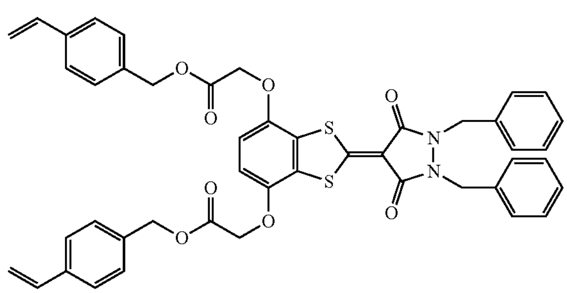
1-25
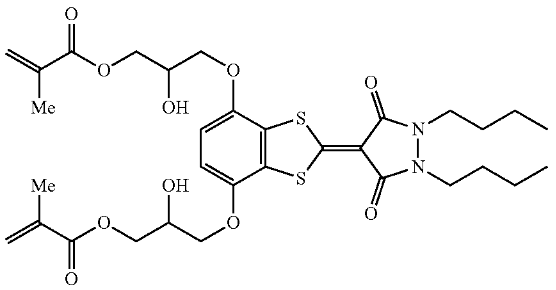
1-26
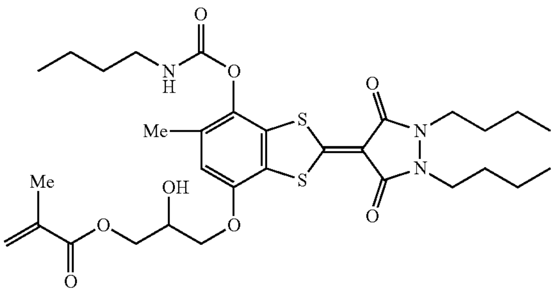
1-27
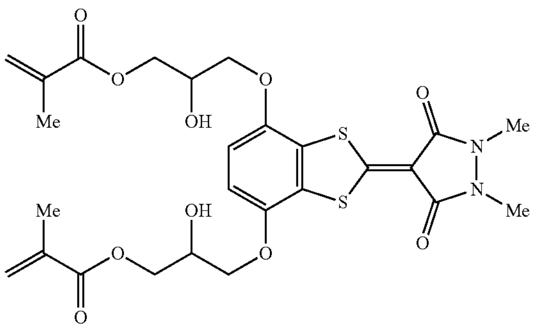
1-28
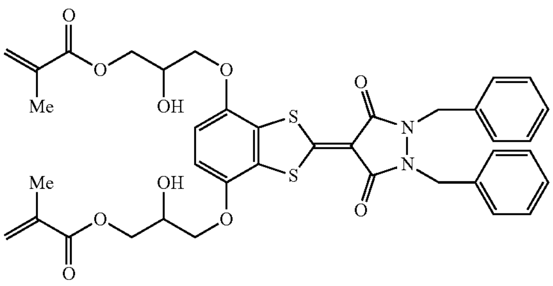
1-29
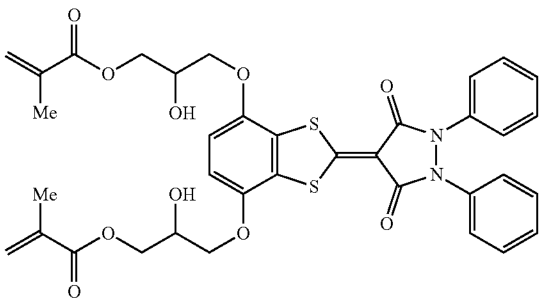
1-30
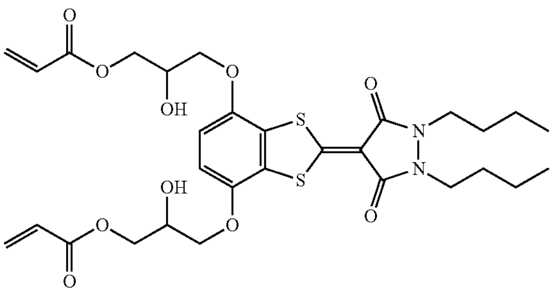
1-31
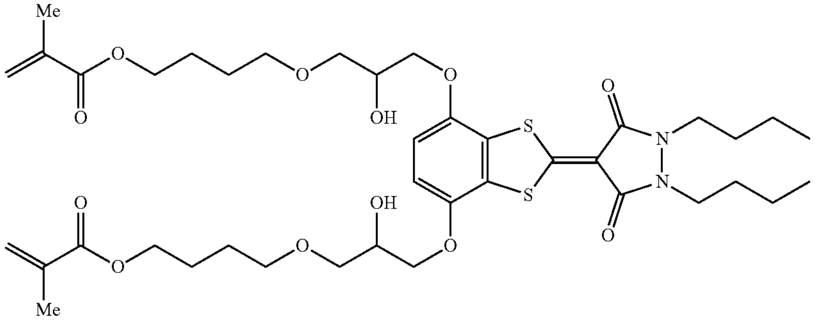

-continued
1-32
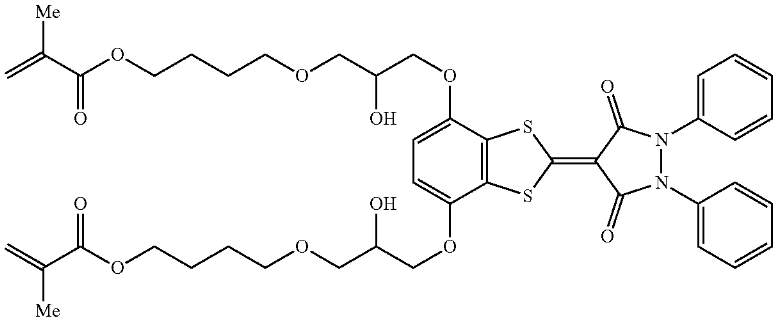
1-33
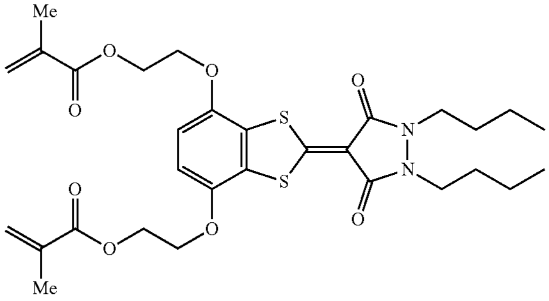
1-34
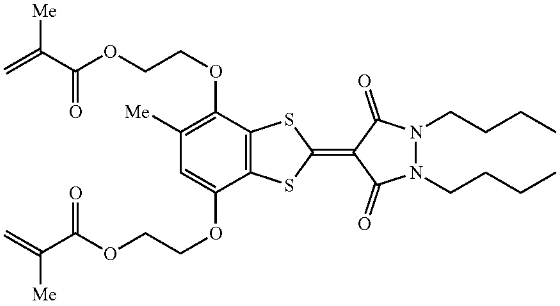
1-35
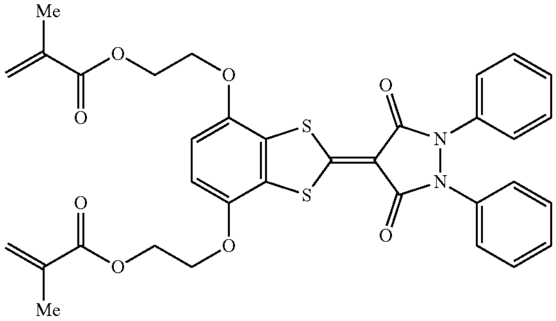
1-36
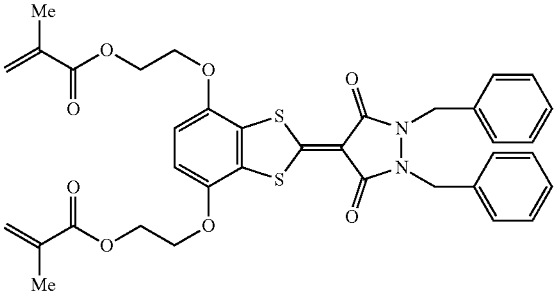
1-37
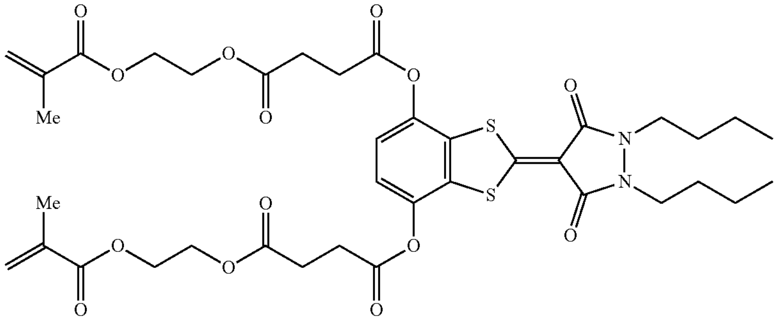
1-38
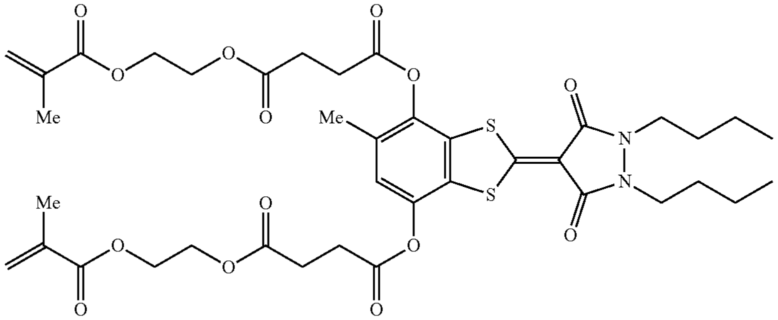

-continued
1-39
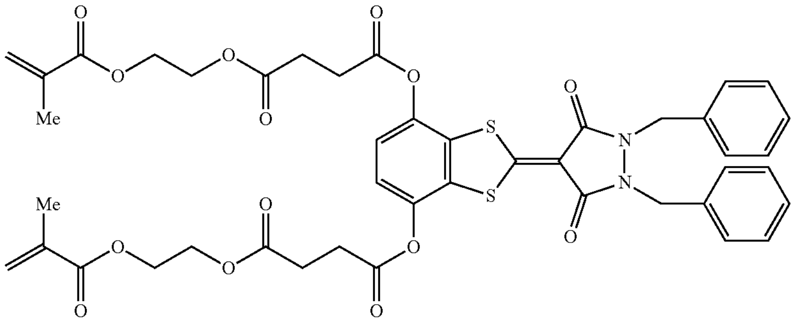
1-40
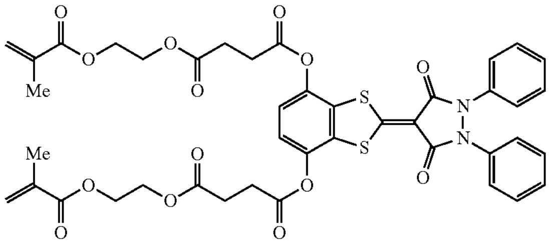
1-41
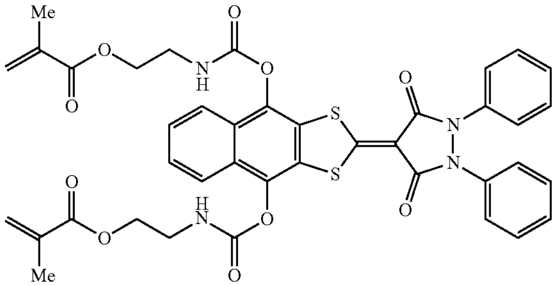
1-42
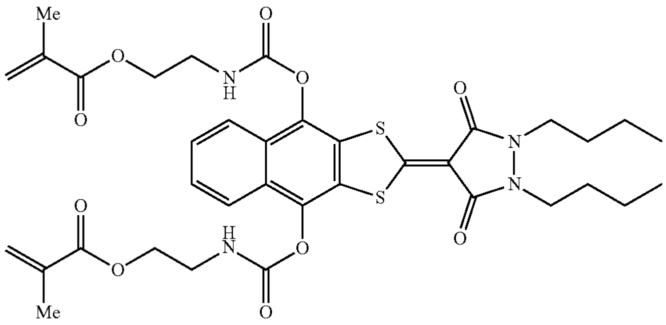
1-43
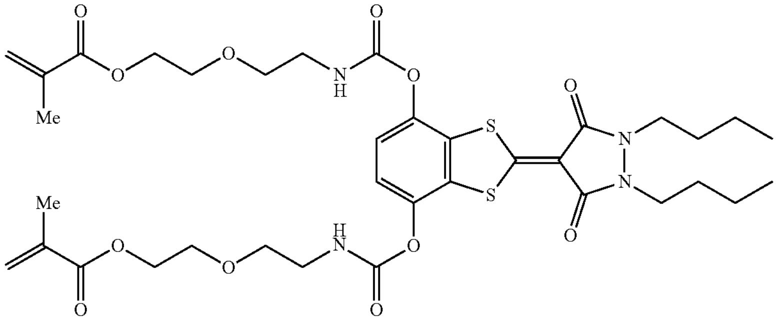
1-44
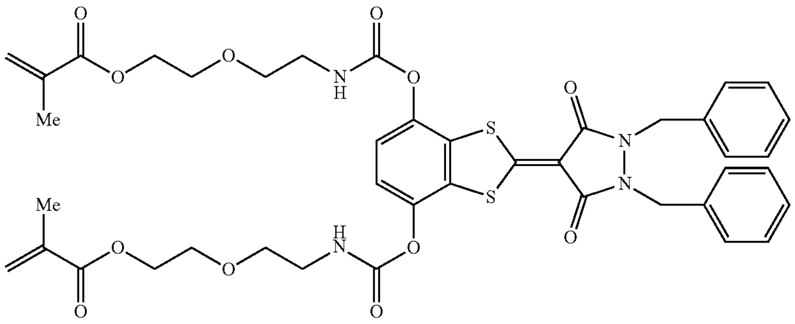

-continued
1-45
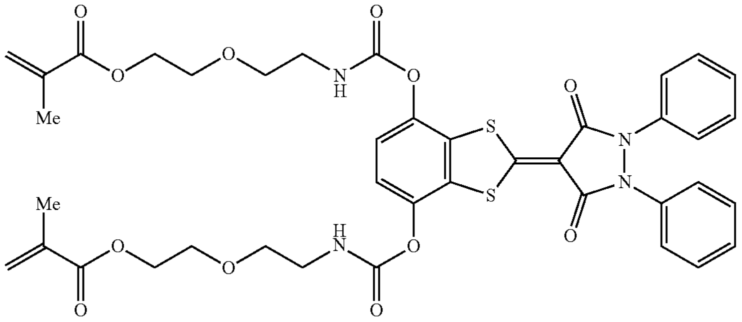
1-46
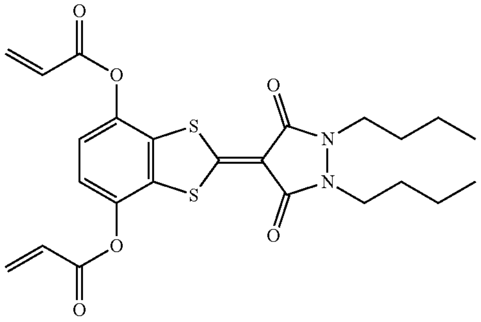
1-47
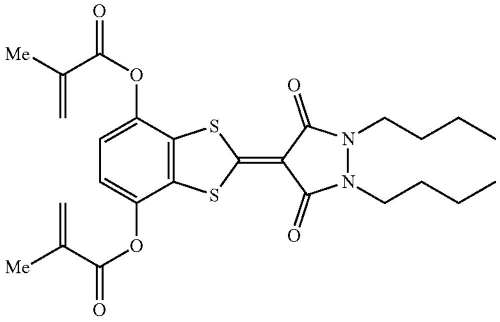
1-48
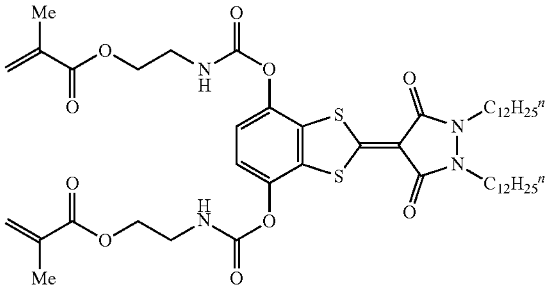
1-49
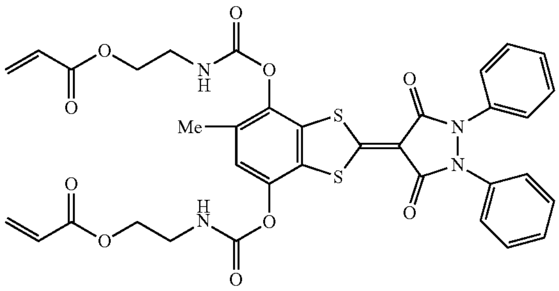
1-50
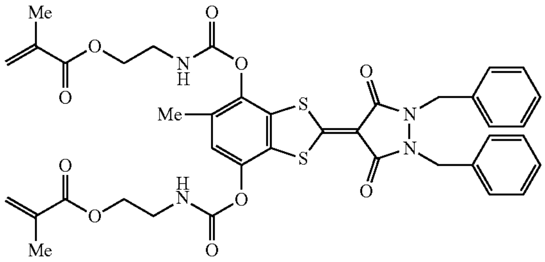
1-51
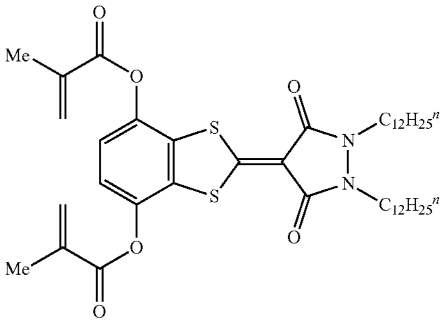
1-52
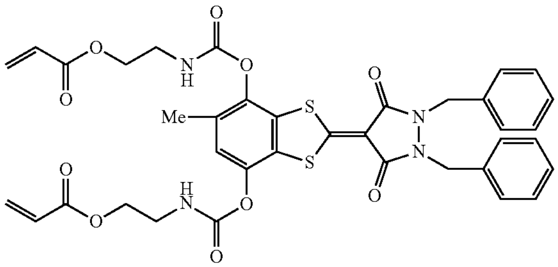
1-53
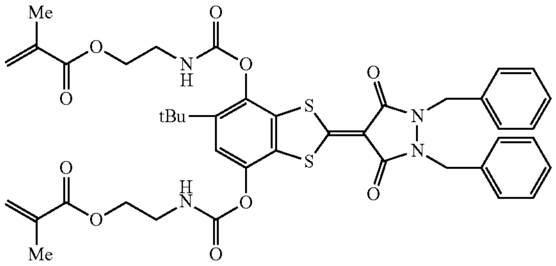

-continued
1-54
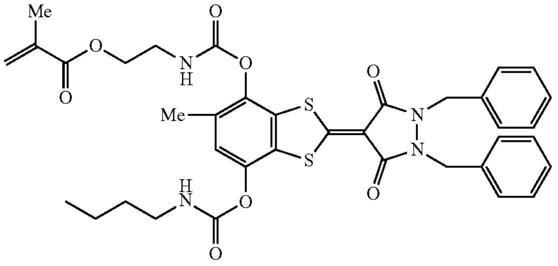
1-55
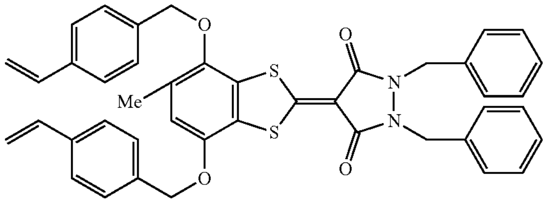
1-56
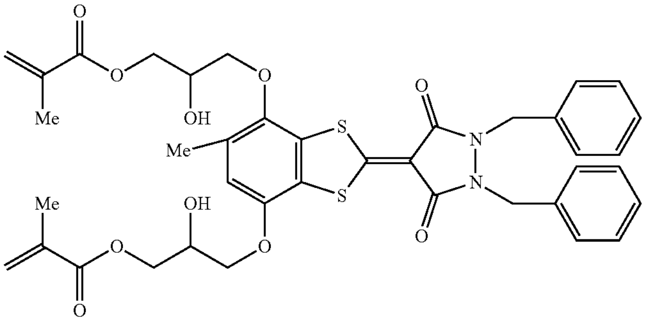
1-57
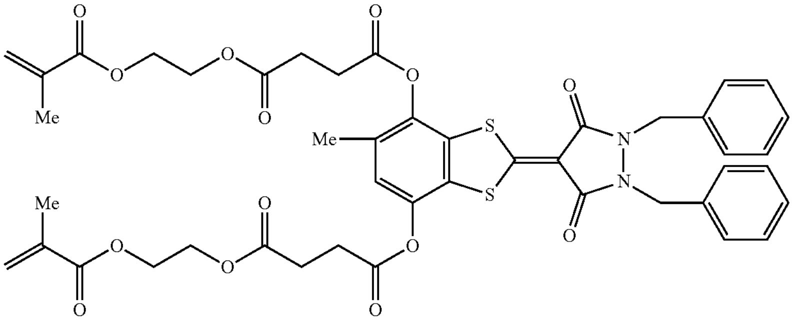
1-58
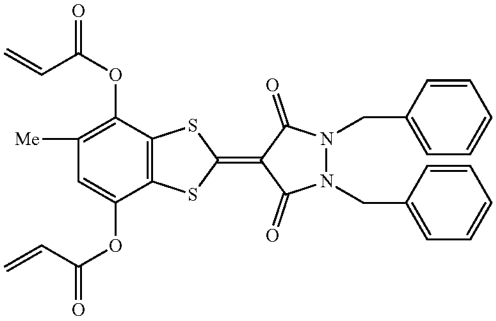
1-59
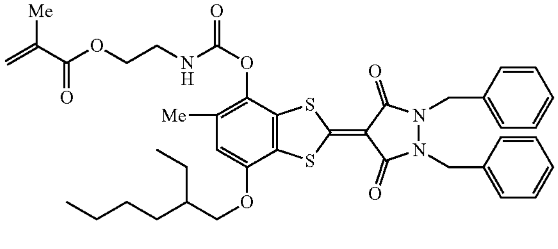
1-60
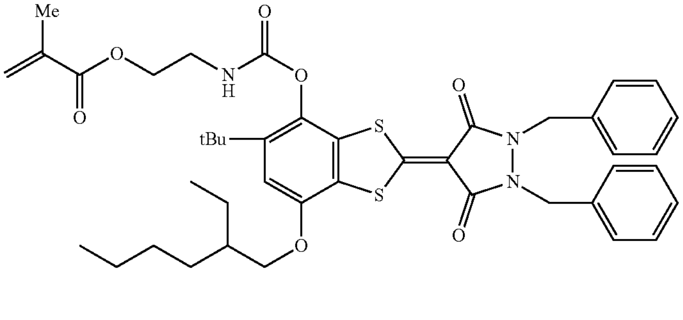

The maximum absorption wavelength of the compound (1) is present preferably in a wavelength range of 360 to 400 nm and more preferably in a wavelength range of 360 to 390 nm.

The molar absorption coefficient of the compound (1) at the maximum absorption wavelength is preferably 10,000 L/mol·cm or greater, more preferably 20,000 L/mol·cm or greater, and particularly preferably 30,000 L/mol·cm or greater.

Further, the molar absorption coefficient thereof at a wavelength of 400 nm is preferably 1,000 L/mol·cm or greater, more preferably 3,000 L/mol·cm or greater, and particularly preferably 5,000 L/mol·cm or greater.

Further, the molar absorption coefficient thereof at a wavelength of 420 nm is preferably 3,000 L/mol·cm or less, more preferably 2,000 L/mol cm or less, still more preferably 1,000 L/mol·cm or less, even still more preferably 500 L/mol·cm or less, and particularly preferably 100 L/mol·cm or less. A compound having a small molar absorption coefficient thereof at a wavelength of 420 nm is extremely less colored.

The maximum absorption wavelength and the molar absorption coefficient of the compound (1) can be acquired by measuring the spectral spectrum of a 0.005 mass % solution prepared by dissolving the compound (1) in ethyl acetate, at room temperature (25° C.) using a 1 cm quartz cell. Examples of the measuring device include UV-1800 (manufactured by Shimadzu Corporation).

The compound (1) can be produced in conformity with the method described in JP5376885B.

Further, the compound represented by Formula (5) can also be produced by reacting the compound represented by Formula (6) with the compound represented by Formula (7).

(6)

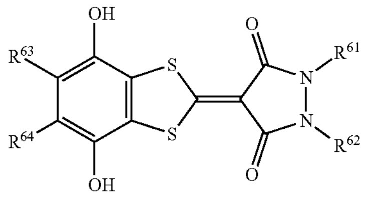

In Formula (6), $R^{61}$ and $R^{62}$ each independently represent a hydrogen atom, an alkyl group, or an aryl group, and $R^{63}$ and $R^{64}$ each independently represent a hydrogen atom, a halogen atom, an alkyl group, an aryl group, an alkoxy group, or an aryloxy group, $$Z^{71}—Y^{71}\text{-}E^{71} \quad (7)$$

in Formula (7), $E^{71}$ represents a group that reacts with a hydroxy group of Formula (6), $Y^{71}$ represents a single bond or a divalent linking group, the divalent linking group is a hydrocarbon group or a group having a structure in which two or more hydrocarbon groups are bonded via a linking group, and the linking group represents —O—, —C(═O)—, —OC(═O)—, —C(═O)O—, —NHC(═O)—, or —C(═O)NH—, and $Z^{71}$ represents a polymerizable group having an ethylenically unsaturated bond.

$R^{61}$ and $R^{62}$ of Formula (6) each have the same definition as that for $R^{51}$ and $R^{52}$ of Formula (5).

$R^{63}$ and $R^{64}$ of Formula (6) each have the same definition as that for $R^{53}$ and $R^{54}$ of Formula (5).

$Y^{71}$ in Formula (7) has the same definition as that for $Y^{51}$ and $Y^{52}$ in Formula (5).

$Z^{71}$ in Formula (7) has the same definition as that for $Z^{51}$ and $Z^{52}$ in Formula (5).

It is preferable that $E^{71}$ in Formula (7) represents-COCl, —O(C═O)Cl, —NCO, —Cl, —Br, —I, —$OSO_2D^1$, or an oxiranyl group and that $D^1$ represents a methyl group, an ethyl group, a phenyl group, or a 4-methylphenyl group.

The content of the compound (1) in the total solid content of the polymerizable composition is preferably in a range of 0.01% to 50% by mass. The lower limit thereof is preferably 0.05% by mass or greater and more preferably 0.1% by mass or greater. The upper limit thereof is preferably 40% by mass or less, more preferably 30% by mass or less, and more preferably 20% by mass or less. The polymerizable composition may contain only one or two or more kinds of the compounds (1). In a case where the resin composition contains two or more kinds of the compounds (1), it is preferable that the total amount thereof is in the above-described range.

<<Ultraviolet Absorbing Agent A>>

The polymerizable composition according to the embodiment of the present invention contains an ultraviolet absorbing agent (hereinafter, also referred to as an ultraviolet absorbing agent A) having a maximum absorption wavelength on a shorter wavelength side than the maximum absorption wavelength of the compound represented by Formula (1) (compound (1)).

The maximum absorption wavelength of the ultraviolet absorbing agent A is present preferably in a wavelength range of 300 to 380 nm, more preferably in a wavelength range of 300 to 370 nm, still more preferably in a wavelength range of 310 to 360 nm, and particularly preferable in a wavelength range of 310 to 350 nm. According to this aspect, a polymer or the like capable of shielding light having a wavelength in an ultraviolet region over a wide range can be formed.

Further, a difference between the maximum absorption wavelength of the compound (1) and the maximum absorption wavelength of the ultraviolet absorbing agent A is preferably in a range of 0 to 70 nm, more preferably in a range of 20 to 60 nm, and still more preferably in a range of 30 to 50 nm. According to this aspect, a polymer or the like capable of shielding light having a wavelength in an ultraviolet region over a wide range can be formed.

It is also preferable that the ultraviolet absorbing agent A is a compound containing a polymerizable group. According to this aspect, a polymer having more excellent light resistance can be formed. Examples of the polymerizable group include the polymerizable groups having an ethylenically unsaturated bond described in the section of the compound (1) above. Among the examples, a (meth)acryloyloxy group, a (meth)acryloylamino group, a (meth)allyl group, or a vinylphenyl group is preferable.

As the ultraviolet absorbing agent A, an aminobutadiene-based compound, a dibenzoylmethane-based compound, a benzophenone-based compound, a benzotriazole-based compound, a hydroxyphenyltriazine-based compound, or the like can be used. Among these, from the viewpoint of having a short absorption wavelength and relatively high light resistance, a 2-(2-hydroxyphenyl)benzotriazole-based compound, a 2-(2-hydroxyphenyl)-1,3,5-triazine-based compound, or a 2-hydroxybenzophenone-based compound is particularly preferable.

As the ultraviolet absorbing agent A, compounds and the like described in JP2003-128730A, JP2003-129033A, JP2014-077076A, JP2015-164994A, JP2015-168822A, and JP2018-135282A, JP2018-168089A, JP2018-168278A, JP2018-188589A, JP2019-001767A, JP2020-023697A, JP2020-041013A, JP5518613B, JP5868465B, JP6301526B, JP6354665B, JP2017-503905A, WO2015/064674A, WO2015/064675A, WO2017/102675A, WO2017/122503A, WO2018/190281A, WO2018/216750A, WO2019/087983A, EP2379512B, and EP2951163B can be used. Further, examples of a commercially available product of the ultraviolet absorbing agent containing a polymerizable group include 2-[2-hydroxy-5-(2-methacryloyloxyethyl)phenyl]2H-benzo[d][1,2,3]triazole (RUVA-93, manufactured by Otsuka Chemical Co., Ltd.).

The content of the ultraviolet absorbing agent A in the total solid content of the polymerizable composition is preferably in a range of 0.01% to 10% by mass and more preferably in a range of 0.01% to 5% by mass.

The total content of the compound (1) and the ultraviolet absorbing agent A in the total solid content of the polymerizable composition is preferably in a range of 0.01% to 20% by mass and more preferably in a range of 0.01% to 10% by mass.

Further, the content of the ultraviolet absorbing agent A is preferably in a range of 50 to 400 parts by mass and more preferably in a range of 50 to 200 parts by mass with respect to 100 parts by mass of the compound (1).

The polymerizable composition may contain only one or two or more kinds of ultraviolet absorbing agents A. In a case where the polymerizable composition contains two or more kinds of ultraviolet absorbing agents A, it is preferable that the total amount thereof is in the above-described ranges.

<<Polymerizable Compound>

The polymerizable composition can contain a polymerizable compound other than the compound represented by Formula (1). As the polymerizable compound, a compound that can be polymerized and cured by applying energy can be used without limitation. Examples of the polymerizable compound include a compound containing a polymerizable group having an ethylenically unsaturated bond. Examples of the polymerizable group having an ethylenically unsaturated bond include a vinyl group, an allyl group, a (meth) acryloyl group, a (meth)acryloyloxy group, a (meth)acryloylamino group, and a vinylphenyl group.

The polymerizable compound may be, for example, any one of a monomer, a prepolymer (that is, a dimer, a trimer, or an oligomer), a mixture thereof, or a (co)polymer of a compound selected from the monomer and the prepolymer. Examples of the monomer and the (co)polymer thereof include an unsaturated carboxylic acid (such as acrylic acid, methacrylic acid, itaconic acid, crotonic acid, isocrotonic acid, or maleic acid), an ester thereof, an amide thereof, and a (co)polymer of the above-described components.

As the polymerizable compound, a (meth)acrylate-based monomer or a styrene-based monomer is preferable.

Specific examples of the (meth)acrylate-based monomer include methyl (meth)acrylate, ethyl (meth)acrylate, butyl (meth)acrylate, 2-hydroxyethyl (meth)acrylate, glycidyl (meth)acrylate, benzyl (meth)acrylate, 2-(2-phenoxy)ethyl (meth)acrylate, 2-ethylhexyl (meth)acrylate, n-octyl (meth) acrylate, isooctyl (meth)acrylate, n-nonyl (meth)acrylate, isononyl (meth)acrylate, n-decyl (meth)acrylate, isodecyl (meth)acrylate, n-dodecyl (meth)acrylate, n-tridecyl (meth) acrylate, n-tetradecyl (meth)acrylate, n-hexadecyl (meth) acrylate, stearyl (meth)acrylate, isobornyl (meth)acrylate, dicyclopentenyl (meth)acrylate, dicyclopentanyl (meth) acrylate, dicyclopentenyloxyethyl (meth)acrylate, 1-hydroxyheptyl (meth)acrylate, 1-hydroxybutyl (meth)acrylate, 1-hydroxypentyl (meth)acrylate, 2 hydroxybutyl (meth) acrylate, ethylene glycol diacrylate, ethylene glycol dimethacrylate, polyethylene glycol diacrylate, polyethylene glycol dimethacrylate, ethoxylated bisphenol A diacrylate, ethoxylated bisphenol A dimethacrylate, ethoxylated trimethylolpropane triacrylate, ethoxylated trimethylolpropane trimethacrylate, ethoxylated glycerin triacrylate, ethoxylated glycerin trimethacrylate, ethoxylated pentaerythritol tetraacrylate, ethoxylated pentaerythritol tetramethacrylate, ethoxylated dipentaerythritol hexaacrylate, polyglycerin monoethylene oxide polyacrylate, polyglycerin polyethylene glycol polyacrylate, dipentaerythritol hexaacrylate, dipentaerythritol hexamethacrylate, neopentyl glycol diacrylate, neopentyl glycol dimethacrylate, pentaerythritol triacrylate, pentaerythritol trimethacrylate, trimethylolpropane triacrylate, trimethylolpropane trimethacrylate, tricyclodecane dimethanol diacrylate, tricyclodecane dimethanol dimethacrylate, 1,6-hexanediol diacrylate, and 1,6-hexanediol dimethacrylate.

Specific examples of the styrene-based monomer include styrene, methylstyrene, dimethylstyrene, trimethylstyrene, ethylstyrene, fluorostyrene, chlorostyrene, methoxystyrene, t-butoxystyrene, and divinylbenzene.

From the viewpoint of being in a liquid state at normal temperature, methyl (meth)acrylate, ethyl (meth)acrylate, butyl (meth)acrylate, 2-hydroxyethyl (meth)acrylate, benzyl (meth)acrylate, 2-ethylhexyl (meth)acrylate, dipentaerythritol hexaacrylate, or pentaerythritol triacrylate is particularly preferable as the polymerizable compound.

The details of the method of using the polymerizable compound, such as the structure of the polymerizable compound, whether to use alone or in combination of two or more kinds thereof, and the content of the polymerizable compound can be arbitrarily set according to the final performance design of the polymerizable composition. For example, from the viewpoint of the sensitivity, a compound having a structure in which the amount of polymerizable groups per molecule is large is preferable, and a bifunctional or higher functional compound is preferable in many cases. Further, from the viewpoint of increasing the strength of the polymer, a trifunctional or higher functional compound, for example, a hexafunctional (meth)acrylate monomer or the like can be used. Further, compounds having different numbers of functional groups or different polymerizable groups, for example, a (meth)acrylate compound, a styrene compound, a vinyl ether compound, and the like may be used in combination.

The content of the polymerizable compound in the total solid content of the polymerizable composition is preferably 30% by mass or greater, more preferably 50% by mass or greater, and still more preferably 60% by mass or greater. The upper limit thereof is less than 100% by mass and can be set to 99.9% by mass or less or 99.5% by mass or less.

In addition, the total content of the compound (1), the ultraviolet absorbing agent A, and the polymerizable compound in the total solid content of the polymerizable composition is preferably 30% by mass or greater, more preferably 50% by mass or greater, and still more preferably 60% by mass or greater. The upper limit thereof can also be set to 100% by mass, 99.9% by mass or less, or 99.5% by mass or less.

The polymerizable composition may contain only one or two or more kinds of polymerizable compounds. In a case where the polymerizable composition contains two or more kinds of polymerizable compounds, it is preferable that the total amount thereof is in the above-described ranges.

<<Polymerization Initiator>>

The polymerizable composition can contain a polymerization initiator. As the polymerization initiator, a compound capable of generating an initiating species required for the polymerization reaction by applying energy can be used. The polymerization initiator can be appropriately selected from, for example, a photopolymerization initiator and a thermal polymerization initiator, and a photopolymerization initiator is preferable.

For example, a photopolymerization initiator having photosensitivity to light rays from an ultraviolet region to a visible region is preferable as the photopolymerization initiator. Further, the photopolymerization initiator may be an activator that causes some action with a photoexcited sensitizer to generate an active radical.

Examples of the photoradical polymerization initiator include a halogenated hydrocarbon derivative (such as a compound having a triazine skeleton or a compound having an oxadiazole skeleton), an acylphosphine compound, hexaarylbiimidazole, an oxime compound, an organic peroxide, a thio compound, a ketone compound, an aromatic onium salt, an aminoacetophenone compound, and a hydroxyacetophenone compound. Examples of the aminoacetophenone compound include aminoacetophenone-based initiators described in JP2009-191179A and JP1998-291969A (JP-H10-291969A). Examples of the acylphosphine compound include the acylphosphine-based initiator described in JP4225898B. Examples of the oxime compound include the compounds described in JP2001-233842A, the compounds described in JP2000-080068A, the compounds described in JP2006-342166A, and the compounds described in paragraphs 0073 to 0075 of JP2016-006475A. Among the examples of the oxime compound, an oxime ester compound is preferable. As the photoradical polymerization initiator, a synthetic product may be used, or a commercially available product on the market may be used.

Examples of commercially available products of the hydroxyacetophenone compound include Omnirad 184, Omnirad 1173, Omnirad 2959, and Omnirad 127 (all manufactured by IGM Resins B. V.). Examples of commercially available products of the aminoacetophenone compound include Omnirad 907, Omnirad 369, Omnirad 369E, and Omnirad 379EG (all manufactured by IGM Resins B. V.). Examples of commercially available products of the acylphosphine compound include Omnirad 819 and Omnirad TPO (both manufactured by IGM Resins B. V.). Examples of commercially available products of the oxime compound include Irgacure OXE01, Irgacure OXE02 (manufactured by BASF SE), and Irgacure OXE03 (manufactured by BASF SE).

The thermal radical polymerization initiator is not particularly limited, and a known thermal radical polymerization initiator can be used. Examples thereof include an azo-based compound such as dimethyl 2,2'-azobis(isobutyrate), 2,2'-azobisisobutyronitrile, 2,2'-azobis (2,4-dimethyl-4-methoxyvaleronitrile), 2,2'-azobis(2,4-dimethylvaleronitrile), dimethyl-2,2'-azobis(2-methylpropionate), 2,2'-azobis(2-methylbutyronitrile), 1,1'-azobis(cyclohexane-1-carbonitrile), 2,2'-azobis(N-butyl-2-methylpropionamide), dimethyl-1,1'-azobis(1-cyclohexanecarboxylate), or 2,2'-azobis[2-(2-imidazolin-2-yl) propane] dihydrochloride; an organic peroxide such as 1,1-di(t-hexylperoxy)cyclohexane, 1,1-di(t-butylperoxy) cyclohexane, 2,2-di(4,4-di-(t-butylperoxy)cyclohexyl) propane, t-hexyl peroxy isopropyl monocarbonate, t-butyl peroxy-3,5,5-trimethyl hexanoate, t-butyl peroxy laurate, dicumyl peroxide, di-t-butyl peroxide, t-butyl peroxy-2-ethyl hexanoate, t-hexyl peroxy-2-ethyl hexanoate, cumene hydroperoxide, or t-butyl hydroperoxide; and an inorganic peroxide such as potassium persulfate, ammonium persulfate, or hydrogen peroxide.

The content of the polymerization initiator in the total solid content of the polymerizable composition is preferably in a range of 0.1% to 20% by mass. The lower limit thereof is preferably 0.3% by mass or greater and more preferably 0.4% by mass or greater. The upper limit thereof is preferably 15% by mass or less and more preferably 10% by mass or less. The polymerizable composition may contain only one or two or more kinds of polymerization initiators. In a case where the polymerization composition contains two or more kinds of polymerization initiators, it is preferable that the total amount thereof is in the above-described range.

<<Resin>>

The polymerizable composition according to the embodiment of the present invention can contain a resin. Examples of the kind of resin include a (meth)acrylic resin, a polyester resin, a polycarbonate resin, a vinyl polymer [such as a polydiene resin, a polyalkene resin, a polystyrene resin, a polyvinyl ether resin, a polyvinyl alcohol resin, a polyvinyl ketone resin, a polyfluorovinyl resin, or a polyvinyl bromide resin], a polythioether resin, a polyphenylene resin, a polyurethane resin, a polysulfonate resin, a nitroso polymer resin, a polysiloxane resin, a polysulfide resin, a polythioester resin, a polysulfone resin, a polysulfonamide resin, a polyamide resin, a polyimine resin, a polyurea resin, a polyphosphazene resin, a polysilane resin, a polysilazane resin, a polyfuran resin, a polybenzoxazole resin, a polyoxadiazole resin, a polybenzothiazinophenothiazine resin, a polybenzothiazole resin, a polypyrazinoquinoxaline resin, a polypyromellitimide resin, a polyquinoxaline resin, a polybenzoimidazoline resin, a polyoxoisoindoline resin, a polydioxoisoindoline resin, a polytriazine resin, a polypyridazine resin, a polypiperazine resin, a polypyridine resin, a polypiperidine resin, a polytriazole resin, a polypyrazole resin, a polypyrrolidine resin, a polycarborane resin, a polyoxabicyclononane resin, a polydibenzofuran resin, a polyphthalide resin, a polyacetal resin, a polyimide resin, an olefin resin, a cyclic olefin resin, an epoxy resin, and a cellulose acylate resin. For the details, the description in paragraphs 0075 to 0097 of JP2009-263616A can be referred to, and the contents thereof are incorporated in the present specification.

Further, a resin containing a polymerizable group can also be used as the resin. Examples of commercially available products of the resin containing a polymerizable group include DIANAL BR Series (polymethyl methacrylate (PMMA), for example, DIANAL BR-80, BR-83, and BR-87; manufactured by Mitsubishi Chemical Corporation); Photomer 6173 (COOH-containing polyurethane acrylic oligomer, manufactured by Diamond Shamrock Co., Ltd.); VISCOAT R-264, KS Resist 106 (both manufactured by Osaka Organic Chemical Industry Ltd.); CYCLOMER P Series (for example, ACA230AA), PLACCEL CF200 Series (all manufactured by Dycel Corporation); Ebecryl 3800 (manufactured by Dycel UCB Co.); and Acrylic-RD-F8 (manufactured by Nippon Shokubai Co., Ltd.).

From the viewpoints of satisfactory compatibility with the compound (1) and ease of obtaining a film with suppressed surface unevenness, a (meth)acrylic resin, a polystyrene resin, a polyester resin, a polyurethane resin, a polycarbonate resin, or a cellulose acylate resin is preferable as the resin.

As the cellulose acylate resin, the cellulose acylate described in paragraphs 0016 to 0021 of JP2012-215689A is preferably used. As the polyester resin, a commercially available product such as the VYLON Series (for example, VYLON 500, manufactured by Toyobo Co., Ltd.) can also be used. As a commercially available product of the (meth) acrylic resin, SK Dyne Series (for example, SK Dyne-SF2147, manufactured by Soken Chemical & Engineering Co., Ltd.) can also be used.

As the polystyrene resin, a resin having 50% by mass or greater of a repeating unit derived from a styrene-based monomer is preferable, a resin having 70% by mass or greater of a repeating unit derived from a styrene-based monomer is more preferable, and a resin having 85% by mass or greater of a repeating unit derived from a styrene-based monomer is still more preferable.

Specific examples of the styrene-based monomer include styrene and a derivative thereof. Here, the styrene derivative is a compound in which another group is bonded to styrene, and examples thereof include alkylstyrene such as o-methylstyrene, m-methylstyrene, p-methylstyrene, 2,4-dimethylstyrene, o-ethylstyrene, or p-ethylstyrene, and substituted styrene in which a hydroxyl group, an alkoxy group, a carboxyl group, or halogen is introduced to a benzene nucleus of styrene such as hydroxystyrene, tert-butoxystyrene, vinyl benzoic acid, o-chlorostyrene, or p-chlorostyrene.

In addition, the polystyrene resin may have a repeating unit derived from a monomer other than the styrene-based monomer. Examples of other monomers include alkyl (meth)acrylate such as methyl (meth)acrylate, cyclohexyl (meth)acrylate, methylphenyl (meth)acrylate, or isopropyl (meth)acrylate; an unsaturated carboxylic acid monomer such as methacrylic acid, acrylic acid, itaconic acid, maleic acid, fumaric acid, or cinnamic acid; an unsaturated dicarboxylic acid anhydride monomer which is an anhydride of maleic acid, itaconic acid, ethylmaleic acid, methylitaconic acid, or chloromaleic acid; an unsaturated nitrile monomer such as acrylonitrile or methacrylonitrile; and a conjugated diene such as 1,3-butadiene, 2-methyl-1,3-butadiene (isoprene), 2,3-dimethyl-1,3-butadiene, 1,3-pentadiene, or 1,3-hexadiene.

Examples of commercially available products of the polystyrene resin include AS-70 (acrylonitrile/styrene copolymer resin, manufactured by NIPPON STEEL Chemical & Material Co., Ltd.) and SMA2000P (styrene/maleic acid copolymer, manufactured by Kawahara Petrochemical Co., Ltd.).

The weight-average molecular weight (Mw) of the resin is preferably in a range of 3000 to 2000000. The upper limit thereof is preferably 1000000 or less and more preferably 500000 or less. The lower limit thereof is preferably 4000 or greater and more preferably 5000 or greater.

The total light transmittance of the resin is preferably 80% or greater, more preferably 85% or greater, and still more preferably 90% or greater. In the present specification, the total light transmittance of the resin is a value measured based on the contents described in "The Fourth Series of Experimental Chemistry 29 Polymer Material" (Maruzen, 1992), pp. 225 to 232, edited by the Chemical Society of Japan.

The content of the resin in the total solid content of the polymerizable composition is preferably in a range of 1% to 99.9% by mass. The lower limit thereof is preferably 20% by mass or greater, more preferably 30% by mass or greater, and still more preferably 40% by mass or greater. The upper limit thereof is preferably 99% by mass or less and more preferably 95% by mass or less. The polymerizable composition may contain only one or two or more kinds of resins. In a case where the polymerization composition contains two or more kinds of resins, it is preferable that the total amount thereof is in the above-described range.

<<Silane Coupling Agent>>

The polymerizable composition according to the embodiment of the present invention may contain a silane coupling agent. In the present specification, the silane coupling agent denotes a silane compound containing a hydrolyzable group and a functional group other than the hydrolyzable group. Further, the hydrolyzable group denotes a substituent that is directly bonded to a silicon atom and can form a siloxane bond by at least one of a hydrolysis reaction or a condensation reaction. Examples of the hydrolyzable group include a halogen atom, an alkoxy group, and an acyloxy group. Among these, an alkoxy group is preferable. That is, it is preferable that the silane coupling agent is a compound containing an alkoxysilyl group. Examples of the functional group other than the hydrolyzable group include a vinyl group, a (meth)allyl group, a (meth)acryloyl group, a mercapto group, an epoxy group, an oxetanyl group, an amino group, a ureido group, a sulfide group, and an isocyanate group, and a phenyl group. Among these, an amino group, a (meth)acryloyl group, and an epoxy group are preferable. Specific examples of the silane coupling agent include the compounds described in paragraphs 0018 to 0036 of JP2009-288703A and the compounds described in paragraphs 0056 to 0066 of JP2009-242604A, and the contents thereof are incorporated in the present specification. Examples of commercially available products of the silane coupling agent include A-50 (organosilane) (manufactured by Soken Chemical & Engineering Co., Ltd.). The content of the silane coupling agent in the total solid content of the polymerizable composition is preferably in a range of 0.1% to 5% by mass. The upper limit thereof is preferably 3% by mass or less and more preferably 2% by mass or less. The lower limit thereof is preferably 0.5% by mass or greater and more preferably 1% by mass or greater. The polymerizable composition may contain only one or two or more kinds of silane coupling agents. In a case where the polymerizable composition contains two or more kinds of silane coupling agents, it is preferable that the total amount thereof is in the above-described range.

<<Solvent>>

The polymerizable composition according to the embodiment of the present invention can contain a solvent. The solvent can be used without particular limitation. It is preferable that the solvent is an organic solvent. Examples of the organic solvent include an ester-based solvent, an ether-based solvent, a ketone-based solvent, and an aromatic hydrocarbon-based solvent.

Examples of the ester-based solvent include ethyl acetate, n-butyl acetate, isobutyl acetate, amyl formate, isoamyl acetate, butyl propionate, isopropyl butyrate, ethyl butyrate, butyl butyrate, methyl lactate, ethyl lactate, alkoxyacetic acid alkyl esters (such as methyl alkoxy acetate, ethyl alkoxy acetate, or butyl alkoxy acetate (specific examples thereof include methyl methoxy acetate, ethyl methoxy acetate, butyl methoxy acetate, methyl ethoxy acetate, and ethyl ethoxy acetate)), 3-alkoxypropionic acid alkyl esters (such as methyl 3-alkoxy propionate or ethyl 3-alkoxy propionate (specific examples thereof include methyl 3-methoxy propionate, ethyl 3-methoxy propionate, methyl 3-ethoxy propionate, and ethyl 3-ethoxy propionate)), 2-alkoxypropionic acid alkyl esters (such as methyl 2-alkoxy propionate, ethyl 2-alkoxy propionate, or propyl 2-alkoxy propionate (specific examples thereof include methyl 2-methoxy propionate, ethyl 2-methoxy propionate, propyl 2-methoxy propionate, methyl 2-ethoxy propionate, and ethyl 2-ethoxy propionate)), methyl 2-methoxy-2-methyl propionate, ethyl 2-ethoxy-2-methyl propionate, methyl pyruvate, ethyl pyruvate, propyl pyruvate, methyl acetoacetate, ethyl acetoacetate, methyl 2-oxobutanoate, ethyl 2-oxobutanoate, cyclohexyl acetate, and 1-methyl-2-methoxyethyl propionate.

Examples of the ether-based solvent include diethylene glycol dimethyl ether, tetrahydrofuran, ethylene glycol monomethyl ether, ethylene glycol monoethyl ether, methyl cellosolve acetate, ethyl cellosolve acetate, diethylene glycol monomethyl ether, diethylene glycol monoethyl ether, diethylene glycol monobutyl ether, propylene glycol monomethyl ether, propylene glycol monomethyl ether acetate, diethylene glycol monoethyl ether acetate (hereinafter, also referred to as ethyl carbitol acetate), diethylene glycol monobutyl ether acetate (hereinafter, also referred to as butyl carbitol acetate), propylene glycol monoethyl ether acetate, and propylene glycol monopropyl ether acetate.

Examples of the ketone-based solvent include methyl ethyl ketone, cyclohexanone, 2-heptanone, and 3-heptanone.

Examples of the aromatic hydrocarbon-based solvent include toluene and xylene.

The polymerizable composition may contain only one or a combination of two or more kinds of such organic solvents. In a case where two or more kinds of organic solvents are used in combination, it is preferable that the organic solvents include two or more selected from the group consisting of methyl 3-ethoxy propionate, ethyl 3-ethoxy propionate, ethyl cellosolve acetate, ethyl lactate, diethylene glycol dimethyl ether, butyl acetate, methyl 3-methoxy propionate, 2-heptanone, cyclohexanone, ethyl carbitol acetate, butyl carbitol acetate, propylene glycol monomethyl ether, and propylene glycol monomethyl ether acetate.

The content of the solvent in the polymerizable composition is preferably 80% by mass or less, more preferably 50% by mass or less, still more preferably 30% by mass or less, and even still more preferably 10% by mass or less. Further, from the viewpoint of simplifying the steps of producing a polymer, it is particularly preferable that the polymerizable composition does not substantially contain a solvent. In the present specification, the case where the polymerizable composition does not substantially contain a solvent denotes that the content of the solvent in the polymerizable composition is 1% by mass or less, preferably 0.5% by mass or less, and more preferably 0.1% by mass or less. Further, it is particularly preferable that the polymerizable composition does not contain a solvent.

<<Surfactant>>

The polymerizable composition according to the embodiment of the present invention can contain a surfactant. Examples of the surfactant include the surfactants described in paragraph 0017 of JP4502784B and paragraphs 0060 to 0071 of JP2009-237362A.

Examples of the surfactant include a fluorine-based surfactant, a silicone-based surfactant, a nonionic surfactant, an anionic surfactant, and a cationic surfactant. Among these, a fluorine-based surfactant or a silicone-based surfactant is preferable.

Examples of commercially available products of the fluorine-based surfactant include MEGAFACE F-171, F-172, F-173, F-176, F-177, F-141, F-142, F-143, F-144, F-437, F-475, F-477, F-479, F-482, F-551-A, F-552, F-554, F-555-A, F-556, F-557, F-558, F-559, F-560, F-561, F-565, F-563, F-568, F-575, F-780, EXP, MFS-330, R-41, R-41-LM, R-01, R-40, R-40-LM, RS-43, TF-1956, RS-90, R-94, RS-72-K, and DS-21 (all manufactured by DIC Corporation), FLUORARD FC430, FC431, and FC171 (all manufactured by Sumitomo 3M Ltd.), SURFLON S-382, SC-101, SC-103, SC-104, SC-105, SC-1068, SC-381, SC-383, S-393, and KH-40 (all manufactured by AGC Inc.), PolyFox PF636, PF656, PF6320, PF6520, and PF7002 (all manufactured by OMNOVA Solutions Inc.), and FTERGENT 710FM, 610FM, 601AD, 601ADH2, 602A, 215M, 245F, 251, 212M, 250, 209F, 222F, 208G, 710LA, 710FS, 730 LM, 650AC, and 681 (all manufactured by NEOS Company Limited).

The fluorine-based surfactant has a molecular structure containing a functional group having a fluorine atom, and an acrylic compound in which a portion of the functional group having a fluorine atom is cleaved in a case where heat is applied thereto so that the fluorine atom volatilizes can also be suitably used. Examples of the fluorine-based surfactant include MEGAFACE DS Series (manufactured by DIC Corporation (The Chemical Daily (Feb. 22, 2016) and Nikkei Sangyo Shimbun (Feb. 23, 2016)) such as MEGAFACE DS-21.

A polymer of a fluorine atom-containing vinyl ether compound containing a fluorinated alkyl group or a fluorinated alkylene ether group and a hydrophilic vinyl ether compound is also preferably used as the fluorine-based surfactant.

A block polymer can also be used as the fluorine-based surfactant. A fluorine-containing polymer compound having a repeating unit derived from a (meth)acrylate compound having a fluorine atom and a repeating unit derived from a (meth)acrylate compound containing 2 or more (preferably 5 or more) alkyleneoxy groups (preferably ethyleneoxy groups or propyleneoxy groups) can also be preferably used as the fluorine-based surfactant.

A fluorine-containing polymer containing an ethylenically unsaturated bond-containing group in a side chain can also be used as the fluorine-based surfactant. Examples thereof include MEGAFACE RS-101, RS-102, RS-718K, and RS-72-K (all manufactured by DIC Corporation).

Examples of the silicone-based surfactant include a linear polymer consisting of a siloxane bond and a modified siloxane polymer in which an organic group is introduced into a side chain or a terminal. Examples of commercially available products of the silicone-based surfactant include DOWSIL 8032 ADDITIVE, Toray Silicone DC3PA, Toray Silicone SH7PA, Toray Silicone DC11PA, Toray Silicone SH21PA, Toray Silicone SH28PA, Toray Silicone SH29PA, Toray Silicone SH30PA, and Toray Silicone SH8400 (all manufactured by Dow Toray Co., Ltd.), X-22-4952, X-22-4272, X-22-6266, KF-351A, K354L, KF-355A, KF-945, KF-640, KF-642, KF-643, X-22-6191, X-22-4515, KF-6004, KP-341, KF-6001, and KF-6002 (all manufactured by Shin-Etsu Chemical Co., Ltd.), F-4440, TSF-4300, TSF-4445, TSF-4460, and TSF-4452 (all manufactured by Momentive Performance Materials Inc.), and BYK-307, BYK-323, and BYK-330 (all manufactured by BYK-Chemie GmbH).

Examples of the nonionic surfactant include glycerol, trimethylolpropane, trimethylolethane, ethoxylate and propoxylate thereof (such as glycerol propoxylate or glycerol ethoxylate), polyoxyethylene lauryl ether, polyoxyethylene stearyl ether, polyoxyethylene oleyl ether, polyoxyethylene octyl phenyl ether, polyoxyethylene nonyl phenyl ether, polyethylene glycol dilaurate, polyethylene glycol distearate, and sorbitan fatty acid ester. Examples of commercially available products of the nonionic surfactant include PLURONIC L10, L31, L61, L62, 10R5, 17R2, and 25R2 (all manufactured by BASF SE), TETRONIC 304, 701, 704, 901, 904, and 150R1 (all manufactured by BASF SE), SOLSPERSE 20000 (manufactured by The Lubrizol Corporation), NCW-101, NCW-1001, and NCW-1002 (all manufactured by FUJIFILM Wako Pure Chemical Corporation), PIONIN D-6112, D-6112-W, and D-6315 (all manufactured by Takemoto Oil & Fat Co., Ltd.), and OLFINE E1010, SURFINOL 104, 400, and 440 (all manufactured by Nisshin Chemical Co., Ltd.).

In a case where the polymerizable composition contains a surfactant, the content of the surfactant in the total solid content of the polymerizable composition is preferably in a range of 0.01% to 3% by mass, more preferably 0.05% to 1% by mass, and still more preferably in a range of 0.1% to 0.8% by mass. The polymerizable composition may contain only one or two or more kinds of surfactants. In a case where the polymerizable composition contains two or more kinds of surfactants, it is preferable that the total amount thereof is in the above-described ranges.

<<Acid Generator>>

The polymerizable composition according to the embodiment of the present invention can contain an acid generator. The acid generator may be a photoacid generator or a thermal acid generator. In the present specification, an acid generator denotes a compound which generates an acid by applying energy such as heat or light. Further, the thermal acid generator denotes a compound that generates an acid by thermal decomposition. Further, the photoacid Examples of the kind generator denotes a compound that generates an acid by light irradiation of acid generator, specific compounds, and preferred examples thereof include the compounds described in paragraphs 0066 to 0122 of JP2008-013646A, and these compounds can also be applied to the present invention.

As the thermal acid generator, a compound having a thermal decomposition temperature of 130° C. to 250° C. is preferable, and a compound having a thermal decomposition temperature of 150° C. to 220° C. is more preferable. Examples of the thermal acid generator include compounds that generate low nucleophilic acids such as a sulfonic acid, a carboxylic acid, and disulfonylimide by heating. As the acid generated by the thermal acid generator, an acid having a pKa of 4 or less is preferable, an acid having a pKa of 3 or less is more preferable, and an acid having a pKa of 2 or less is still more preferable. For example, a sulfonic acid, an alkylcarboxylic acid substituted with an electron withdrawing group, an arylcarboxylic acid, or disulfonylimide is preferable. Examples of the electron withdrawing group include a halogen atom such as a fluorine atom, a haloalkyl group such as a trifluoromethyl group, a nitro group, and a cyano group.

Examples of the photoacid generator include an onium salt compound such as a diazonium salt, a phosphonium salt, a sulfonium salt, or an iodonium salt, which are decomposed by light irradiation to generate an acid, and a sulfonate compound such as imide sulfonate, oxime sulfonate, diazodisulfone, disulfone, or ortho-nitrobenzyl sulfonate. Examples of commercially available products of the photoacid generator include WPAG-469 (manufactured by FUJIFILM Wako Pure Chemical Corporation), CPI-100P (manufactured by San-Apro Ltd.), and Irgacure 290 (manufactured by BASF SE). Further, 2-isopropylthioxanthone or the like can also be used as the photoacid generator.

In a case where the polymerizable composition contains a catalyst, the content of the acid generator in the total solid content of the polymerizable composition is preferably in a range of 0.1% to 20% by mass. The lower limit thereof is preferably 0.5% by mass or greater and more preferably 1% by mass or greater. The upper limit thereof is preferably 15% by mass or less and more preferably 10% by mass or less. The polymerizable composition may contain only one or two or more kinds of acid generators. In a case where the polymerizable composition contains two or more kinds of acid generators, it is preferable that the total amount thereof is in the above-described ranges.

<<Catalyst>>

The polymerizable composition can contain a catalyst. Examples of the catalyst include an acid catalyst such as hydrochloric acid, sulfuric acid, acetic acid, or propionic acid and a base catalyst such as sodium hydroxide, potassium hydroxide, or triethylamine. In a case where the polymerizable composition contains a catalyst, the content of the catalyst in the total solid content of the polymerizable composition is preferably in a range of 0.1% to 20% by mass. The lower limit thereof is preferably 0.5% by mass or greater and more preferably 1% by mass or greater. The upper limit thereof is preferably 15% by mass or less and more preferably 10% by mass or less. The polymerizable composition may contain only one or two or more kinds of catalysts. In a case where the polymerizable composition contains two or more kinds of catalysts, it is preferable that the total amount thereof is in the above-described ranges.

<<Other Additives>>

The polymerizable composition according to the embodiment of the present invention may appropriately contain other additives in addition to the above-described components, as necessary. Examples of the other additives include a filler, a plasticizer, an adhesion accelerator, an antioxidant, an aggregation inhibitor, a processing stabilizer, a compatibilizer, a dispersant, an antifoaming agent, a dye, a pigment, an infrared absorbing agent, a flavoring agent, and an inorganic substance. Examples of the plasticizer include phthalic acid ester (such as dimethyl phthalate, diethyl phthalate, diisopropyl phthalate, dibutyl phthalate, diisobutyl phthalate, dihexyl phthalate, dicyclohexyl phthalate, or diphenyl phthalate), phosphoric acid ester (such as trimethyl phosphate, triethyl phosphate, tributyl phosphate, triphenyl phosphate, or tricresyl phosphate), trimellitic acid ester (such as tributyl trimellitate or tris(2-ethylhexyl)trimellitate), fatty acid ester (such as dimethyl adipate, diethyl adipate, dipropyl adipate, diisopropyl adipate, dibutyl adipate, diisobutyl adipate, dimethyl dodecanoate, dibutyl maleate, or ethyl oleate). Examples of the antioxidant include a phosphorus-based antioxidant and a hydroxylamine-based antioxidant. Examples of the phosphorus-based antioxidant include a phosphite-based antioxidant (such as tris(4-methoxy-3,5-diphenyl)phosphite, tris(nonylphenyl) phosphite, tris(2,4-di-tert-butylphenyl)phosphite, bis(2,6-di-tert-butyl-4-methylphenyl) pentaerythritol diphosphite, or bis(2,4-di-tert-butylphenyl) pentaerythritol diphosphite). Examples of the hydroxylamine-based antioxidant include N,N-dioctadecylhydroxylamine and N,N-dibenzylhydroxylamine.

<<Applications>>

The polymerizable composition according to the embodiment of the present invention can be suitably used for applications in a case where the polymerizable composition may be exposed to light including sunlight and ultraviolet rays and can be suitably used as an ultraviolet shielding material. Specific examples include coating materials or films for window glass of houses, facilities, and transportation equipment; interior/exterior materials and interior/exterior paints of houses, facilities, and transportation equipment; members for light sources that emit ultraviolet rays, such as a fluorescent lamp and a mercury lamp; solar cells, precision machineries, electronic and electrical equipment, and members for a display device; containers or packaging materials for food, chemicals, and drugs; agricultural and industrial sheets; clothing textile products and fibers such as sportswear, stockings, and hats; lenses such as plastics lenses, contact lenses, glasses, and artificial eyes, or coating materials thereof; optical supplies such as optical filters, prisms, mirrors, and photographic materials; stationery such as tapes and inks; and marking boards, marking devices, and the surface coating materials thereof. For the details thereof, the description in paragraphs 0158 to 0218 of JP2009-263617A can be referred to, and the contents thereof are incorporated in the present specification.

The polymerizable composition according to the embodiment of the present invention is preferably used for an ultraviolet cut filter, a lens, or a protective material. The form of the protective material is not particularly limited, and examples thereof include a coating film, a film, and a sheet. Further, the polymerizable composition according to the embodiment of the present invention can also be used as a pressure sensitive adhesive or an adhesive.

Further, the polymerizable composition according to the embodiment of the present invention can also be used for various members of a display device. For example, in a case of a liquid crystal display device, the polymerizable composition can be used for each member constituting the liquid crystal display device such as an antireflection film, a polarizing plate protective film, an optical film, a phase difference film, a pressure sensitive adhesive, and an adhesive. Further, in a case of an organic electroluminescence display device, the polymerizable composition can be used for each member constituting the organic electroluminescence display device such as an optical film, a polarizing plate protective film in a circularly polarizing plate, a phase difference film such as a quarter wave plate, and an adhesive or a pressure sensitive adhesive.

<Polymer>

A first aspect of a polymer according to the embodiment of the present invention is obtained by using the above-described polymerizable composition according to the embodiment of the present invention (hereinafter, also referred to as a polymer (1)). The polymer (1) contains the ultraviolet absorbing agent A and has a structure derived from the compound (1). The polymer (1) further has a component derived from a material contained in the above-described polymerizable composition. Further, in a case where the above-described polymerizable composition further contains a polymerizable compound, the polymer (1) may form a copolymer of the compound (1) and the polymerizable compound. Further, in a case where a compound containing a polymerizable group is used as the ultraviolet absorbing agent A, the polymer (1) may form a copolymer of the compound (1) and the ultraviolet absorbing agent A. In this case, in a case where the polymerizable composition further contains a polymerizable compound, the polymer (1) may form a copolymer of the compound (1), the ultraviolet absorbing agent A, and the polymerizable compound.

In addition, a second aspect of the polymer according to the embodiment of the present invention is a polymer having a structure derived from a compound represented by Formula (5) (hereinafter, also referred to as a polymer (5)). The polymer (5) may have a structure derived from the above-described polymerizable compound. That is, the polymer (5) may form a copolymer of the compound represented by Formula (5) and the polymerizable compound. In addition, the polymer (5) may have a structure derived from the ultraviolet absorbing agent A. That is, the polymer (5) may form a copolymer of the compound represented by Formula (5), the polymerizable compound, and the ultraviolet absorbing agent A.

The content of the structure derived from the compound represented by Formula (5) in the polymer (5) is preferably in a range of 0.01% to 100% by mass. The upper limit thereof is more preferably 50% by mass or less and still more preferably 10% by mass or less. The lower limit thereof is more preferably 0.02% by mass or greater and still more preferably 0.1% by mass or greater.

Further, the content of the structure derived from the above-described polymerizable compound in the polymer (5) is preferably in a range of 50% to 99.99% by mass. The upper limit thereof is more preferably 99.99% by mass or less and still more preferably 99.9% by mass or less. The lower limit thereof is more preferably 50% by mass or greater and still more preferably 90% by mass or greater.

Further, the content of the structure derived from the ultraviolet absorbing agent A in the polymer (5) is preferably in a range of 0.01% to 90% by mass. The upper limit thereof is more preferably 50% by mass or less and still more preferably 10% by mass or less. The lower limit thereof is more preferably 0.02% by mass or greater and still more preferably 0.1% by mass or greater.

The weight-average molecular weight of the polymer (5) is preferably in a range of 5,000 to 80,000, more preferably in a range of 10,000 to 60,000, and still more preferably in a range of 10,000 to 40,000.

<Ultraviolet Absorbing Agent>

An ultraviolet absorbing agent according to the embodiment of the present invention contains a compound represented by Formula (5).

<Ultraviolet Shielding Material>

An ultraviolet shielding material according to the embodiment of the present invention contains the polymer according to the embodiment of the present invention. The ultraviolet shielding material according to the embodiment of the present invention may be formed of the polymerizable composition according to the embodiment of the present invention or may be formed of a composition containing the polymer according to the embodiment of the present invention. Examples of the composition include a composition containing a polymer and a resin. Examples of the resin include the above-described resins.

The shape of the ultraviolet shielding material can be appropriately selected according to the applications and the purpose. Examples of the shape thereof include a coating film, a film, a sheet, a plate, a lens, a tube, and a fiber. Further, the ultraviolet shielding material according to the embodiment of the present invention can also be used as a pressure sensitive adhesive or an adhesive.

The content of the compound (1) or a structure derived from the compound (1) in the ultraviolet shielding material is preferably in a range of 0.005 $mmol/m^2$ to 1 $mmol/m^2$ and more preferably in a range of 0.1 $mmol/m^2$ to 0.5 $mmol/m^2$.

It is also preferable that the ultraviolet shielding material is used by being laminated on a support. Examples of the form of the ultraviolet shielding material to be used include a laminate including a support and the ultraviolet shielding material according to the embodiment of the present invention.

The thickness of the ultraviolet shielding layer in the laminate is preferably in a range of 1 μm to 2500 μm and more preferably in a range of 10 μm to 500 μm.

A material having transparency within a range where the optical performance is not impaired is preferable as the support. The support having transparency denotes that the support is optically transparent and specifically denotes that the total light transmittance of the support is 85% or greater. The total light transmittance of the support is preferably 90% or greater and more preferably 95% or greater.

Suitable examples of the support include a resin film. Examples of the resin constituting a resin film include an ester resin (such as polyethylene terephthalate (PET), polyethylene naphthalate (PEN), polybutylene terephthalate (PBT), or polycyclohexane dimethylene terephthalate (PCT)), an olefin resin (such as polypropylene (PP) or polyethylene (PE)), polyvinyl chloride (PVA), and tricellulose acetate (TAC). Among these, PET is preferable in terms of general purpose properties.

The thickness of the support can be appropriately selected according to the applications, the purpose, and the like. In general, the thickness thereof is preferably in a range of 5 μm to 2500 μm and more preferably in a range of 20 μm to 500 μm.

In addition, it is also preferable that the support is a peelable support. Such a laminate is preferably used as a polarizing plate or the like. Examples of the peelable support include those described below.

The laminate can be formed by coating a transparent body with a composition for forming an ultraviolet shielding material to form a composition layer and applying energy thereto to cure the composition layer. Examples of a method of applying energy include heating and irradiation with light. Among the examples, irradiation with light is preferable, and irradiation with ultraviolet rays is more preferable.

Further, in a case where a composition containing a solvent is used as the composition for forming an ultraviolet shielding material, it is preferable that the amount of the solvent is decreased by drying the solvent contained in the composition layer before the composition layer is cured from the viewpoint of improving the curing properties. In a case where the solvent is dried, examples of the drying method include known methods such as a method of blowing hot air, a method of allowing the solvent to pass through a drying zone controlled to have a predetermined temperature, and a method of drying the solvent with a heater provided in a transport roll.

In a case where the composition layer is cured by irradiation with ultraviolet rays, for example, the curing can be performed using an ultraviolet lamp. The light irradiation amount is preferably in a range of 10 $mJ/cm^2$ to 1000 $mJ/cm^2$. The composition layer is suitably cured by irradiating the layer with ultraviolet rays such that the irradiation amount is set to be in the above-described range. In a case where the composition layer is irradiated with ultraviolet rays, the oxygen concentration can be reduced by purging the ultraviolet irradiation region with inert gas such as nitrogen gas for the purpose of suppressing the curing from being inhibited due to oxygen and further promoting curing of the surface of the composition layer. The oxygen concentration in a case of reducing the oxygen concentration in the curing zone is preferably in a range of 0.01% to 5%.

Further, the temperature during the curing can be increased for the purpose of promoting the curing reaction of the composition layer. From the viewpoint of promoting the curing reaction, the temperature is set to be preferably in a range of 25° C. to 100° C., more preferably in a range of 30° C. to 80° C., and still more preferably in a range of 40° C. to 70° C.

The ultraviolet shielding material according to the embodiment of the present invention can also be produced by placing the polymerizable composition according to the embodiment of the present invention or a semi-cured product obtained by irradiating the polymerizable composition with light and/or heating the polymerizable composition in a molding die and molding the semi-cured product by being irradiated with light and/or being heated. Further, the ultraviolet shielding material according to the embodiment of the present invention can also be produced by placing a composition containing the polymer according to the embodiment of the present invention or a semi-cured product obtained by irradiating the composition with light and/or heating the composition in a molding die and molding the semi-cured product by being irradiated with light and/or being heated.

<Optical Member>

The ultraviolet shielding material according to the embodiment of the present invention can be used for various optical members. Examples of the optical member include an ultraviolet cut filter, a lens, and a protective material. Further, the optical member may be obtained by using a pressure sensitive adhesive or an adhesive containing the ultraviolet shielding material according to the embodiment of the present invention. Examples of such an optical member include a member obtained by bonding a polarizing plate and a polarizing plate protective film with a pressure sensitive adhesive or an adhesive, which contains the ultraviolet shielding material.

The ultraviolet cut filter can be used for an article such as an optical filter, a display device, a solar cell, or window glass. The kind of display device is not particularly limited, and examples thereof include a liquid crystal display device and an organic electroluminescence display device.

Examples of the lens include those obtained by forming the ultraviolet shielding material according to the embodiment of the present invention into a lens shape and those obtained by allowing a coating film on a surface of a lens, an interlayer (an adhesive layer or a pressure sensitive adhesive layer) of a cemented lens, or the like to contain the ultraviolet shielding material according to the embodiment of the present invention.

The kind of the protective material is not particularly limited, and examples thereof include a protective material for a display device, a protective material for a solar cell, and a protective material for window glass. The shape of the protective material is not particularly limited, and examples thereof include a coating film, a film, and a sheet.

Further, a resin film is exemplified as one form of the optical member. The resin film can be formed of a resin composition containing the above-described ultraviolet shielding material according to the embodiment of the present invention and a resin. In addition, the resin film can also be formed of the above-described polymerizable composition according to the embodiment of the present invention, which contains a resin. Examples of the resin used in the resin composition for forming a resin film include the above-described resins. Among these, a (meth)acrylic resin, a polyester fiber, a cyclic olefin resin, and a cellulose acylate resin are preferable, and a cellulose acylate resin is more preferable. The resin composition containing the cellulose acylate resin can contain the additives described in paragraphs 0022 to 0067 of JP2012-215689A. Examples of such additives include sugar esters. By adding a sugar ester compound to the resin composition containing a cellulose acylate resin, the total haze and the internal haze can be decreased without impairing the expression of optical properties even in a case where a heat treatment is not performed before a stretching step. Further, the resin film formed of the resin composition containing the cellulose acylate resin (cellulose acylate film) can be produced by the method described in paragraphs 0068 to 0096 of JP2012-215689. Further, the hard coat layer described in paragraphs 0097 to 0113 of JP2012-215689A may be further laminated on the resin film.

Further, examples of other forms of the optical member include a laminate including a support and the ultraviolet shielding material according to the embodiment of the present invention.

The thickness of the ultraviolet shielding material (ultraviolet shielding material layer) in the laminate is preferably in a range of 1 μm to 2500 μm and more preferably in a range of 10 μm to 500 μm.

A material having transparency within a range where the optical performance is not impaired is preferable as the support. The support having transparency denotes that the support is optically transparent and specifically denotes that the total light transmittance of the support is 85% or greater. The total light transmittance of the support is preferably 90% or greater and more preferably 95% or greater.

Suitable examples of the support include a resin film. Examples of the resin constituting a resin film include an ester resin (such as polyethylene terephthalate (PET), polyethylene naphthalate (PEN), polybutylene terephthalate (PBT), or polycyclohexane dimethylene terephthalate (PCT)), an olefin resin (such as polypropylene (PP) or polyethylene (PE)), polyvinyl chloride (PVA), and tricellulose acetate (TAC). Among these, PET is preferable in terms of general purpose properties.

The thickness of the support can be appropriately selected according to the applications, the purpose, and the like. In general, the thickness thereof is preferably in a range of 5 μm to 2500 μm and more preferably in a range of 20 μm to 500 μm.

In addition, it is also preferable that the support is a peelable support. Such a laminate is preferably used as a polarizing plate or the like. Here, the peelable support denotes a support capable of being peeled off from the ultraviolet shielding material. The stress in a case of peeling the support from the ultraviolet shielding material is preferably in a range of 0.05 N/25 mm or greater and 2.00 N/25 mm or less, more preferably 0.08 N/25 mm or greater and 0.50 N/25 mm or less, and still more preferably 0.11 N/25 mm or greater and 0.20 N/25 mm or less. The stress in a case of peeling the support from the ultraviolet shielding material is evaluated by bonding and fixing the surface of the laminate cut to have a size of a width of 25 mm and a length of 80 mm to a glass base material via an acrylic pressure sensitive adhesive sheet, grasping one end (one side with a width of 25 mm) of a test piece in the length direction using a tension tester (RTF-1210, manufactured by A & D Co., Ltd.), and performing a 90° peeling test (in conformity with Japanese Industrial Standards (JIS) K 6854-1:1999 "Adhesive-Determination of peel strength of bonded assemblies-Part 1:90° peel") in an atmosphere of a temperature of 23° C. and a relative humidity of 60% at a closshead speed (grasping movement speed) of 200 mm/min.

A support containing polyethylene terephthalate (PET) as a main component (the component having the highest content in terms of mass among the components constituting the support) is preferable as the peelable support. From the viewpoint of mechanical strength, the weight-average molecular weight of PET is preferably 20000 or greater, more preferably 30000 or greater, and still more preferably 40000 or greater. The weight-average molecular weight of PET can be determined by dissolving the support in hexafluoroisopropanol (HFIP) using the above-described GPC method. The thickness of the support is not particularly limited, but is preferably in a range of 0.1 to 100 μm, more preferably in a range of 0.1 to 75 μm, still more preferably in a range of 0.1 to 55 μm, and particularly preferably in a range of 0.1 to 10 μm. Further, the support may be subjected to a corona treatment, a glow discharge treatment, undercoating, or the like as a known surface treatment.

The laminate can be formed by coating a transparent body with a composition for forming an ultraviolet shielding material to form a composition layer and applying energy thereto to cure the composition layer. Examples of a method of applying energy include heating and irradiation with light. Among the examples, irradiation with light is preferable, and irradiation with ultraviolet rays is more preferable.

Further, in a case where a composition containing a solvent is used as the composition for forming an ultraviolet shielding material, it is preferable that the amount of the solvent is decreased by drying the solvent contained in the composition layer before the composition layer is cured from the viewpoint of improving the curing properties. In a case where the solvent is dried, examples of the drying method include known methods such as a method of blowing hot air, a method of allowing the solvent to pass through a drying zone controlled to have a predetermined temperature, and a method of drying the solvent with a heater provided in a transport roll.

In a case where the composition layer is cured by irradiation with ultraviolet rays, for example, the curing can be performed using an ultraviolet lamp. The light irradiation amount is preferably in a range of 10 $mJ/cm^2$ to 1000 $mJ/cm^2$. The composition layer is suitably cured by irradiating the layer with ultraviolet rays such that the irradiation amount is set to be in the above-described range. In a case where the composition layer is irradiated with ultraviolet rays, the oxygen concentration can be reduced by purging the ultraviolet irradiation region with inert gas such as nitrogen gas for the purpose of suppressing the curing from being inhibited due to oxygen and further promoting curing of the surface of the composition layer. The oxygen concentration in a case of reducing the oxygen concentration in the curing zone is preferably in a range of 0.01% to 5%.

Further, the temperature during the curing can be increased for the purpose of promoting the curing reaction of the composition layer. From the viewpoint of promoting the curing reaction, the temperature is set to be preferably in a range of 25° C. to 100° C., more preferably in a range of 30° C. to 80° C., and still more preferably in a range of 40° C. to 70° C.

Further, examples of other forms of the optical member include a laminate obtained by laminating a hard coat layer, a transparent support, and a pressure sensitive adhesive layer or an adhesive layer in this order. Such a laminate is preferably used as an ultraviolet cut filter or a protective material (a protective film or a protective sheet). The optical member in this form is not limited as long as any of the support, the hard coat layer, or the pressure sensitive adhesive layer or the adhesive layer contains the above-described ultraviolet shielding material according to the embodiment of the present invention.

As the hard coat layer, any of the hard coat layers described in JP2013-045045A, JP2013-043352A, JP2012-232459A, JP2012-128157A, JP2011-131409A, JP2011-131404A, JP2011-126162A, JP2011-075705A, JP2009-286981A, JP2009-263567A, JP2009-075248A, JP2007-164206A, JP2006-096811A, JP2004-075970A, JP2002-156505A, JP2001-272503A, WO2012/018087A, WO2012/098967A, WO2012/086659A, and WO2011/105594A can be applied. The thickness of the hard coat layer is preferably in a range of 5 μm to 100 μm from the viewpoint of further improving the scratch resistance.

The optical member in this form has a pressure sensitive adhesive layer or an adhesive layer on a side of the support opposite to a side where the hard coat layer is provided. The kind of the pressure sensitive adhesive or the adhesive used for the pressure sensitive adhesive layer or the adhesive layer is not particularly limited, and a known pressure sensitive adhesive or adhesive can be used. As the pressure sensitive adhesive or the adhesive, those containing the acrylic resin described in paragraphs 0056 to 0076 of JP2017-142412A and the crosslinking agent described in paragraphs 0077 to 0082 of JP2017-142412A are also preferably used. Further, the pressure sensitive adhesive or the adhesive may contain the adhesiveness improver (silane compound) described in paragraphs 0088 to 0097 of JP2017-142412A and the additives described in paragraph 0098 of JP2017-142412A. Further, the pressure sensitive adhesive layer or the adhesive layer can be formed by the method described in paragraphs 0099 and 0100 of JP2017-142412A. The thickness of the pressure sensitive adhesive layer or the adhesive layer is preferably in a range of 5 μm to 100 μm from the viewpoint of achieving both adhesive strength and handleability.

The optical member according to the embodiment of the present invention can be preferably used as a constituent member of a display such as a liquid crystal display device (LCD) or an organic electroluminescence display device (OLED).

Examples of the liquid crystal display device include a liquid crystal display device in which a member such as an antireflection film, a polarizing plate protective film, an optical film, a phase difference film, a pressure sensitive adhesive, or an adhesive contains the ultraviolet shielding material according to the embodiment of the present invention. The optical member containing the ultraviolet shielding material according to the embodiment of the present invention may be disposed on any of a viewer side (front side) or a backlight side with respect to the liquid crystal cell and any of a side far from the liquid crystal cell (outer) or a side close to the liquid crystal cell (inner) with respect to the polarizer.

Examples of the organic electroluminescence display device include an organic electroluminescence display device in which a member such as an optical film, a polarizing plate protective film in a circularly polarizing plate, a phase difference film such as a quarter wave plate, an adhesive, or a pressure sensitive adhesive contains the ultraviolet shielding material according to the embodiment of the present invention. By using the ultraviolet shielding material according to the embodiment of the present invention with the above-described configuration, deterioration of the organic electroluminescence display device due to external light can be suppressed.

EXAMPLES

Hereinafter, the present invention will be described in more detail based on the following examples. The materials, the used amounts, the ratios, the treatment contents, the treatment procedures, and the like described in the following examples can be appropriately changed without departing from the gist of the present invention. Therefore, the scope of the present invention is not limited to the following specific examples. In addition, in the structural formulae shown below, Me represents a methyl group.

<Method of Measuring Molar Absorption Coefficient and Maximum Absorption Wavelength>

The maximum absorption wavelength and the molar absorption coefficient of a sample were acquired by measuring the spectral spectrum of a 0.005 mass % solution prepared by dissolving the sample in ethyl acetate (solvent), at room temperature (25° C.) using a 1 cm quartz cell. As a measuring device, UV-1800 (manufactured by Shimadzu Corporation) was used.

SYNTHESIS EXAMPLE OF COMPOUND

(Synthesis Example 1) Synthesis Example of Compound 1-1

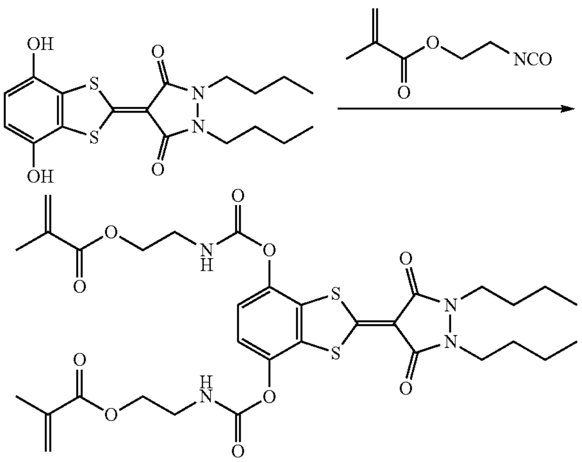

Compound 1-1

2.0 g of 1,2-dibutyl-4-(4,7-dihydroxybenzo[d][1,3]dithiol-2-ylidene)pyrazolidine-3,5-dione and 10 mL of tetrahydrofuran were added to a 100 mL eggplant flask. 1.7 g of 2-isocyanatoethyl methacrylate was added thereto while the mixture was stirred at room temperature. One drop of triethylamine was added to the mixture, and the mixture was heated under reflux for 1 hour. The reaction mixture was cooled to room temperature, 30 mL of ion exchange water was added thereto, and the reaction mixture was allowed to stand overnight. The precipitated crystals were collected by filtration and washed with ion exchange water. The obtained crystals were dried at room temperature and recrystallized with 10 mL of acetonitrile using a trace amount of 2,6-di-t-butyl-4-methylphenol, thereby obtaining 1.7 g of a target compound 1-1.

$^1$H-NMR ($CDCl_3$): δ 7.35 (s, 2H), 6.19 (s, 2H), 5.66 (s, 2H), 5.59 (t, 2H), 4.33 (t, 4H), 3.71-3.58 (m, 8H), 1.99 (s, 6H), 1.55 (m, 4H), 1.29 (m, 4H), 0.92 (t, 6H)

Maximum absorption wavelength (λmax): 375 nm

Molar absorption coefficient at λmax (solvent: ethyl acetate): $3.71\times10^4$ L/mol·cm Molar absorption coefficient at wavelength of 400 nm (solvent: ethyl acetate): $2.5\times10^3$ L/mol·cm Molar absorption coefficient at a wavelength of 420 nm (solvent: ethyl acetate): 100 L/mol·cm or less (Synthesis Example 2) Synthesis Example of Compound 1-5

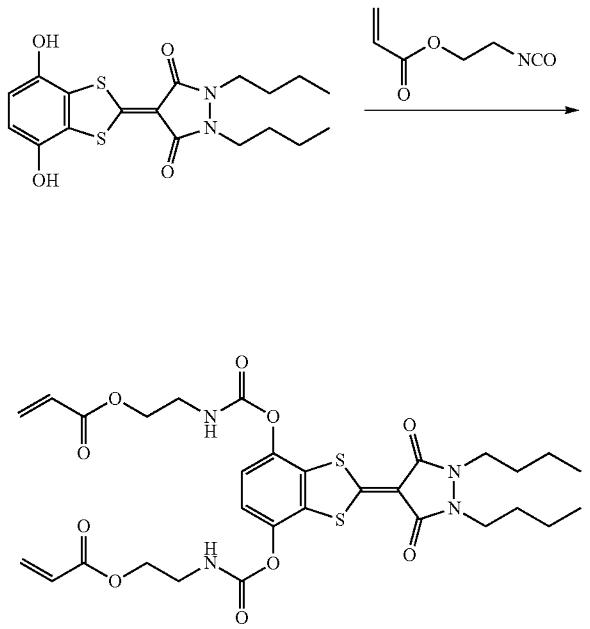

Compound 1-5

2.0 g of 1,2-dibutyl-4-(4,7-dihydroxybenzo[d][1,3]dithiol-2-ylidene)pyrazolidine-3,5-dione and 10 mL of tetrahydrofuran were added to a 50 mL eggplant flask, and a trace amount of 2,6-di-t-butyl-4-methylphenol was further added thereto. 1.6 g of 2-isocyanatoethyl acrylate was added thereto while the mixture was stirred at room temperature. One drop of triethylamine was added to the mixture, and the mixture was heated under reflux for 1 hour. The reaction mixture was cooled to room temperature, 30 mL of ion exchange water was added thereto, and the reaction mixture was allowed to stand overnight. The precipitated crystals were collected by filtration and washed with ion exchange water. The obtained crystals were dried at room temperature and dissolved with 15 mL of ethyl acetate using a trace amount of 2,6-di-t-butyl-4-methylphenol, and 15 mL of hexane was added dropwise thereto. The precipitated crystals were collected by filtration and washed with ethyl acetate and hexane at a ratio of 1/1. 1.5 g of a target compound 1-5 was obtained.

$^1$H-NMR data ($CDCl_3$): δ 7.36 (s, 2H), 6.51 (d, 2H), 6.22 (dd, 2H), 5.92 (d, 2H), 5.54 (t, 2H), 4.35 (t, 4H), 3.71-3.59 (m, 8H), 1.55 (m, 4H), 1.30 (m, 4H), 0.92 (t, 6H)

Maximum absorption wavelength (λmax): 376 nm

Molar absorption coefficient at λmax (solvent: ethyl acetate): $3.78\times10^4$ L/mol·cm Molar absorption coefficient at wavelength of 400 nm (solvent: ethyl acetate): $2.9\times10^3$ L/mol·cm Molar absorption coefficient at a wavelength of 420 nm (solvent: ethyl acetate): 100 L/mol·cm or less (Synthesis Example 3) Synthesis Example of Compound 1-13

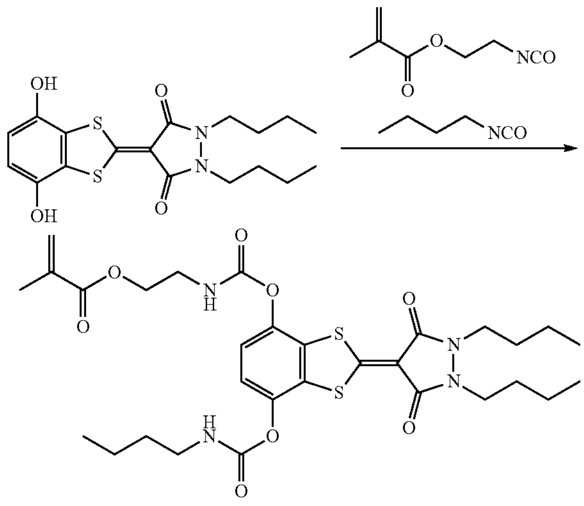

Compound 1-13

2.0 g of 1,2-dibutyl-4-(4,7-dihydroxybenzo[d][1,3]dithiol-2-ylidene)pyrazolidine-3,5-dione and 10 mL of tetrahydrofuran were added to a 100 mL eggplant flask equipped with a calcium chloride tube. 0.9 g of 2-isocyanatoethyl methacrylate and 0.6 g of butyl isocyanate were added thereto while the mixture was stirred at room temperature. One drop of triethylamine was added to the mixture, and the mixture was allowed to stand at room temperature for 3 days. The reaction mixture was concentrated under reduced pressure and purified by silica gel chromatography. The resultant was recrystallized with isopropyl alcohol, thereby obtaining 0.9 g of a target compound 1-13.

$^1$H-NMR ($CDCl_3$): δ 7.35 (d, 1H), 7.34 (d, 1H), 6.20 (s, 1H), 5.66 (s, 1H), 5.51 (t, 1H), 5.17 (t, 1H), 4.34 (m, 2H), 3.71-3.59 (m, 6H), 3.30 (m, 2H), 2.0 (s, BH), 1.66-1.50 (m, 6H), 1.49-1.34 (m, 2H), 1.36-1.23 (m, 4H), 1.03-0.88 (m, 9H)

Maximum absorption wavelength (λmax): 376 nm

Molar absorption coefficient at λmax (solvent: ethyl acetate): $3.62\times10^4$ L/mol·cm Molar absorption coefficient at wavelength of 400 nm (solvent: ethyl acetate): $2.6\times10^3$ L/mol·cm Molar absorption coefficient at a wavelength of 420 nm (solvent: ethyl acetate): 100 L/mol·cm or less (Synthesis Example 4) Synthesis Example of Mixture of Compounds 1-17, 1-18, and 1-19

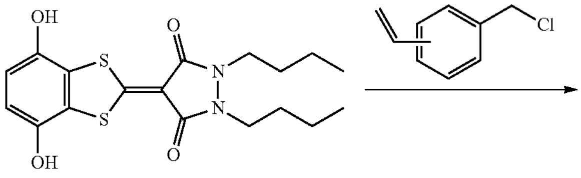

-continued

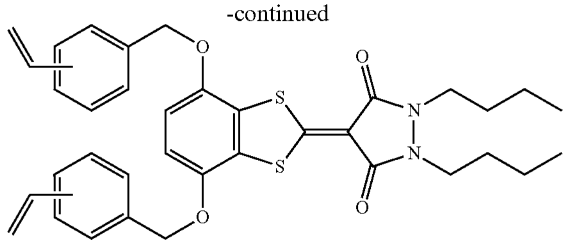

Mixture of compounds 1-17, 1-18, and 1-19

1.2 g of 1,2-dibutyl-4-(4,7-dihydroxybenzo[d][1,3]dithiol-2-ylidene)pyrazolidine-3,5-dione, 1.1 g of chloromethylstyrene (m, p-mixture), a trace amount of 2,6-di-t-butyl-4-methylphenol, and 6 mL of N,N-dimethylformamide were added to a 50 mL eggplant flask. 0.6 g of potassium carbonate was added to the mixture, and the mixture was stirred at 60° C. for 2 hours. The reaction mixture was cooled to room temperature, and 18 mL of pure water was added dropwise thereto. The mixture was stirred for 1 hour, and the precipitated crystals were collected by filtration and sequentially washed with pure water and methanol. The resultant was recrystallized with 6 mL of acetonitrile using a trace amount of 2,6-di-t-butyl-4-methylphenol, thereby obtaining 1.0 g of a mixture of target compounds 1-17, 1-18, and 1-19.

$^1$H-NMR ($CDCl_3$): δ 7.45-7.31 (m, 8H), 6.81 (s, 2H), 6.74 (dd, 2), 5.78 (d, 2H), 5.28 (d, 2H), 5.15 (s, 4H), 3.66 (t, 4H), 1.56 (m, 4H), 1.31 (m, 4H), 0.91 (t, 6H)

Maximum absorption wavelength (λmax): 379 nm

Molar absorption coefficient at λmax (solvent: ethyl acetate): $4.04\times10^4$ L/mol·cm Molar absorption coefficient at wavelength of 400 nm (solvent: ethyl acetate): $5.1\times10^3$ L/mol·cm Molar absorption coefficient at wavelength of 420 nm (solvent: ethyl acetate): 600 L/mol·cm (Synthesis Example 5) Synthesis Example of Compound 1-33

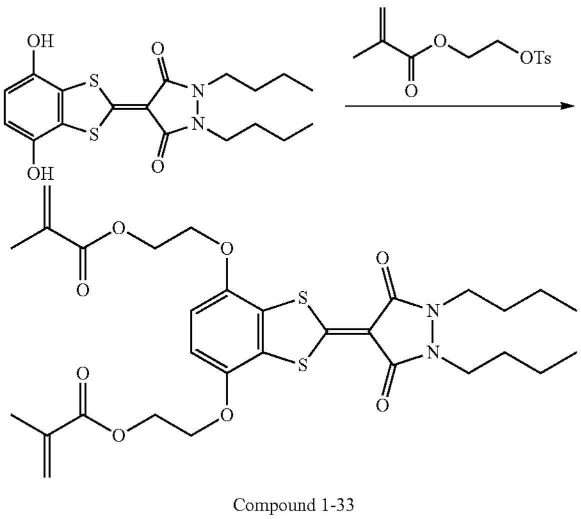

Compound 1-33

2.0 g of 1,2-dibutyl-4-(4,7-dihydroxybenzo[d][1,3]dithiol-2-ylidene)pyrazolidine-3,5-dione, 4.4 g of ethyl 2-(p-toluenesulfonyloxy) methacrylate, a trace amount of 2,6-di-t-butyl-4-methylphenol, and 10 mL of N,N-dimethylformamide were added to a 50 mL eggplant flask. 1.7 g of potassium carbonate was added to the mixture, and the mixture was stirred at 80° C. for 2 hours. 0.4 g of potassium carbonate was added to the reaction mixture, and the mixture was further stirred at 80° C. for 2 hours. The reaction mixture was cooled to room temperature, and 30 mL of ion exchange water was added dropwise thereto. The mixture was stirred for 1 hour, and the precipitated crystals were collected by filtration and sequentially washed with pure water and isopropyl alcohol. The resultant was recrystallized with 15 mL of isopropyl alcohol, thereby obtaining 1.4 g of a target compound 1-33.

$^1$H-NMR ($CDCl_3$): δ 6.84 (s, 2H), 6.16 (s, 2H), 5.62 (s, 2H), 4.52 (t, 4H), 4.34 (t, 4H), 3.67 (t, 4H), 1.96 (s, 6H), 1.55 (m, 4H), 1.31 (m, 4H), 0.92 (t, 6H)

Maximum absorption wavelength (λmax): 378 nm

Molar absorption coefficient at λmax (solvent: ethyl acetate): $3.75\times10^4$ L/mol·cm Molar absorption coefficient at wavelength of 400 nm (solvent: ethyl acetate): $3.9\times10^3$ L/mol·cm Molar absorption coefficient at a wavelength of 420 nm (solvent: ethyl acetate): 100 L/mol·cm or less (Synthesis Example 6) Synthesis Example of Compound 1-47

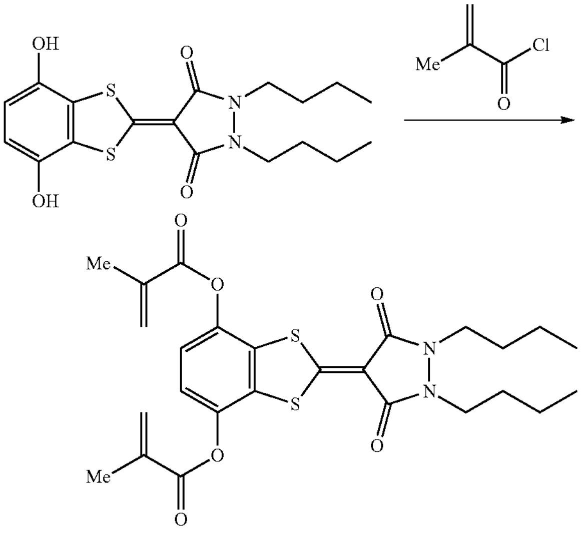

Compound 1-47

2.0 g of 1,2-dibutyl-4-(4,7-dihydroxybenzo[d][1,3]dithiol-2-ylidene)pyrazolidine-3,5-dione, 1.1 g of triethylamine, and 10 mL of tetrahydrofuran were added to a 10 mL eggplant flask, and 1.06 mL of methacrylic acid chloride was added dropwise thereto under ice-cooling. The mixture was stirred for 1 hour under ice-cooling, 30 mL of ion exchange water was added thereto, and the mixture was allowed to stand overnight. The precipitated crystals were collected by filtration and dried at room temperature. The crystals were purified by silica gel chromatography, 5 mL of ethyl acetate and a small amount of 2,6-di-t-butyl-4-methylphenol were added thereto, the mixture was heated and dissolved, and 50 mL of hexane was added thereto. The precipitated crystals were collected by filtration and dried at room temperature, thereby obtaining 1.5 g of a target compound 1-47.

$^1$H-NMR ($CDCl_3$): δ 7.35 (s, 2H), 6.45 (s, 2H), 5.88 (s, 2H), 3.66 (t, 4H), 2.10 (s, 6H), 1.54 (m, 4H), 1.31 (m, 4H), 0.92 (t, 6H)

Maximum absorption wavelength (λmax): 374 nm

Molar absorption coefficient at λmax (solvent: ethyl acetate): $3.76 \times 10^4$ L/mol·cm Molar absorption coefficient at wavelength of 400 nm (solvent: ethyl acetate): $2.10 \times 10^3$ L/mol·cm Molar absorption coefficient at wavelength of 420 nm (solvent: ethyl acetate): 500 L/mol·cm (Synthesis Example 7) Synthesis Example of Compound 1-9

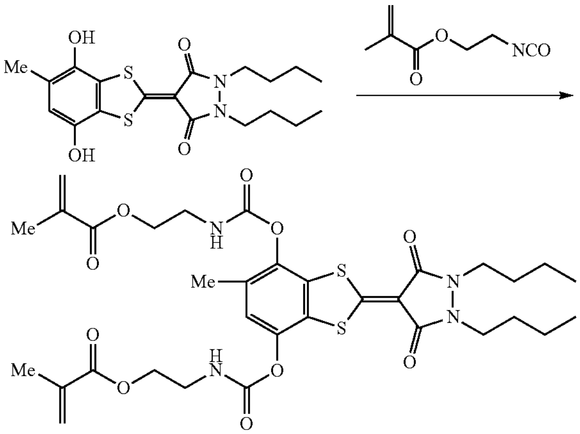

Compound 1-9

0.82 g of 1,2-dibutyl-4-(4,7-dihydroxy-5-methylbenzo[d][1,3]dithiol-2-ylidene)pyrazolidine-3,5-dione and 4 mL of tetrahydrofuran were added to a 50 mL eggplant flask. 0.70 g of 2-isocyanatoethyl methacrylate was added thereto while the mixture was stirred at room temperature. One drop of triethylamine was added to the mixture, and the mixture was heated under reflux for 1 hour. The reaction mixture was cooled to room temperature, 12 mL of ion exchange water was added thereto, and the mixture was stirred at room temperature. The precipitated crystals were collected by filtration and washed with ion exchange water. The obtained crystals were dried at room temperature and recrystallized with 12 mL of acetonitrile using a trace amount of hydroquinone monomethyl ether, thereby obtaining 1.18 g of a target compound 1-9.

$^1$H-NMR ($CDCl_3$): δ 7.22 (s, 1H), 6.20 (s, 2H), 5.66 (s, 2H), 5.53 (m, 2H), 4.34 (t, 4H), 3.67-3.59 (m, 8H), 2.26 (s, 3H), 1.99 (s, 6H), 1.54 (m, 4H), 1.29 (m, 4H), 0.92 (t, 6H)

Maximum absorption wavelength (λmax): 379 nm

Molar absorption coefficient at λmax (solvent: ethyl acetate): $3.63 \times 10^4$ L/mol·cm Molar absorption coefficient at a wavelength of 400 nm (solvent: ethyl acetate): $4.2 \times 10^3$ L/mol·cm Molar absorption coefficient at wavelength of 420 nm (solvent: ethyl acetate): 600 L/mol·cm (Synthesis Example 8) Synthesis Example of Compound 1-50

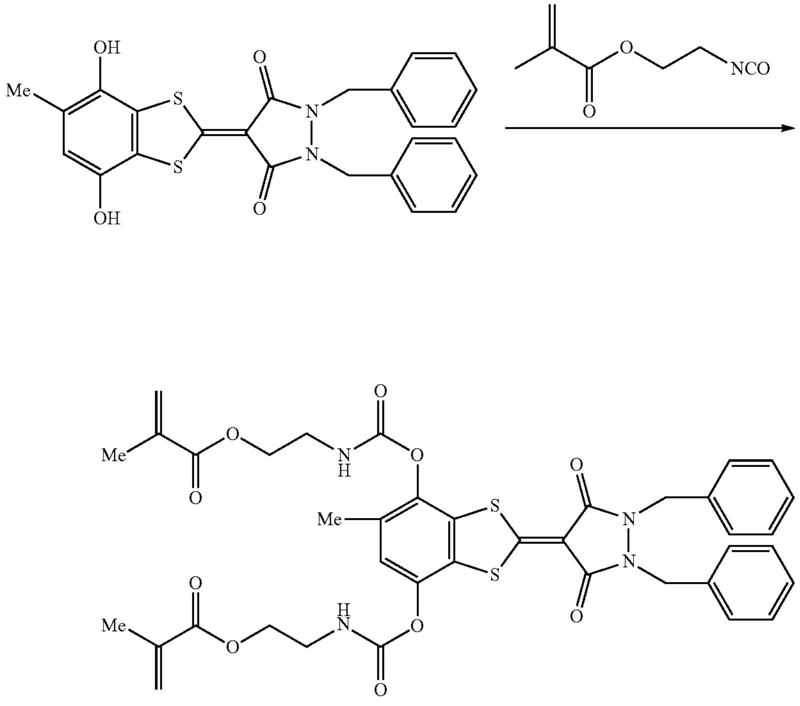

Compound 1-50

121 mg of 1,2-dibutyl-4-(4,7-dihydroxy-5-methylbenzo[d][1,3]dithiol-2-ylidene)pyrazolidine-3,5-dione and 1 mL of tetrahydrofuran were added to a 50 mL eggplant flask. 94 mg of 2-isocyanatoethyl methacrylate was added thereto while the mixture was stirred at room temperature. One drop of triethylamine was added to the mixture, and the mixture was stirred at 70° C. for 1 hour. The reaction mixture was cooled to room temperature, 30 mL of ion exchange water was added thereto, and the mixture was extracted with 30 mL of ethyl acetate. The obtained organic layer was sequentially washed with 30 mL of ion exchange water and 30 mL of saturated saline, dried over magnesium sulfate, filtered, and concentrated. Here, a trace amount of p-methoxyphenol was added thereto. The obtained oily substance was purified by silica gel column chromatography, 2 mL of methanol was added thereto, and the precipitated crystals were collected by filtration. The obtained crystals were dried at room temperature, thereby obtaining 149 mg of a target compound 1-50.

$^1$H-NMR ($CDCl_3$): δ 7.33-7.20 (m, 7H), 7.16-7.07 (m, 4H), 6.19 (s, 2H), 5.65 (s, 2H), 5.54 (m, 2H), 4.76 (s, 4H), 4.34 (m, 4H), 3.63 (m, 4H), 2.27 (s, 3H), 1.98 (s, 6H)

Maximum absorption wavelength (λmax): 383 nm

Molar absorption coefficient at λmax (solvent: ethyl acetate): $4.19\times10^4$ L/mol·cm Molar absorption coefficient at wavelength of 400 nm (solvent: ethyl acetate): $8.0\times10^3$ L/mol·cm Molar absorption coefficient at wavelength of 420 nm (solvent: ethyl acetate): 600 L/mol·cm (Synthesis Example 9) Synthesis Example of Compound 1-48

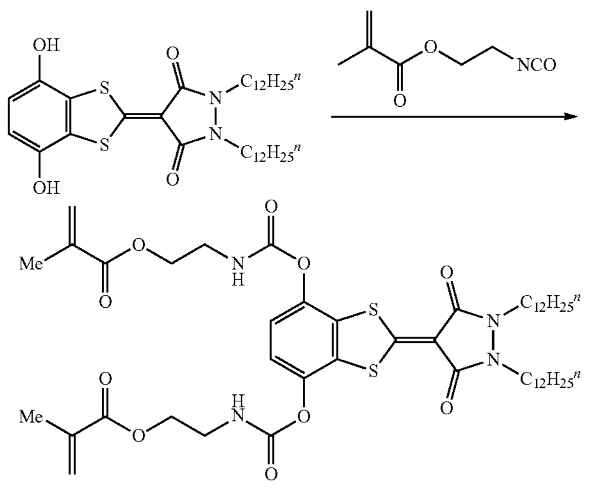

Compound 1-48

0.94 g of 1,2-didodecyl-4-(4,7-dihydroxybenzo[d][1,3]dithiol-2-ylidene)pyrazolidine-3,5-dione and 3 mL of tetrahydrofuran were added to a 50 mL eggplant flask. 0.52 g of 2-isocyanatoethyl methacrylate was added thereto while the mixture was stirred at room temperature. One drop of triethylamine was added to the mixture, and the mixture was heated under reflux for 1 hour. The reaction mixture was cooled to room temperature, 30 mL of ion exchange water was added thereto, and the mixture was extracted with 30 mL of ethyl acetate. The obtained organic layer was washed with 30 mL of saturated saline, dried over magnesium sulfate, filtered, and concentrated. Here, a trace amount of p-methoxyphenol was added thereto. The obtained oily substance was purified by silica gel column chromatography, 12 mL of methanol was added thereto, and the precipitated crystals were collected by filtration. The obtained crystals were dried at room temperature, thereby obtaining 0.50 g of a target compound 1-48.

$^1$H-NMR ($CDCl_3$): δ 7.34 (s, 2H), 6.20 (s, 2H), 5.66 (s, 2H), 5.54 (t, 2H), 4.34 (t, 4H), 3.69-3.59 (m, 8H), 1.99 (s, 6H), 1.59-1.50 (m, 4H), 1.31-1.21 (m, 36H), 0.87 (t, 6H)

Maximum absorption wavelength (λmax): 376 nm

Molar absorption coefficient at λmax (solvent: ethyl acetate): $3.40\times10^4$ L/mol·cm Molar absorption coefficient at wavelength of 400 nm (solvent: ethyl acetate): $2.5\times10^3$ L/mol·cm Molar absorption coefficient at wavelength of 420 nm (solvent: ethyl acetate): 400 L/mol·cm (Synthesis Example 10) Synthesis Example of Compound 1-8

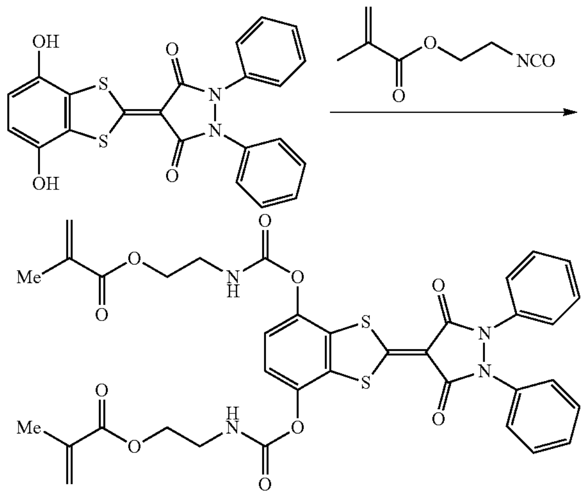

Compound 1-8

94 g of 1,2-diphenyl-4-(4,7-dihydroxybenzo[d][1,3]dithiol-2-ylidene)pyrazolidine-3,5-dione and 3 mL of tetrahydrofuran were added to a 50 mL eggplant flask. 0.77 g of 2-isocyanatoethyl methacrylate was added thereto while the mixture was stirred at room temperature. One drop of triethylamine was added to the mixture, and the mixture was stirred at room temperature for 1 hour. 6 mL of ion exchange water was added to the reaction mixture, and the precipitated crystals were collected by filtration and washed with ion exchange water. A trace amount of 2,6-ditertiarybutyl-4-methylphenol and 5 mL of methanol were added to the obtained crystals, and the mixture was heated and stirred for 30 minutes. The mixture was cooled to room temperature, filtered, and dried, thereby obtaining 1.07 g of a target compound 1-8.

$^1$H-NMR ($CDCl_3$): δ 7.43 (d, 4H), 7.39 (s, 2H), 7.32 (t, 4H), 7.17 (t, 2H), 6.20 (s, 2H), 5.66 (s, 2H), 5.59 (t, 2H), 4.34 (t, 4H), 3.63 (m, 4H), 2.00 (s, 6H)

Maximum absorption wavelength (λmax): 385 nm

Molar absorption coefficient at λmax (solvent: ethyl acetate): $3.82\times10^4$ L/mol·cm Molar absorption coefficient at wavelength of 400 nm (solvent: ethyl acetate): $1.3\times10^4$ L/mol·cm Molar absorption coefficient at a wavelength of 420 nm (solvent: ethyl acetate): 2.16×10$^3$ L/mol·cm (Synthesis Example 11) Synthesis Example of Compound 1-51

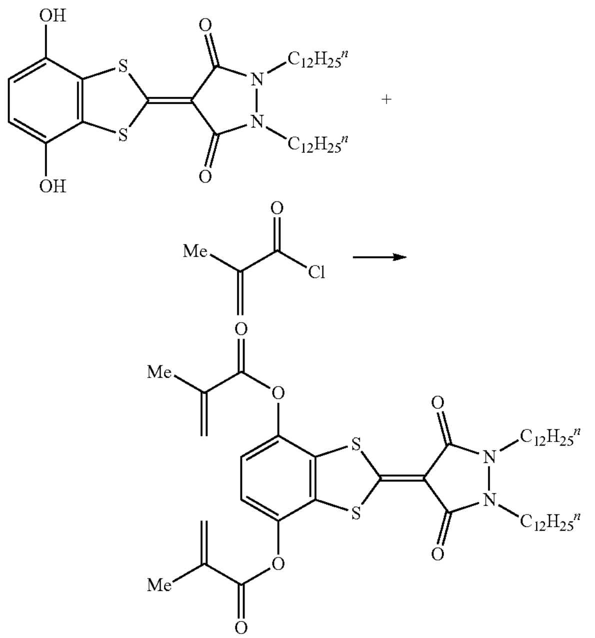

Compound 1-51

2.9 g of 1,2-didodecyl-4-(4,7-dihydroxybenzo[d][1,3]dithiol-2-ylidene)pyrazolidine-3,5-dione, 1.0 g of triethylamine, and 8 mL of tetrahydrofuran were added to a 100 mL eggplant flask, and 0.96 mL of methacrylic acid chloride was added dropwise thereto under ice-cooling. The mixture was stirred for 1 hour under ice-cooling, 24 mL of ion exchange water was added thereto, and 40 mL of ethyl acetate was further added thereto. After the mixture was vigorously stirred, the liquid was separated and the aqueous phase was removed. The mixture was washed with 40 mL of saline solution, anhydrous magnesium sulfate was added thereto, and the mixture was dried, filtered, and concentrated under reduced pressure. The resultant was purified silica gel chromatography, a trace amount of p-methoxyphenol was added thereto, and the mixture was concentrated under reduced pressure. 8 mL of acetonitrile was added to the residues, the mixture was stirred at room temperature, and the precipitated crystals were collected by filtration and dried at room temperature, thereby obtaining 0.9 g of a target compound 1-51.

$^1$H-NMR ($CDCl_3$): δ 7.35 (s, 2H), 6.45 (s, 2H), 5.88 (s, 2H), 3.64 (t, 4H), 2.10 (s, 6H), 1.55 (m, 4H), 1.35-1.17 (m, 36H), 0.87 (t, 6H)

Maximum absorption wavelength (λmax): 373 nm

Molar absorption coefficient at λmax (solvent: ethyl acetate): 3.10×10$^4$ L/mol·cm Molar absorption coefficient at wavelength of 400 nm (solvent: ethyl acetate): 1.83×10$^3$ L/mol·cm Molar absorption coefficient at wavelength of 420 nm (solvent: ethyl acetate): 500 L/mol·cm

PRODUCTION EXAMPLE OF POLYMER (Production Example 1) Production Example of Polymer A-1

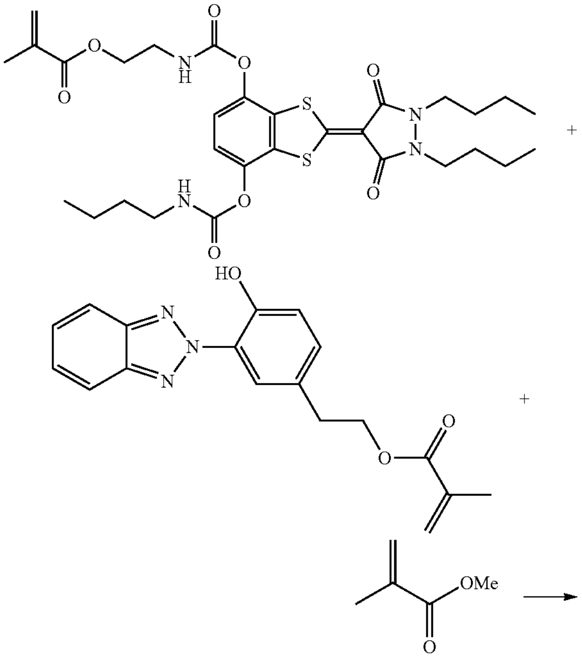

101 mg of the compound 1-13 (maximum absorption wavelength: 376 nm) obtained in Synthesis Example 3, 115 mg of 2-[2-hydroxy-5-(2-methacryloyloxyethyl)phenyl]2H-benzo[d][1,2,3]triazole (maximum absorption wavelength: 338 nm) as an ultraviolet absorbing agent, 9.8 g of methyl methacrylate, and 40.0 g of propylene glycol monomethyl ether acetate were added to a 200 mL three-neck flask, and the mixture was stirred at 80° C. for 30 minutes in a nitrogen stream. 135 mg of dimethyl 2,2'-azobis(isobutyrate) (V-601, manufactured by FUJIFILM Wako Pure Chemical Corporation (hereinafter referred to as V-601)) was added to the solution, and the solution was stirred at 80° C. for 4 hours. Further, 37 mg of V-601 was added thereto, and the mixture was stirred at 90° C. for 2 hours and cooled to room temperature. The obtained reaction mixture was slowly added to a mixture of 140 mL of hexane and 60 mL of isopropyl alcohol, and the mixture was allowed to stand overnight. The precipitated precipitate was collected by filtration and washed with a mixture of hexane and isopropyl alcohol. 140 mL of hexane and 60 mL of isopropyl alcohol were added to the obtained powder, and the mixture was stirred at room temperature for 1 hour and allowed to stand at room temperature overnight. The precipitate was collected by filtration, washed with a mixture of hexane and isopropyl alcohol, and dried at 50° C. 8.0 g of a target polymer A-1 was obtained. The number average molecular weight of the obtained polymer A-1 was 17,300 (in terms of polystyrene).

150 mg of the obtained polymer A-1 was dissolved in 100 mL of chloroform, and the absorption spectrum was measured. The maximum absorption wavelengths of the polymer A-1 were 378 nm (absorbance of 1.10) and 347 nm (absorbance of 1.22).

The polymer A-1 was capable of sufficiently shielding light having a wavelength of approximately 400 nm. Further, the shielding properties against light having a wavelength shorter than 350 nm were also excellent. In addition, the polymer A-1 was less colored.

(Production Example 2) Production Example of Polymer A-2

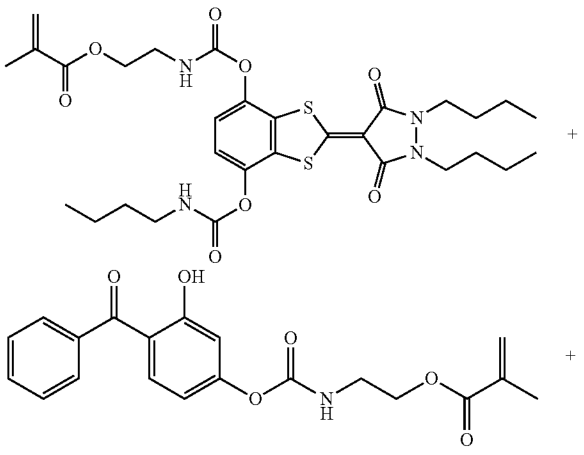

Compound B

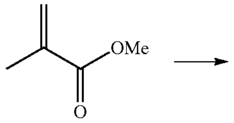

52 mg of the compound 1-13 (maximum absorption wavelength: 376 nm) obtained in Synthesis Example 3, 176 mg of the compound B (maximum absorption wavelength: 329 nm) described in JP2020-041013A as an ultraviolet absorbing agent, 9.8 g of methyl methacrylate, and 40.0 g of propylene glycol monomethyl ether acetate were added to a 100 mL three-neck flask, and the mixture was stirred at 80° C. for 30 minutes in a nitrogen stream. 135 mg of V-601 was added to the solution, and the mixture was stirred at 80° C. for 4 hours. Further, 37 mg of V-601 was added thereto, and the mixture was stirred at 90° C. for 2 hours and cooled to room temperature. The obtained reaction mixture was slowly added to a mixture of 140 mL of hexane and 60 mL of isopropyl alcohol, and the mixture was allowed to stand overnight. The precipitated precipitate was collected by filtration and washed with a mixture of hexane and isopropyl alcohol. 140 mL of hexane and 60 mL of isopropyl alcohol were added to the obtained powder, and the mixture was stirred at room temperature for 1 hour and allowed to stand at room temperature overnight. The precipitate was collected by filtration, washed with a mixture of hexane and isopropyl alcohol, and dried at 50° C. 8.0 g of a target polymer A-2 was obtained. The number average molecular weight of the obtained polymer A-2 was 13,900 (in terms of polystyrene).

200 mg of the obtained exemplary polymer A-2 was dissolved in 100 mL of chloroform, and the absorption spectrum was measured. The maximum absorption wavelengths of the polymer A-1 were 378 nm (absorbance of 0.91) and 335 nm (absorbance of 0.89).

The polymer A-2 was capable of sufficiently shielding light having a wavelength of approximately 400 nm. Further, the shielding properties against light having a wavelength shorter than 350 nm were also excellent. In addition, the polymer A-2 was less colored.

(Production Example 3) Production Example of Polymer A-3

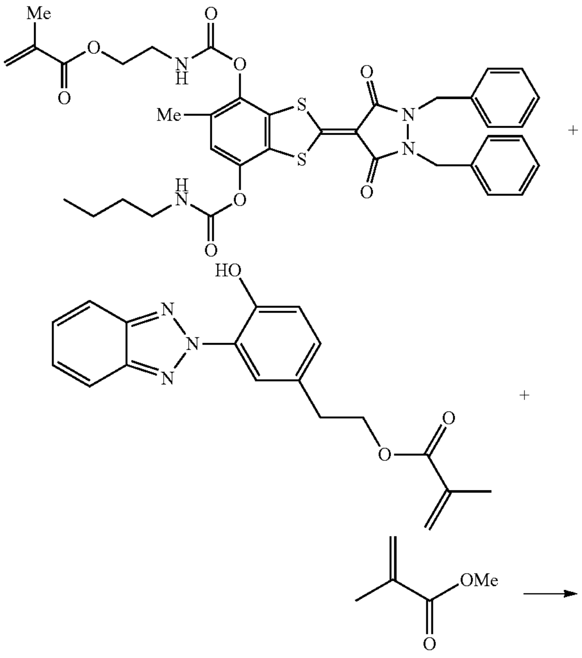

114 mg of the compound 1-54 (maximum absorption wavelength: 382 nm), 115 mg of 2-[2-hydroxy-5-(2-methacryloyloxyethyl)phenyl]2H-benzo[d][1,2,3]triazole (maximum absorption wavelength: 338 nm) as an ultraviolet absorbing agent, 9.8 g of methyl methacrylate, and 40.0 g of propylene glycol monomethyl ether acetate were added to a 200 mL three-neck flask, and the mixture was stirred at 80° C. for 30 minutes in a nitrogen stream. 135 mg of dimethyl 2,2'-azobis(isobutyrate) (V-601, manufactured by FUJIFILM Wako Pure Chemical Corporation (hereinafter referred to as V-601)) was added to the solution, and the solution was stirred at 80° C. for 4 hours. Further, 37 mg of V-601 was added thereto, and the mixture was stirred at 90° C. for 2 hours and cooled to room temperature. The obtained reaction mixture was slowly added to a mixture of 140 mL of hexane and 60 mL of isopropyl alcohol, and the mixture was allowed to stand overnight. The precipitated precipitate was collected by filtration and washed with a mixture of hexane and isopropyl alcohol. 140 mL of hexane and 60 mL of isopropyl alcohol were added to the obtained powder, and the mixture was stirred at room temperature for 1 hour and allowed to stand at room temperature overnight. The precipitate was collected by filtration, washed with a mixture of hexane and isopropyl alcohol, and dried at 50° C. 7.6 g of a target polymer A-3 was obtained. The number average molecular weight of the obtained polymer A-3 was 19,100 (in terms of polystyrene).

150 mg of the obtained polymer A-3 was dissolved in 100 mL of chloroform, and the absorption spectrum was measured. The maximum absorption wavelengths of the polymer A-3 were 384 nm (absorbance of 1.01) and 346 nm (absorbance of 1.12).

The polymer A-3 was capable of sufficiently shielding light having a wavelength of approximately 400 nm. Further, the shielding properties against light having a wavelength shorter than 350 nm were also excellent. In addition, the polymer A-3 was less colored.

(Production Example 4) Production Example of Polymer B-1

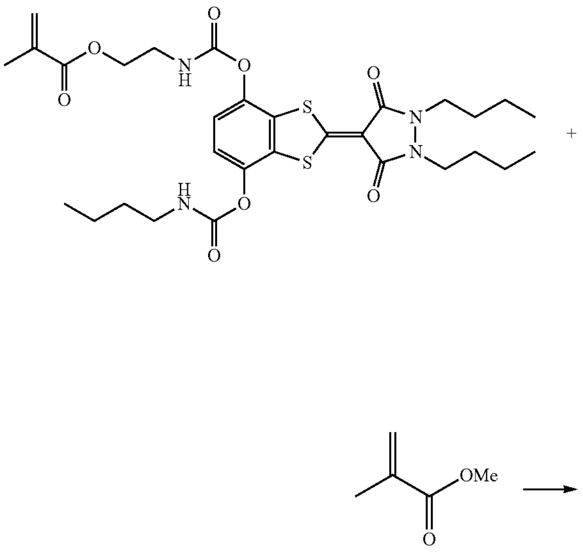

100 mg of the compound 1-13 obtained in Synthesis Example 3, 9.9 g of methyl methacrylate, and 40.0 g of propylene glycol monomethyl ether acetate were added to a 200 mL three-neck flask, and the mixture was stirred at 80° C. for 30 minutes in a nitrogen stream. 138 mg of V-601 was added to the solution, and the mixture was stirred at 80° C. for 4 hours. Further, 25 mg of V-601 was added, and the mixture was stirred at 90° C. for 2 hours and cooled to room temperature. The obtained reaction mixture was slowly added to a mixture of 140 mL of hexane and 60 mL of isopropyl alcohol. The precipitated precipitate was collected by filtration and washed with a mixture of hexane and isopropyl alcohol. 140 mL of hexane and 60 mL of isopropyl alcohol were added to the obtained powder, and the mixture was stirred at room temperature for 1 hour and allowed to stand at room temperature overnight. The precipitate was collected by filtration, washed with a mixture of hexane and isopropyl alcohol, and dried at 50° C. 7.3 g of a target polymer B-1 was obtained. The number average molecular weight of the obtained polymer B-1 was 16,400 (in terms of polystyrene). 150 mg of the obtained polymer B-1 was dissolved in 100 mL of chloroform, and the absorption spectrum was measured. The maximum absorption wavelength of the polymer B-1 was 379 nm (absorbance of 1.11). The polymer B-1 was capable of sufficiently shielding light having a wavelength of approximately 400 nm. In addition, the polymer B-1 was less colored.

(Production Example 5) Production Example of Polymer B-2

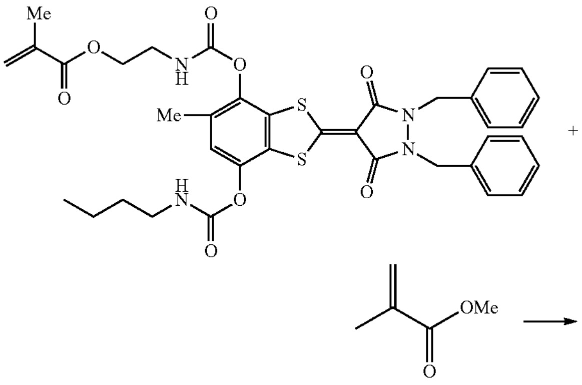

113 mg of the compound 1-54 (maximum absorption wavelength: 382 nm), 9.9 g of methyl methacrylate, and 40.0 g of propylene glycol monomethyl ether acetate were added to a 200 mL three-neck flask, and the mixture was stirred at 80° C. for 30 minutes in a nitrogen stream. 138 mg of V-601 was added to the solution, and the mixture was stirred at 80° C. for 4 hours. Further, 25 mg of V-601 was added, and the mixture was stirred at 90° C. for 2 hours and cooled to room temperature. The obtained reaction mixture was slowly added to a mixture of 140 mL of hexane and 60 mL of isopropyl alcohol. The precipitated precipitate was collected by filtration and washed with a mixture of hexane and isopropyl alcohol. 140 mL of hexane and 60 mL of isopropyl alcohol were added to the obtained powder, and the mixture was stirred at room temperature for 1 hour and allowed to stand at room temperature overnight. The precipitate was collected by filtration, washed with a mixture of hexane and isopropyl alcohol, and dried at 50° C. 7.0 g of a target polymer B-2 was obtained. The number average molecular weight of the obtained polymer B-2 was 17,800 (in terms of polystyrene). 150 mg of the obtained polymer B-2 was dissolved in 100 mL of chloroform, and the absorption spectrum was measured. The maximum absorption wavelength of the polymer B-2 was 385 nm (absorbance of 1.02). The polymer B-2 was capable of sufficiently shielding light having a wavelength of approximately 400 nm. In addition, the polymer B-2 was less colored.

(Comparative Production Example 1) Production Example of Polymer C-1

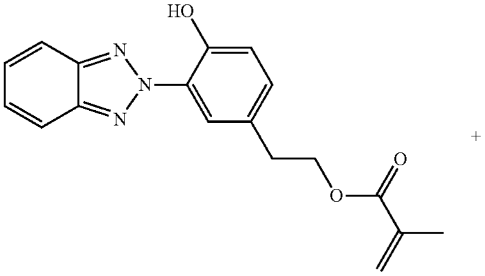

-continued

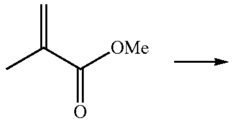

104 mg of 2-[2-hydroxy-5-(2-methacryloyloxyethyl)phenyl]2H-benzo[d][1,2,3]triazole, 9.9 g of methyl methacrylate, and 40.0 g of propylene glycol monomethyl ether acetate were added to a 200 mL three-neck flask, and the mixture was stirred at 80° C. for 30 minutes in a nitrogen stream. 1.135 mg of V-601 was added to the solution, and the mixture was stirred at 80° C. for 4 hours. Further, 37 mg of V-601 was added thereto, and the mixture was stirred at 90° C. for 2 hours and cooled to room temperature. The obtained reaction mixture was slowly added to a mixture of 140 mL of hexane and 60 mL of isopropyl alcohol. The precipitated precipitate was collected by filtration and washed with a mixture of hexane and isopropyl alcohol. 140 mL of hexane and 60 mL of isopropyl alcohol were added to the obtained powder, the mixture was stirred at room temperature for 3 hours, and the precipitate was collected by filtration, washed with a mixture of hexane and isopropyl alcohol, and dried at 50° C. 8.1 g of a target polymer C-1 was obtained. The number average molecular weight of the obtained polymer C-1 was 14,100 (in terms of polystyrene). 150 mg of the polymer C-1 was dissolved in 100 mL of chloroform, and the absorption spectrum was measured. The maximum absorption wavelength of the polymer C-1 was 339 nm (absorbance of 0.91). The polymer C-1 had poor shielding properties against light having a wavelength of 380 to 400 nm.

Test Example 1

Example 1

A resin solution in which 659 mg of the polymer A-1, 7.6 g of chloroform, and 0.44 g of a polymethyl methacrylate resin (DIANAL BR-80 (containing 60% by mass or greater of methyl methacrylate as a monomer unit, weight-average molecular weight: 95,000, acid value: 0 mgKOH/g, manufactured by Mitsubishi Chemical Corporation) were dissolved was prepared. Next, a glass substrate was spin-coated with the prepared resin solution, and the coating film was dried at 40° C. for 2 minutes to form a resin film containing the polymer A-1 and having a thickness of approximately 10 μm. The resin film of Example 1 was hardly colored and had excellent shielding properties against light having a wavelength of approximately 400 nm. Further, the shielding properties against light having a wavelength shorter than 350 nm were also excellent.

Example 2

A resin film was formed in the same manner as in Example 1 except that 659 mg of the polymer A-1 was changed to 661 mg of the polymer A-2 in Example 1. The resin film of Example 2 was hardly colored and had excellent shielding properties against light having a wavelength of approximately 400 nm. Further, the shielding properties against light having a wavelength shorter than 350 nm were also excellent.

Example 3

A resin film was formed in the same manner as in Example 1 except that 659 mg of the polymer A-1 was changed to 658 mg of the polymer A-3 in Example 1. The resin film of Example 3 was hardly colored and had excellent shielding properties against light having a wavelength of approximately 400 nm. Further, the shielding properties against light having a wavelength shorter than 350 nm were also excellent.

Comparative Example 1

A resin film was formed in the same manner as in Example 1 except that 659 mg of the polymer A-1 was changed to 1063 mg of the polymer C-1 and the blending amount of the polymethyl methacrylate resin was changed to 0.04 g in Example 1. The resin film of Comparative Example 1 had poor shielding properties against light having a wavelength of 380 to 400 nm.

[Evaluation of Light Resistance]

The light resistance of each resin film formed in Examples 1 to 3 and Comparative Example 1 was evaluated by acquiring the retention rate of the absorbance at the maximum absorption wavelength (λmax) under the following conditions. Specifically, the absorbance of the resin film at λmax was measured, the resin film was irradiated under the following conditions, and the absorbance at λmax after the irradiation for 28 days was measured. The retention rate (%) of the absorbance was calculated from the value of the absorbance at λmax before and after the irradiation according to the following equation. The retention rate of absorbance is listed in Table 1. The absorbance was acquired from the absorbance of light thereof using a spectrophotometer UV-1800PC (manufactured by Shimadzu Corporation).

Retention rate (%) of absorbance=(absorbance at λmax after irradiation)/(absorbance at λmax before irradiation)×100

Further, as the retention rate of the absorbance increases, the light resistance is more excellent.

(Conditions)

Device: low-temperature cycle xenon weather meter (XL75, manufactured by Suga Test Instruments Co., Ltd.)

Illuminance: 10 klx (40 w/$m^2$)

Time: 24 hours

Environment: 23° C. at relative humidity of 5%

TABLE 1

| | Type of polymer | λmax | Retention rate of absorbance |
|---|---|---|---|
| Example 1 | A-1 | 376 nm | 96% |
| | | 337 nm | 95% |
| Example 2 | A-2 | 376 nm | 97% |
| | | 335 nm | 96% |
| Example 3 | A-3 | 382 nm | 94% |
| | | 337 nm | 94% |
| Comparative Example 1 | C-1 | 338 nm | 90% |

λmax (maximum absorption wavelength) of 376 nm and 377 nm in Examples 1 and 2 denotes the maximum absorption wavelength derived from the compound 1-13.

λmax of 382 nm in Example 3 denotes the maximum absorption wavelength derived from the compound 1-54.

λmax (maximum absorption wavelength) of 337 nm and 338 nm in Examples 1 and 3 and Comparative Example 1 denotes the maximum absorption wavelength derived from 2-[2-hydroxy-5-(2-methacryloyloxyethyl)phenyl]2H-benzo[d][1,2,3]triazole.

λmax (maximum absorption wavelength) of 335 nm in Example 2 denotes the maximum absorption wavelength derived from the compound B described in JP2020-041013A.

It was found that the resin films of Examples 1 to 3 each had a high retention rate of the absorbance at each λmax (maximum absorption wavelength) and excellent light resistance.

Based on the comparison between Example 1 and Comparative Example 1, the retention rate of the absorbance at the maximum absorption wavelength derived from 2-[2-hydroxy-5-(2-methacryloyloxyethyl)phenyl]2H-benzo[d][1,2,3]triazole was 95% in Example 1, but the retention rate of the absorbance at the maximum absorption wavelength derived from 2-[2-hydroxy-5-(2-methacryloyloxyethyl)phenyl]2H-benzo[d][1,2,3]triazole was 90% in Comparative Example 1, which was inferior to that of Example 1.

Example 4

A resin film was formed in the same manner as in Example 1 except that 659 mg of the polymer A-1 was replaced with 659 mg of the exemplary polymer B-1 in Example 1. The resin film was hardly colored and had excellent shielding properties against light having a wavelength of approximately 400 nm. Further, the retention rate of absorbance of the resin film was evaluated by the same method as described above. The retention rate of the absorbance of the resin film of Example 4 at the maximum absorption wavelength (377 nm) was 97%, and the resin film had excellent light resistance.

Example 5

A resin film was formed in the same manner as in Example 1 except that 659 mg of the polymer A-1 was changed to 658 mg of the polymer B-2 in Example 1. The resin film was hardly colored and had excellent shielding properties against light having a wavelength of approximately 400 nm. Further, the shielding properties against light having a wavelength shorter than 350 nm were also excellent.

Test Example 2

[Production of Polymerizable Composition]

Respective materials were mixed at the ratio listed in the table below to produce polymerizable compositions 1 to 4. The numerical values listed in the table below are in units of parts by mass.

TABLE 2

| | Polymerizable composition 1 | Polymerizable composition 2 | Polymerizable composition 3 | Polymerizable composition 4 |
|---|---|---|---|---|
| Polymerizable monomer 1 | 92.0 | 90.9 | 91.0 | 90.9 |
| Polymerizable monomer 2 | 6.6 | 6.5 | 6.5 | 6.5 |
| Ultraviolet absorbing agent 1 | 1.0 | 1.0 | — | — |
| Ultraviolet absorbing agent 2 | — | — | 0.9 | — |
| Ultraviolet absorbing agent 3 | — | 1.2 | 1.2 | 1.2 |
| Ultraviolet absorbing agent 4 | — | — | — | 1.0 |
| Polymerization initiator 1 | 0.4 | 0.4 | 0.4 | 0.4 |

Polymerizable monomer 1: methyl methacrylate (manufactured by FUJIFILM Wako Pure Chemical Corporation)

Polymerizable monomer 2: benzyl methacrylate (manufactured by FUJIFILM Wako Pure Chemical Corporation)

Ultraviolet absorbing agent 1: compound 1-1 obtained in Synthesis Example 1 (maximum absorption wavelength: 375 nm)

Ultraviolet absorbing agent 2: mixture of compounds 1-17, 1-18, and 1-19 obtained in Synthesis Example 4 (maximum absorption wavelength: 379 nm)

Ultraviolet absorbing agent 3: 2-[2-hydroxy-5-(2-methacryloyloxyethyl)phenyl]2H-benzo[d][1,2,3]triazole (compound having the following structure, maximum absorption wavelength: 338 nm)

Ultraviolet absorbing agent 4: Compound 1-50 obtained in Synthesis Example 8 (maximum absorption wavelength: 383 nm)

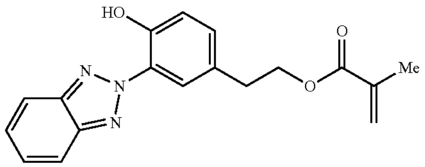 [SMILES: C=C(C)C(=O)OCCc1ccc(O)c(-n2nc3ccccc3n2)c1]

Polymerization initiator 1: Omnirad 819 (manufactured by IGM Resins B. V., compound having the following structure)

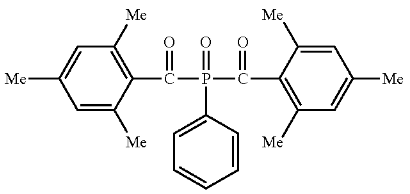 [SMILES: Cc1cc(C)c(C(=O)P(=O)(C(=O)c2c(C)cc(C)cc2C)c2ccccc2)c(C)c1]

Examples 11 to 14

Each polymerizable composition was sandwiched between crown glass plates having a thickness of 1 mm and irradiated with light at an irradiation amount of 1.0 $J/cm^2$ (2.5 $mW/cm^2$) using a light irradiation device (EXECURE 3000, manufactured by HOYA CANDEO OPTRONICS Corporation) to produce each of a polymer film of Example 11 (polymer film of the polymerizable composition 1), a polymer film of Example 12 (polymer film of the polymerizable composition 2), a polymer film of Example 13 (polymer film of the polymerizable composition 3), and a polymer film of Example 14 (polymer film of the polymerizable composition 4), in which each polymerizable composition was sandwiched between glass plates. The film thickness of each polymer film was adjusted to 50 μm.

[Measurement of Transmittance]

For each of the obtained polymer films, the transmittance of light having a wavelength of 300 to 600 nm was measured. The results are listed in the following table. The polymer films of Examples 11 to 14 were hardly colored and had excellent shielding properties against light having a wavelength of approximately 400 nm. Further, the resin films of Examples 12, 13, and 14 had excellent shielding properties against light having a wavelength shorter than 350 nm and also had excellent shielding properties against light having a wavelength of 330 to 400 nm.

TABLE 3

| | Example 11 | Example 12 | Example 13 | Example 14 |
|---|---|---|---|---|
| Transmittance (330 nm) | 19.9% | 0.0% | 0.0% | 0.0% |
| Transmittance (370 nm) | 0.0% | 0.0% | 0.0% | 0.0% |
| Transmittance (400 nm) | 10.1% | 9.6% | 8.6% | 7.1% |
| Transmittance (430 nm) | 83.9% | 83.0% | 82.8% | 85.1% |
| Transmittance (450 nm) | 95.4% | 95.5% | 95.2% | 96.1% |

[Evaluation of Storage Stability]

The polymer films of Examples 1 to 14 were stored under the conditions of 40° C. at a humidity of 50% for 1 week and allowed to stand at room temperature for 1 day, and the presence or absence of bleed-out and precipitation was visually observed. No bleed-out or precipitation was confirmed in all the polymer films 1 to 3.

[Evaluation of Light Resistance]

The retention rates of the absorbances of the polymer films of Examples 11 to 14 at the maximum absorption wavelength (max) were acquired in the same manner as in Test Example 1, and the light resistance was evaluated. Further, as the retention rate of the absorbance increases, the light resistance is more excellent.

TABLE 4

| | λmax | Retention rate of absorbance |
|---|---|---|
| Example 11 | 376 nm | 97% |
| Example 12 | 376 nm | 96% |
| | 339 nm | 95% |
| Example 13 | 379 nm | 95% |
| | 339 nm | 95% |
| Example 14 | 382 nm | 95% |
| | 339 nm | 95% |

As listed in the table above, the retention rates of the absorbances were high and the light resistance was excellent in all the polymer films of Examples 11 to 14.

What is claimed is:

1. A polymerizable composition comprising:

a compound represented by Formula (1); and an ultraviolet absorbing agent A having a maximum absorption wavelength on a shorter wavelength side than a maximum absorption wavelength of the compound represented by Formula (1),

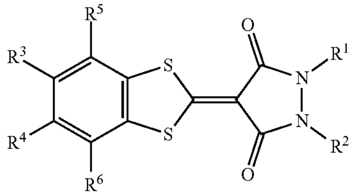

(1)

in Formula (1), $R^1$ to $R^6$ each independently represent a hydrogen atom or a substituent, $R^1$ and $R^2$ may be bonded to each other to form a ring, and $R^3$ and $R^4$ may be bonded to each other to form a ring, where at least one of $R^1$ to $R^6$ represents a group that contains a polymerizable group having an ethylenically unsaturated bond.

2. The polymerizable composition according to claim 1, wherein the compound represented by Formula (1) is a compound represented by Formula (2),

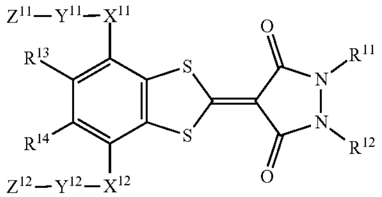

(2)

in Formula (2), $R^{11}$ and $R^{12}$ each independently represent a hydrogen atom, an alkyl group, or an aryl group, $R^{13}$ and $R^{14}$ each independently represent a hydrogen atom, a halogen atom, an alkyl group, an aryl group, an alkoxy group, or an aryloxy group, $X^{11}$ and $X^{12}$ each independently represent a single bond, —O—, —OC(═O)—, —OC(═O)O—, or —OC(═O)NRx$^{11}$-, where Rx$^{11}$ represents a hydrogen atom, an alkyl group, or an aryl group, $Y^{11}$ and $Y^{12}$ each independently represent a single bond or a divalent linking group, $Z^{11}$ and $Z^{12}$ each independently represent a hydrogen atom or a polymerizable group having an ethylenically unsaturated bond, $R^{11}$ and $R^{12}$ may be bonded to each other to form a ring, and $R^{13}$ and $R^{14}$ may be bonded to each other to form a ring, where at least one of $Z^{11}$ or $Z^{12}$ represents a polymerizable group having an ethylenically unsaturated bond.

3. The polymerizable composition according to claim 1, wherein the polymerizable group having an ethylenically unsaturated bond is a (meth)acryloyloxy group or a vinylphenyl group.

4. The polymerizable composition according to claim 1, wherein the maximum absorption wavelength of the ultraviolet absorbing agent A is present in a wavelength range of 300 to 380 nm.

5. The polymerizable composition according to claim 1, wherein the ultraviolet absorbing agent A is a compound containing a polymerizable group.

6. The polymerizable composition according to claim 1, wherein the ultraviolet absorbing agent A is at least one selected from a 2-(2-hydroxyphenyl)benzotriazole-based compound, a 2-(2-hydroxyphenyl)-1,3,5-triazine-based compound, or a 2-hydroxybenzophenone-based compound.

7. The polymerizable composition according to claim 1, further comprising:

a polymerizable compound other than the compound represented by Formula (1); and a polymerization initiator.

8. A polymer which is obtained by polymerizing the polymerizable composition according to claim 1.

9. An ultraviolet shielding material comprising:

the polymer according to claim 8.

10. A laminate comprising:

a support; and the ultraviolet shielding material according to claim 9.

11. A compound which is represented by Formula (5), (5)

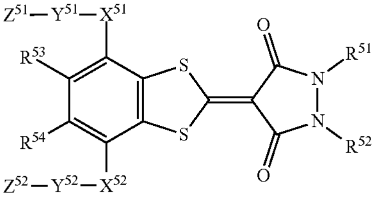

in Formula (5), $R^{51}$ and $R^{52}$ each independently represent a hydrogen atom, an alkyl group, or an aryl group, $R^{53}$ represents an alkyl group and $R^{54}$ represents a hydrogen atom, $X^{51}$ and $X^{52}$ each independently represent —O—, —OC(═O)O—, or —OC(═O)NH—, $Y^{51}$ and $Y^{52}$ each independently represent a single bond or a divalent linking group, the divalent linking group is a hydrocarbon group or a group having a structure in which two or more hydrocarbon groups are bonded via a linking group, and the linking group represents —O—, —C(═O)—, —OC(═O)—, —C(═O)O—, —NHC(═O)—, or —C(═O)NH—, and one of $Z^{51}$ and $Z^{52}$ represents a polymerizable group having an ethylenically unsaturated bond, and the other of $Z^{51}$ and $Z^{52}$ represents a hydrogen atom, in a case where $X^{51}$ represents —O— and $Z^{51}$ represents the polymerizable group having an ethylenically unsaturated bond, the polymerizable group having an ethylenically unsaturated bond which is represented by $Z^{51}$ is a vinylphenyl group, and in a case where $X^{52}$ represents —O— and $Z^{52}$ represents the polymerizable group having an ethylenically unsaturated bond, the polymerizable group having an ethylenically unsaturated bond which is represented by $Z^{52}$ is a vinylphenyl group.

12. The compound according to claim 11, wherein the polymerizable group having an ethylenically unsaturated bond is a (meth)acryloyloxy group or a vinylphenyl group.

13. The compound according to claim 11, wherein $X^{51}$ and $X^{52}$ each independently represent —O— or —OC(═O)NH—.

14. The compound according to claim 11, wherein $X^{51}$ has the same definition as that for $X^{52}$, and $Y^{51}$ has the same definition as that for $Y^{52}$.

15. An ultraviolet absorbing agent comprising:

the compound according to claim 11.

16. A polymer which has a structure derived from the compound according to claim 11.

17. A method of producing a compound, comprising:

reacting a compound represented by Formula (6) with a compound represented by Formula (7) to produce a compound represented by Formula (5), (6)

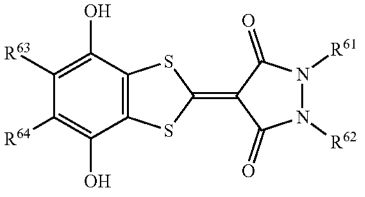

in Formula (6), $R^{61}$ and $R^{62}$ each independently represent a hydrogen atom, an alkyl group, or an aryl group, and $R^{63}$ represents an alkyl group and $R^{64}$ represents a hydrogen atom, $$Z^{71}—Y^{71}\text{-}E^{71} \quad (7)$$

in Formula (7), $E^{71}$ represents a group that reacts with a hydroxy group of Formula (6), $Y^{71}$ represents a single bond or a divalent linking group, the divalent linking group is a hydrocarbon group or a group having a structure in which two or more hydrocarbon groups are bonded via a linking group, and the linking group represents —O—, —C(═O)—, —OC(═O)—, —C(═O)O—, —NHC(═O)—, or —C(═O)NH—, and $Z^{71}$ represents a polymerizable group having an ethylenically unsaturated bond, (5)

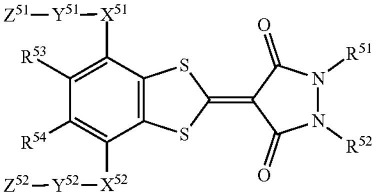

in Formula (5), $R^{51}$ and $R^{52}$ each independently represent a hydrogen atom, an alkyl group, or an aryl group, $R^{53}$ represents an alkyl group and $R^{54}$ represents a hydrogen atom, $X^{51}$ and $X^{52}$ each independently represent —O—, —OC(═O)O—, or —OC(═O)NH—, $Y^{51}$ and $Y^{52}$ each independently represent a single bond or a divalent linking group, the divalent linking group is a hydrocarbon group or a group having a structure in which two or more hydrocarbon groups are bonded via a linking group, and the linking group represents —O—, —C(=O)—, —OC(=O)—, —C(=O)O—, —NHC(=O)—, or —C(=O)NH—, and one of $Z^{51}$ and $Z^{52}$ represents a polymerizable group having an ethylenically unsaturated bond, and the other of $Z^{51}$ and $Z^{52}$ represents a hydrogen atom, in a case where $X^{51}$ represents —O— and $Z^{51}$ represents the polymerizable group having an ethylenically unsaturated bond, the polymerizable group having an ethylenically unsaturated bond which is represented by $Z^{51}$ is a vinylphenyl group, and in a case where $X^{52}$ represents —O— and $Z^{52}$ represents the polymerizable group having an ethylenically unsaturated bond, the polymerizable group having an ethylenically unsaturated bond which is represented by $Z^{52}$ is a vinylphenyl group.

18. The method of producing a compound according to claim 17, wherein $E^{71}$ in Formula (7) represents —COCl, —O(C=O)Cl, —NCO, —Cl, —Br, —I, $—OSO_2D^1$, or an oxiranyl group, where $D^1$ represents a methyl group, an ethyl group, a phenyl group, or a 4-methylphenyl group.

* * * * *